(12) United States Patent
Ohara et al.

(10) Patent No.: US 8,173,778 B2
(45) Date of Patent: May 8, 2012

(54) ANTIBODY TO A GUANINE NUCLEOTIDE EXCHANGE FACTOR

(75) Inventors: Osamu Ohara, Chiba (JP); Takahiro Nagase, Chiba (JP); Michio Oishi, Chiba (JP); Hiroshi Yokota, Tokyo (JP); Osamu Kamida, Tokyo (JP)

(73) Assignee: Daiichi Sankyo Company, Limited, Tokyo (JP)

( * ) Notice: Subject to any disclaimer, the term of this patent is extended or adjusted under 35 U.S.C. 154(b) by 298 days.

(21) Appl. No.: 12/651,145

(22) Filed: Dec. 31, 2009

(65) Prior Publication Data

US 2010/0125131 A1 May 20, 2010

Related U.S. Application Data

(62) Division of application No. 10/594,707, filed as application No. PCT/JP2005/005918 on Mar. 29, 2005, now Pat. No. 7,667,013.

(30) Foreign Application Priority Data

Mar. 31, 2004 (JP) ................................. 2004-106268

(51) Int. Cl.
*C07K 16/00* (2006.01)
(52) U.S. Cl. ...................... 530/387.1; 435/810; 435/975
(58) Field of Classification Search .................. None
See application file for complete search history.

(56) References Cited

FOREIGN PATENT DOCUMENTS

| WO | WO 98/57990 | 12/1998 |
|---|---|---|
| WO | WO 00/12711 A1 | 3/2000 |
| WO | WO 02/068579 A2 | 9/2002 |

OTHER PUBLICATIONS

International Preliminary Report on Patentability and Written Opinion for PCT/JP/2005/005918 dated Oct. 26, 2006.
Hart et al., Cellular Transformation and Guanine Nucleotide Exchange Activity Are Catalyzed by a Common Domain on the *dbl* Oncogene Product, The Journal of Biological Chemistry, vol. 269, No. 1, Jan. 7, 1994, pp. 62-65.
Bi et al., "Autoinhibition Mechanism of Proto-Dbl," Molecular and Cellular Biology, vol. 21, No. 5, Mar. 2001, pp. 1463-1474.
Katzav et al., "*VAV*, a novel human oncogene derived from a locus ubiquitously expressed in hematopoietic cells," The EMBO Journal, vol. 8, No. 8, 1989, pp. 2283-2290.
Costello et al., "The Rho-family GTP exchange factor Vav is a critical transducer of T cell receptor signals to the calcium, ERK, and NF-κB pathways," Proc. Natl. Acad, Sci. USA, vol. 96, Mar. 1999, pp. 3035-3040.
Horii et al., "A novel oncogene, *ost*, encodes a guanine nucleotide exchange factor that potentially links Rho and Rac signaling pathways," The EMBO Journal, vol. 13, No. 20, 1994, pp. 4776-4786.
Toksoz et al., "Novel human oncogene LBC detected by transfection with distinct homology regions to signal transduction products," Oncogene, No. 9, 1994, pp. 621-628.
O'Brien et al., "Skeletal muscle deformity and neuronal disorder in Trio exchange factor-deficient mouse embryos," PNAS, vol. 97, No. 22, Oct. 24, 2000, pp. 12074-12078.
Penzes et al., "Distinct Roles for the Two Rho GDP/GTP Exchange Factor Domains of Kalirin in Regulation of Neurite Growth and Neuronal Morphology," The Journal of Neuroscience, vol. 21(21), Nov. 1, 2001, pp. 8426-8434.
Ohara et al., "Construction and Characterization of Human Brain cDNA Libraries Suitable for Analysis of cDNA Clones Encoding Relatively Large Proteins," DNA Research, 4, 1997, pp. 53-59.
Supplementary Partial European Search Report for corresponding European Patent Application No. 05 72 7864 dated Jun. 9, 2008 (6 pages).
Database EMBL, No. XP-002480250, "Mus musculus 4 days neonate male adipose cDNA, RIKEN full-length enriched library, clone: B430212B09 product: hypothetical Dbl, domain (dbl/cdc24 rhoGEF family), PH Domain containing protein, full insert sequence," dated Dec. 18, 2002, retrieved from EBI accession No. EMBL: AK080928 (3 pages).
Zheng, "Dbl family guanine nucleotide exchange factors," TRENDS in Biochemical Sciences, vol. 26, No. 12, Dec. 1, 2001 (pp. 724-732).
Database EMBL, No. XP-002480251, "*Homo sapiens* KIAA0599, mRNA (cDNA clone Image: 4939677), partial cds," dated Dec. 10, 2003, retrieved from EBI accession No. EMBL: BC063554 (3 pages).
Database EMBL, No. XP-002480252, "*Homo sapiens* mRNA for FLJ00242 protein," dated Feb. 15, 2002, retrieved from EBI accession No. EMBL: AK074169 (2 pages).
Pan et al., "Expression of seven main Rho family members in gastric carcinoma," Biochemical and Biophysical Research Communications, vol. 315, No. 3, Mar. 12, 2004 (pp. 686-691).

*Primary Examiner* — Prema Mertz
(74) *Attorney, Agent, or Firm* — Kilyk & Bowersox, P.L.L.C.

(57) ABSTRACT

A gene encoding a novel protein that works as a guanine nucleotide exchange factor (GEF) for a Rho family protein being one group of small GTP-binding proteins, namely, a polynucleotide shown by the nucleotide sequence set forth in SEQ ID NO: 1, SEQ ID NO: 3, or SEQ ID NO: 5, or the complementary strand, the equivalents of the polynucleotide, a protein encoded by the polynucleotide, a vector containing the polynucleotide, a transformant containing the vector, an antibody against the protein encoded by the polynucleotide, a method of identifying a compound that inhibits the function of the protein encoded by the polynucleotide and/or the expression of the polynucleotide, a method of determining a disease, a pharmaceutical composition, and a reagent kit are provided.

2 Claims, 2 Drawing Sheets

SEQUENCE LISTING

```
<160> NUMBER OF SEQ ID NOS: 27

<210> SEQ ID NO 1
<211> LENGTH: 4977
<212> TYPE: DNA
<213> ORGANISM: Homo sapiens
<220> FEATURE:
<221> NAME/KEY: misc_feature
<223> OTHER INFORMATION: Polynucleotide encoding the protein (SEQ ID
      NO:2) that have a function of guanine nucleotide exchange factor.
<220> FEATURE:
<221> NAME/KEY: CDS
<222> LOCATION: (314)..(4336)
<220> FEATURE:
<221> NAME/KEY: misc_feature
<222> LOCATION: (602)..(1126)
<223> OTHER INFORMATION: A region encoding Dbl homology domain
<220> FEATURE:
<221> NAME/KEY: misc_feature
<222> LOCATION: (1202)..(1495)
<223> OTHER INFORMATION: A region encoding Pleckstrin homology domain

<400> SEQUENCE: 1
cgctccctcg ctccctcctg ccctcccgct gcagctccgg ctccgctcga cttcctgccg      60
ggcgctggca agccgcgcgc tgcctggggt ctccggggc cgcgcttgca gctggccgag     120
tccgggccag ctgaggggct ggcggtgggc gggagcggtc ggcggcctca gcccttcag    180 agagcgactt tcaaactcgc gcccgcgtcg cggcagcacc tgggcagccc cgcacgccgt     240
gcgcgtcccg agcccgcggg gcagctaccg ctcgaatctc cctggggtgc cctccccagg     300
cagcaatgcc agg atg cct gtg tcc acc tcc ctc cac cag gat ggc agc       349
            Met Pro Val Ser Thr Ser Leu His Gln Asp Gly Ser
              1               5                  10 cag gag cgg ccg gtg agc ctg acc tct acc acc tcc tcg tcg ggc tcc      397
Gln Glu Arg Pro Val Ser Leu Thr Ser Thr Thr Ser Ser Ser Gly Ser
        15                  20                  25 tcc tgt gac agt cgc agt gcc atg gag gag ccc agc agc tcc gag gct      445
Ser Cys Asp Ser Arg Ser Ala Met Glu Glu Pro Ser Ser Ser Glu Ala
    30                  35                  40 ccc gcc aag aat ggg gca ggc tcc ctg aga agc cgg cat ctg ccc aac      493
Pro Ala Lys Asn Gly Ala Gly Ser Leu Arg Ser Arg His Leu Pro Asn
45                  50                  55                  60 agc aac aac aac tcc agc agc tgg ttg aac gtg aag ggg ccc ctc tcc      541
```

```
            Ser Asn Asn Asn Ser Ser Ser Trp Leu Asn Val Lys Gly Pro Leu Ser
                            65                  70                  75 ccg ttc aac agc cgg gca gcg gca ggg cct gca cac cac aag ctc agc          589
Pro Phe Asn Ser Arg Ala Ala Ala Gly Pro Ala His His Lys Leu Ser
            80                  85                  90 tac ctg ggc cga gtg gtg cgg gag atc gtg gag aca gag cgc atg tac          637
Tyr Leu Gly Arg Val Val Arg Glu Ile Val Glu Thr Glu Arg Met Tyr
        95                  100                 105 gta cag gac ctg cgc agc atc gtg gag gac tac ctc ttg aag atc att          685
Val Gln Asp Leu Arg Ser Ile Val Glu Asp Tyr Leu Leu Lys Ile Ile
    110                 115                 120 gac aca ccc ggg ctg ctg aag cca gaa cag gtc agc gcc ctc ttt ggg          733
Asp Thr Pro Gly Leu Leu Lys Pro Glu Gln Val Ser Ala Leu Phe Gly
125                 130                 135                 140 aac ata gaa aac atc tac gcg ctg aac agc cag ctc ctc aga gac ctg          781
Asn Ile Glu Asn Ile Tyr Ala Leu Asn Ser Gln Leu Leu Arg Asp Leu
                145                 150                 155 gac agc tgc aat agt gac ccc gtg gct gtg gcc agc tgc ttt gtg gaa          829
Asp Ser Cys Asn Ser Asp Pro Val Ala Val Ala Ser Cys Phe Val Glu
            160                 165                 170 agg agc caa gag ttt gat atc tac act cag tat tgc aac aat tac ccc          877
Arg Ser Gln Glu Phe Asp Ile Tyr Thr Gln Tyr Cys Asn Asn Tyr Pro
        175                 180                 185 aac tcc gtg gcc gcc ctg acg gaa tgc atg cgg gac aag cag cag gcc          925
Asn Ser Val Ala Ala Leu Thr Glu Cys Met Arg Asp Lys Gln Gln Ala
    190                 195                 200 aag ttc ttt cgg gac cgg cag gag ctg cta cag cac tcg ctg ccc ttg          973
Lys Phe Phe Arg Asp Arg Gln Glu Leu Leu Gln His Ser Leu Pro Leu
205                 210                 215                 220 ggc tcc tac ctg ctg aag cca gtc cag cgc atc ctc aag tac cac ctg         1021
Gly Ser Tyr Leu Leu Lys Pro Val Gln Arg Ile Leu Lys Tyr His Leu
                225                 230                 235 ctg ctc cag gaa att gcc aaa cat ttt gat gaa gaa gag gat ggc ttt         1069
Leu Leu Gln Glu Ile Ala Lys His Phe Asp Glu Glu Glu Asp Gly Phe
            240                 245                 250 gag gtg gtg gag gat gcc att gac acc atg acc tgt gtg gcc tgg tac         1117
Glu Val Val Glu Asp Ala Ile Asp Thr Met Thr Cys Val Ala Trp Tyr
        255                 260                 265 atc aac gac atg aag agg agg cat gag cac gcg gtc cgg ctc cag gag         1165
Ile Asn Asp Met Lys Arg Arg His Glu His Ala Val Arg Leu Gln Glu
    270                 275                 280 att cag tca ctc ctc atc aac tgg aag ggg ccc gac ctg acc acc tac         1213
Ile Gln Ser Leu Leu Ile Asn Trp Lys Gly Pro Asp Leu Thr Thr Tyr
285                 290                 295                 300 ggg gag ctt gtc ctg gag ggc aca ttc cgc gtg cat cgc gtg cgc aat         1261
Gly Glu Leu Val Leu Glu Gly Thr Phe Arg Val His Arg Val Arg Asn
                305                 310                 315 gaa agg acc ttt ttc ctc ttt gac aaa aca ctg ctt atc acc aag aag         1309
Glu Arg Thr Phe Phe Leu Phe Asp Lys Thr Leu Leu Ile Thr Lys Lys
            320                 325                 330 cgg ggc gat cac ttt gtc tac aag ggc aac atc ccg tgc tcc tcc ctg         1357
Arg Gly Asp His Phe Val Tyr Lys Gly Asn Ile Pro Cys Ser Ser Leu
        335                 340                 345 atg ctg atc gaa agc acc aga gac tcc ctg tgc ttc act gtc acc cac         1405
Met Leu Ile Glu Ser Thr Arg Asp Ser Leu Cys Phe Thr Val Thr His
    350                 355                 360 tac aag cac agc aag cag cag tac agc atc cag gcc aag aca gtg gag         1453
Tyr Lys His Ser Lys Gln Gln Tyr Ser Ile Gln Ala Lys Thr Val Glu
365                 370                 375                 380 gag aaa cgg aac tgg act cac cac atc aag agg ctc atc cta gag aac         1501
```

-continued

```
                    Glu Lys Arg Asn Trp Thr His His Ile Lys Arg Leu Ile Leu Glu Asn
                                    385                 390                 395 cac cat gcc acc att ccc cag aag gcc aag gaa gcc atc ttg gaa atg          1549
His His Ala Thr Ile Pro Gln Lys Ala Lys Glu Ala Ile Leu Glu Met
            400                 405                 410 gat tcc tat tat ccc aat cgg tac cgc tgc agc cca gag cgg ctg aag          1597
Asp Ser Tyr Tyr Pro Asn Arg Tyr Arg Cys Ser Pro Glu Arg Leu Lys
            415                 420                 425 aag gct tgg tcc tcc cag gat gag gtg tcc acc aat gtg cgc cag ggg          1645
Lys Ala Trp Ser Ser Gln Asp Glu Val Ser Thr Asn Val Arg Gln Gly
        430                 435                 440 cgc cgg caa tct gag cca acc aaa cac ctg ctc agg caa ctc aac gag          1693
Arg Arg Gln Ser Glu Pro Thr Lys His Leu Leu Arg Gln Leu Asn Glu
445                 450                 455                 460 aaa gcc cga gca gca gga atg aag cat gca ggc agt gct gga acc ctc          1741
Lys Ala Arg Ala Ala Gly Met Lys His Ala Gly Ser Ala Gly Thr Leu
                465                 470                 475 ctg gac ttt ggg cag ccc tcc cgt act cgg ggc ctg cag cca gag gct          1789
Leu Asp Phe Gly Gln Pro Ser Arg Thr Arg Gly Leu Gln Pro Glu Ala
            480                 485                 490 gaa ggg gct acc cag gag gag gaa gag gaa gag gag gtg gtg gag              1837
Glu Gly Ala Thr Gln Glu Glu Glu Glu Glu Glu Val Val Glu
            495                 500                 505 gag gag gag gag gag gag gag gaa gag cag gcc ttt cag gtc tct ctg          1885
Glu Glu Glu Glu Glu Glu Glu Glu Gln Ala Phe Gln Val Ser Leu
510                 515                 520 gag gac ctg aca ggg cat gaa ggc aac gag aag ggg gct ggg ccg gag          1933
Glu Asp Leu Thr Gly His Glu Gly Asn Glu Lys Gly Ala Gly Pro Glu
525                 530                 535                 540 ccc cca ggc tca gag gag gag gag gag cag gag gag agc ctg gcg              1981
Pro Pro Gly Ser Glu Glu Glu Glu Glu Gln Glu Glu Ser Leu Ala
                545                 550                 555 gtg gcg gag cag gta gcc gac ttt gcc agc tcc ctg ctg gcc gcc ctc          2029
Val Ala Glu Gln Val Ala Asp Phe Ala Ser Ser Leu Leu Ala Ala Leu
            560                 565                 570 cac tgc tgg cac tat cgg gcc aac gct tta ctt ttc tcc cgg ggc gct          2077
His Cys Trp His Tyr Arg Ala Asn Ala Leu Leu Phe Ser Arg Gly Ala
        575                 580                 585 atg gga aag ggg cgc agg gag tct gaa agc tcc agg agc agc aga agg          2125
Met Gly Lys Gly Arg Arg Glu Ser Glu Ser Ser Arg Ser Ser Arg Arg
590                 595                 600 ccc agt ggc cgg tct cca acc agt act gag aag cgc atg agc ttc gag          2173
Pro Ser Gly Arg Ser Pro Thr Ser Thr Glu Lys Arg Met Ser Phe Glu
605                 610                 615                 620 tcc att tct tcc ctg cca gag gtt gag ccg gac cct gag gct ggg agt          2221
Ser Ile Ser Ser Leu Pro Glu Val Glu Pro Asp Pro Glu Ala Gly Ser
                625                 630                 635 gag caa gag gta ttt tct gct gtg aaa ggg ccc agt gcc gag gag acg          2269
Glu Gln Glu Val Phe Ser Ala Val Glu Gly Pro Ser Ala Glu Glu Thr
            640                 645                 650 cct tca gac aca gaa tct cca gaa gtc ctg gag aca cag ctt gat gcc          2317
Pro Ser Asp Thr Glu Ser Pro Glu Val Leu Glu Thr Gln Leu Asp Ala
        655                 660                 665 cac cag ggc ctt ctg ggg atg gac ccc cca ggt gac atg gtg gac ttc          2365
His Gln Gly Leu Leu Gly Met Asp Pro Pro Gly Asp Met Val Asp Phe
670                 675                 680 gtg gca gct gag agc act gag gac ctt aag gcc ctg agc agc gag gag          2413
Val Ala Ala Glu Ser Thr Glu Asp Leu Lys Ala Leu Ser Ser Glu Glu
685                 690                 695                 700 gaa gaa gaa atg gga ggt gcc gcc cag gag cct gag agc ctt ctg cca          2461
```

```
Glu Glu Glu Met Gly Gly Ala Ala Gln Glu Pro Ser Leu Leu Pro
            705                 710                 715 ccc tcc gtg ctg gac cag gcc agc gtc att gcg gag cga ttt gtc agc    2509
Pro Ser Val Leu Asp Gln Ala Ser Val Ile Ala Glu Arg Phe Val Ser
            720                 725                 730 agc ttc tct cgg cgg agc agc gtg gca cag gag gac agc aag tcc agt    2557
Ser Phe Ser Arg Arg Ser Ser Val Ala Gln Glu Asp Ser Lys Ser Ser
            735                 740                 745 ggc ttt ggg agc ccg cgg ctg gtc agc cgg agc agc gtg ctc agc        2605
Gly Phe Gly Ser Pro Arg Leu Val Ser Arg Ser Ser Val Leu Ser
        750                 755                 760 ctg gag ggc agc gag aag ggc ctg gcc cgg cat ggc agt gcc aca gac    2653
Leu Glu Gly Ser Glu Lys Gly Leu Ala Arg His Gly Ser Ala Thr Asp
765                 770                 775                 780 tcc ctc agc tgt cag ctc tcc cca gaa gtg gac atc agt gtg ggg gtg    2701
Ser Leu Ser Cys Gln Leu Ser Pro Glu Val Asp Ile Ser Val Gly Val
                785                 790                 795 gcc aca gag gac agc cct tct gtc aat ggg atg gag ccc cca agc cca    2749
Ala Thr Glu Asp Ser Pro Ser Val Asn Gly Met Glu Pro Pro Ser Pro
            800                 805                 810 ggc tgc cca gtg gag cct gac cgg tct tcc tgc aag aag aag gaa tca    2797
Gly Cys Pro Val Glu Pro Asp Arg Ser Ser Cys Lys Lys Lys Glu Ser
            815                 820                 825 gca ctc tcc acc cga gac cgg ctg ttg cta gac aag att aag agc tat    2845
Ala Leu Ser Thr Arg Asp Arg Leu Leu Leu Asp Lys Ile Lys Ser Tyr
        830                 835                 840 tat gaa aat gca gaa cac cat gat gca ggc ttc agc gtc cgt cgc cgg    2893
Tyr Glu Asn Ala Glu His His Asp Ala Gly Phe Ser Val Arg Arg Arg
845                 850                 855                 860 gag agc ctc tcc tac atc ccc aaa gga ctg gta aga aac tcc atc tcc    2941
Glu Ser Leu Ser Tyr Ile Pro Lys Gly Leu Val Arg Asn Ser Ile Ser
                865                 870                 875 agg ttc aac agc ctt ccc cgg cca gac cca gag cca gta cct cca gtg    2989
Arg Phe Asn Ser Leu Pro Arg Pro Asp Pro Glu Pro Val Pro Pro Val
            880                 885                 890 ggg agc aag aga cag gtg ggc tcc cgg ccg act tcg tgg gcc ctg ttt    3037
Gly Ser Lys Arg Gln Val Gly Ser Arg Pro Thr Ser Trp Ala Leu Phe
            895                 900                 905 gag ctc cca gga cca agc cag gca gtc aaa ggg gac cca cct ccc atc    3085
Glu Leu Pro Gly Pro Ser Gln Ala Val Lys Gly Asp Pro Pro Pro Ile
        910                 915                 920 tca gat gct gag ttc cgc cca tct tca gaa att gtg aag atc tgg gag    3133
Ser Asp Ala Glu Phe Arg Pro Ser Ser Glu Ile Val Lys Ile Trp Glu
925                 930                 935                 940 gga atg gag tct tcc gga ggg agc cct ggg aag ggg cca ggc cag ggc    3181
Gly Met Glu Ser Ser Gly Gly Ser Pro Gly Lys Gly Pro Gly Gln Gly
                945                 950                 955 cag gcc aat ggc ttt gac ctg cat gag cca ctc ttc atc ctg gag gag    3229
Gln Ala Asn Gly Phe Asp Leu His Glu Pro Leu Phe Ile Leu Glu Glu
            960                 965                 970 cat gag ctg gga gcc atc aca gag gag tcg gcc act gcc tcc ccg gaa    3277
His Glu Leu Gly Ala Ile Thr Glu Glu Ser Ala Thr Ala Ser Pro Glu
            975                 980                 985 agc tcc tct ccc act gag ggg cgc agc ccg gcc cac ctg gcc cgg gag    3325
Ser Ser Ser Pro Thr Glu Gly Arg Ser Pro Ala His  Leu Ala Arg Glu
        990                 995                 1000 ctg  aaa gag ctg gtg aag  gag ctg agc agc agt  acc cag ggg gag    3370
Leu  Lys Glu Leu Val Lys  Glu Leu Ser Ser Ser  Thr Gln Gly Glu
1005              1010                  1015 ctg  gtg gcc cca ctg cac   ccc cgc atc gtg cag  ctc tcc cac gta   3415
```

| | | | | | | | | | | | |
|---|---|---|---|---|---|---|---|---|---|---|---|
| Leu | Val | Ala | Pro | Leu | His | Pro | Arg | Ile | Val | Gln | Leu Ser His Val |
| 1020 | | | | 1025 | | | | | 1030 | | |

| | | | | | | | | | | | | |
|---|---|---|---|---|---|---|---|---|---|---|---|---|
| atg | gac | agc | cac | gtg | agc | gag | cgc | gtc | aag | aac | aag gtc tac cag | 3460 |
| Met | Asp | Ser | His | Val | Ser | Glu | Arg | Val | Lys | Asn | Lys Val Tyr Gln | |
| 1035 | | | | 1040 | | | | | 1045 | | | |

| | | | | | | | | | | | | |
|---|---|---|---|---|---|---|---|---|---|---|---|---|
| ctg | gcc | cgc | cag | tac | agc | ctc | cgg | atc | aag | agc | aac aag cca gtg | 3505 |
| Leu | Ala | Arg | Gln | Tyr | Ser | Leu | Arg | Ile | Lys | Ser | Asn Lys Pro Val | |
| 1050 | | | | 1055 | | | | | 1060 | | | |

| | | | | | | | | | | | | |
|---|---|---|---|---|---|---|---|---|---|---|---|---|
| atg | gcc | agg | cca | cca | ctg | cag | tgg | gaa | aag | gtg | gcc cct gag agg | 3550 |
| Met | Ala | Arg | Pro | Pro | Leu | Gln | Trp | Glu | Lys | Val | Ala Pro Glu Arg | |
| 1065 | | | | 1070 | | | | | 1075 | | | |

| | | | | | | | | | | | | |
|---|---|---|---|---|---|---|---|---|---|---|---|---|
| gat | ggg | aag | agc | ccc | act | gtg | ccc | tgt | cta | cag | gaa gag gct gga | 3595 |
| Asp | Gly | Lys | Ser | Pro | Thr | Val | Pro | Cys | Leu | Gln | Glu Glu Ala Gly | |
| 1080 | | | | 1085 | | | | | 1090 | | | |

| | | | | | | | | | | | | |
|---|---|---|---|---|---|---|---|---|---|---|---|---|
| gag | cca | tta | ggt | ggc | aaa | ggt | aag | agg | aag | ccg | gtg ctg tct cta | 3640 |
| Glu | Pro | Leu | Gly | Gly | Lys | Gly | Lys | Arg | Lys | Pro | Val Leu Ser Leu | |
| 1095 | | | | 1100 | | | | | 1105 | | | |

| | | | | | | | | | | | | |
|---|---|---|---|---|---|---|---|---|---|---|---|---|
| ttt | gac | tat | gag | cag | ctg | atg | gcc | cag | gag | cac | agc cct ccc aag | 3685 |
| Phe | Asp | Tyr | Glu | Gln | Leu | Met | Ala | Gln | Glu | His | Ser Pro Pro Lys | |
| 1110 | | | | 1115 | | | | | 1120 | | | |

| | | | | | | | | | | | | |
|---|---|---|---|---|---|---|---|---|---|---|---|---|
| ccc | tcc | tcg | gct | ggg | gag | atg | tca | cca | cag | cgt | ttc ttc ttc aac | 3730 |
| Pro | Ser | Ser | Ala | Gly | Glu | Met | Ser | Pro | Gln | Arg | Phe Phe Phe Asn | |
| 1125 | | | | 1130 | | | | | 1135 | | | |

| | | | | | | | | | | | | |
|---|---|---|---|---|---|---|---|---|---|---|---|---|
| ccg | tct | gct | gtc | agc | cag | agg | acc | acc | tcg | cct | ggg ggc cgg ccc | 3775 |
| Pro | Ser | Ala | Val | Ser | Gln | Arg | Thr | Thr | Ser | Pro | Gly Gly Arg Pro | |
| 1140 | | | | 1145 | | | | | 1150 | | | |

| | | | | | | | | | | | | |
|---|---|---|---|---|---|---|---|---|---|---|---|---|
| tcc | gcc | tgg | agc | ccc | ctc | agc | ccc | aca | gag | acc | ttc agc tgg ccc | 3820 |
| Ser | Ala | Trp | Ser | Pro | Leu | Ser | Pro | Thr | Glu | Thr | Phe Ser Trp Pro | |
| 1155 | | | | 1160 | | | | | 1165 | | | |

| | | | | | | | | | | | | |
|---|---|---|---|---|---|---|---|---|---|---|---|---|
| gac | gtc | cgt | gag | ctc | tgc | tcc | aag | tat | gcc | tcc | cgc gat gag gca | 3865 |
| Asp | Val | Arg | Glu | Leu | Cys | Ser | Lys | Tyr | Ala | Ser | Arg Asp Glu Ala | |
| 1170 | | | | 1175 | | | | | 1180 | | | |

| | | | | | | | | | | | | |
|---|---|---|---|---|---|---|---|---|---|---|---|---|
| cgc | cga | gca | ggg | ggc | ggc | cgg | ccc | cgc | ggc | cca | ccc gtc aac agg | 3910 |
| Arg | Arg | Ala | Gly | Gly | Gly | Arg | Pro | Arg | Gly | Pro | Pro Val Asn Arg | |
| 1185 | | | | 1190 | | | | | 1195 | | | |

| | | | | | | | | | | | | |
|---|---|---|---|---|---|---|---|---|---|---|---|---|
| agc | cac | tcg | gtg | ccg | gag | aac | atg | gta | gag | cca | cct ctg tcg ggc | 3955 |
| Ser | His | Ser | Val | Pro | Glu | Asn | Met | Val | Glu | Pro | Pro Leu Ser Gly | |
| 1200 | | | | 1205 | | | | | 1210 | | | |

| | | | | | | | | | | | | |
|---|---|---|---|---|---|---|---|---|---|---|---|---|
| agg | gtg | ggc | cgc | tgc | cgc | agc | ctg | agc | acc | aag | agg ggc cgg gga | 4000 |
| Arg | Val | Gly | Arg | Cys | Arg | Ser | Leu | Ser | Thr | Lys | Arg Gly Arg Gly | |
| 1215 | | | | 1220 | | | | | 1225 | | | |

| | | | | | | | | | | | | |
|---|---|---|---|---|---|---|---|---|---|---|---|---|
| ggc | gga | gag | gct | gcc | caa | tcc | cct | ggg | cct | ctg | ccc cag agc aag | 4045 |
| Gly | Gly | Glu | Ala | Ala | Gln | Ser | Pro | Gly | Pro | Leu | Pro Gln Ser Lys | |
| 1230 | | | | 1235 | | | | | 1240 | | | |

| | | | | | | | | | | | | |
|---|---|---|---|---|---|---|---|---|---|---|---|---|
| ccg | gat | gga | ggc | gag | acc | ctg | tat | gtc | act | gca | gac ctc acc ctg | 4090 |
| Pro | Asp | Gly | Gly | Glu | Thr | Leu | Tyr | Val | Thr | Ala | Asp Leu Thr Leu | |
| 1245 | | | | 1250 | | | | | 1255 | | | |

| | | | | | | | | | | | | |
|---|---|---|---|---|---|---|---|---|---|---|---|---|
| gag | gac | aac | cgg | cgg | gtg | att | gtc | atg | gag | aag | gga ccc ctt ccc | 4135 |
| Glu | Asp | Asn | Arg | Arg | Val | Ile | Val | Met | Glu | Lys | Gly Pro Leu Pro | |
| 1260 | | | | 1265 | | | | | 1270 | | | |

| | | | | | | | | | | | | |
|---|---|---|---|---|---|---|---|---|---|---|---|---|
| agc | ccc | act | gca | ggg | ctg | gag | gag | agc | agt | ggc | cag gga cca agc | 4180 |
| Ser | Pro | Thr | Ala | Gly | Leu | Glu | Glu | Ser | Ser | Gly | Gln Gly Pro Ser | |
| 1275 | | | | 1280 | | | | | 1285 | | | |

| | | | | | | | | | | | | |
|---|---|---|---|---|---|---|---|---|---|---|---|---|
| tca | ccg | gtg | gcc | ctg | ctg | ggg | cag | gtt | cag | gac | ttc cag cag tct | 4225 |
| Ser | Pro | Val | Ala | Leu | Leu | Gly | Gln | Val | Gln | Asp | Phe Gln Gln Ser | |
| 1290 | | | | 1295 | | | | | 1300 | | | |

| | | | | | | | | | | | | |
|---|---|---|---|---|---|---|---|---|---|---|---|---|
| gca | gag | tgc | cag | ccg | aag | gaa | gag | ggt | tcc | agg | gac ccg gca gac | 4270 |
| Ala | Glu | Cys | Gln | Pro | Lys | Glu | Glu | Gly | Ser | Arg | Asp Pro Ala Asp | |
| 1305 | | | | 1310 | | | | | 1315 | | | |

| | | | | | | | | | | | | |
|---|---|---|---|---|---|---|---|---|---|---|---|---|
| ccg | agc | cag | cag | ggc | aga | gtg | aga | aac | ctt | aga | gag aag ttc cag | 4315 |

-continued

| | | | | | | | | | | | | |
|---|---|---|---|---|---|---|---|---|---|---|---|---|
| Pro | Ser | Gln | Gln | Gly | Arg | Val | Arg | Asn | Leu | Arg | Glu | Lys | Phe | Gln |
| 1320 | | | | | 1325 | | | | 1330 | | | |

```
gcc ttg aac tct gtc ggt tga tgctgactcc tggggaggg aggagtcatg     4366
Ala Leu Asn Ser Val Gly
1335              1340 ttggaggttg gggaagaacc tgggcatcct tcccctcaag cctgggctca tggagcccct   4426
gcccagggcc ctcaggtggg cggaaagtcc atccctccg ccttcagga aggatgctcc     4486 cgtgtgcagg ggtctcctgc ctgtgccatc cactgggct cgagacaatt tcccactcac    4546
ctgtgaggcc ggtgtggctg cttcccttgt aaatagttgt tctctggtaa gaagccaaat  4606
atttaagctc acttcttccc agagagagga agctctgctc aggcctccag cgttggctgg   4666
ccatggccac agccagatgg aggagcccat ccccaggaga ctcaggcagt ggcctggaga  4726
ggctttgttc tgtaacggtg cctttttctta gggtccaggc aggaatgaag ccaataattt  4786
attgctttcc attctgtggt atgatgtgcg tgtgcgtgag tgtgtggccc ctgtttattc    4846
ccctcctgtc aagaatgaag tggattcagt tcaggtactt ttgaggggttg ttgtgctgac   4906 cctgtggttg tcgctgatgt acacacattt cattatttgc caatggtgca ataaccactg    4966
ctgaccaacc c                                                        4977
```

<210> SEQ ID NO 2
<211> LENGTH: 1340
<212> TYPE: PRT
<213> ORGANISM: Homo sapiens

<400> SEQUENCE: 2

| | | | | | | | | | | | | | | |
|---|---|---|---|---|---|---|---|---|---|---|---|---|---|---|
| Met | Pro | Val | Ser | Thr | Ser | Leu | His | Gln | Asp | Gly | Ser | Gln | Glu | Arg | Pro |
| 1 | | | | 5 | | | | | 10 | | | | | 15 | |

| | | | | | | | | | | | | | | |
|---|---|---|---|---|---|---|---|---|---|---|---|---|---|---|
| Val | Ser | Leu | Thr | Ser | Thr | Thr | Ser | Ser | Gly | Ser | Ser | Cys | Asp | Ser |
| | | | 20 | | | | | 25 | | | | | 30 | |

| | | | | | | | | | | | | | |
|---|---|---|---|---|---|---|---|---|---|---|---|---|---|
| Arg | Ser | Ala | Met | Glu | Glu | Pro | Ser | Ser | Ser | Glu | Ala | Pro | Ala | Lys | Asn |
| | | | 35 | | | | | 40 | | | | | 45 | | |

| | | | | | | | | | | | | | |
|---|---|---|---|---|---|---|---|---|---|---|---|---|---|
| Gly | Ala | Gly | Ser | Leu | Arg | Ser | Arg | His | Leu | Pro | Asn | Ser | Asn | Asn | Asn |
| | | 50 | | | | | 55 | | | | | 60 | | | |

| | | | | | | | | | | | | | |
|---|---|---|---|---|---|---|---|---|---|---|---|---|---|
| Ser | Ser | Ser | Trp | Leu | Asn | Val | Lys | Gly | Pro | Leu | Ser | Pro | Phe | Asn | Ser |
| 65 | | | | 70 | | | | | 75 | | | | | 80 | |

| | | | | | | | | | | | | | | |
|---|---|---|---|---|---|---|---|---|---|---|---|---|---|---|
| Arg | Ala | Ala | Ala | Gly | Pro | Ala | His | His | Lys | Leu | Ser | Tyr | Leu | Gly | Arg |
| | | | | 85 | | | | | 90 | | | | | 95 | |

| | | | | | | | | | | | | | | |
|---|---|---|---|---|---|---|---|---|---|---|---|---|---|---|
| Val | Val | Arg | Glu | Ile | Val | Glu | Thr | Glu | Arg | Met | Tyr | Val | Gln | Asp | Leu |
| | | | | 100 | | | | | 105 | | | | | 110 | |

| | | | | | | | | | | | | | | |
|---|---|---|---|---|---|---|---|---|---|---|---|---|---|---|
| Arg | Ser | Ile | Val | Glu | Asp | Tyr | Leu | Leu | Lys | Ile | Ile | Asp | Thr | Pro | Gly |
| | | | 115 | | | | | 120 | | | | | 125 | | |

| | | | | | | | | | | | | | | |
|---|---|---|---|---|---|---|---|---|---|---|---|---|---|---|
| Leu | Leu | Lys | Pro | Glu | Gln | Val | Ser | Ala | Leu | Phe | Gly | Asn | Ile | Glu | Asn |
| | 130 | | | | | 135 | | | | | 140 | | | | |

| | | | | | | | | | | | | | | |
|---|---|---|---|---|---|---|---|---|---|---|---|---|---|---|
| Ile | Tyr | Ala | Leu | Asn | Ser | Gln | Leu | Leu | Arg | Asp | Leu | Asp | Ser | Cys | Asn |
| 145 | | | | | 150 | | | | | 155 | | | | | 160 |

| | | | | | | | | | | | | | | |
|---|---|---|---|---|---|---|---|---|---|---|---|---|---|---|
| Ser | Asp | Pro | Val | Ala | Val | Ala | Ser | Cys | Phe | Val | Glu | Arg | Ser | Gln | Glu |
| | | | 165 | | | | | 170 | | | | | 175 | | |

| | | | | | | | | | | | | | | |
|---|---|---|---|---|---|---|---|---|---|---|---|---|---|---|
| Phe | Asp | Ile | Tyr | Thr | Gln | Tyr | Cys | Asn | Asn | Tyr | Pro | Asn | Ser | Val | Ala |
| | | | 180 | | | | | 185 | | | | | 190 | | |

| | | | | | | | | | | | | | | |
|---|---|---|---|---|---|---|---|---|---|---|---|---|---|---|
| Ala | Leu | Thr | Glu | Cys | Met | Arg | Asp | Lys | Gln | Ala | Lys | Phe | Phe | Arg |
| | | | 195 | | | | | 200 | | | | | 205 | |

| | | | | | | | | | | | | | | |
|---|---|---|---|---|---|---|---|---|---|---|---|---|---|---|
| Asp | Arg | Gln | Glu | Leu | Leu | Gln | His | Ser | Leu | Pro | Leu | Gly | Ser | Tyr | Leu |
| | 210 | | | | | 215 | | | | | 220 | | | | |

| | | | | | | | | | | | | | | |
|---|---|---|---|---|---|---|---|---|---|---|---|---|---|---|
| Leu | Lys | Pro | Val | Gln | Arg | Ile | Leu | Lys | Tyr | His | Leu | Leu | Leu | Gln | Glu |

-continued

```
                225                 230                 235                 240
Ile Ala Lys His Phe Asp Glu Glu Asp Gly Phe Glu Val Val Glu
                    245                 250                 255

Asp Ala Ile Asp Thr Met Thr Cys Val Ala Trp Tyr Ile Asn Asp Met
                    260                 265                 270

Lys Arg Arg His Glu His Ala Val Arg Leu Gln Glu Ile Gln Ser Leu
                    275                 280                 285

Leu Ile Asn Trp Lys Gly Pro Asp Leu Thr Thr Tyr Gly Glu Leu Val
            290                 295                 300

Leu Glu Gly Thr Phe Arg Val His Arg Val Arg Asn Glu Arg Thr Phe
305                 310                 315                 320

Phe Leu Phe Asp Lys Thr Leu Leu Ile Thr Lys Lys Arg Gly Asp His
                    325                 330                 335

Phe Val Tyr Lys Gly Asn Ile Pro Cys Ser Ser Leu Met Leu Ile Glu
                    340                 345                 350

Ser Thr Arg Asp Ser Leu Cys Phe Thr Val Thr His Tyr Lys His Ser
                    355                 360                 365

Lys Gln Gln Tyr Ser Ile Gln Ala Lys Thr Val Glu Glu Lys Arg Asn
            370                 375                 380

Trp Thr His His Ile Lys Arg Leu Ile Leu Glu Asn His His Ala Thr
385                 390                 395                 400

Ile Pro Gln Lys Ala Lys Glu Ala Ile Leu Glu Met Asp Ser Tyr Tyr
                    405                 410                 415

Pro Asn Arg Tyr Arg Cys Ser Pro Glu Arg Leu Lys Lys Ala Trp Ser
                    420                 425                 430

Ser Gln Asp Glu Val Ser Thr Asn Val Arg Gln Gly Arg Arg Gln Ser
                    435                 440                 445

Glu Pro Thr Lys His Leu Leu Arg Gln Leu Asn Glu Lys Ala Arg Ala
            450                 455                 460

Ala Gly Met Lys His Ala Gly Ser Ala Gly Thr Leu Leu Asp Phe Gly
465                 470                 475                 480

Gln Pro Ser Arg Thr Arg Gly Leu Gln Pro Glu Ala Glu Gly Ala Thr
                    485                 490                 495

Gln Glu Glu Glu Glu Glu Glu Glu Val Val Glu Glu Glu Glu Glu
                    500                 505                 510

Glu Glu Glu Glu Glu Gln Ala Phe Gln Val Ser Leu Glu Asp Leu Thr
            515                 520                 525

Gly His Glu Gly Asn Lys Gly Ala Gly Pro Glu Pro Gly Ser
530                 535                 540

Glu Glu Glu Glu Glu Glu Gln Glu Glu Ser Leu Ala Val Ala Glu Gln
545                 550                 555                 560

Val Ala Asp Phe Ala Ser Ser Leu Leu Ala Ala Leu His Cys Trp His
                    565                 570                 575

Tyr Arg Ala Asn Ala Leu Leu Phe Ser Arg Gly Ala Met Gly Lys Gly
                    580                 585                 590

Arg Arg Glu Ser Glu Ser Ser Arg Ser Arg Pro Ser Gly Arg
                    595                 600                 605

Ser Pro Thr Ser Thr Glu Lys Arg Met Ser Phe Glu Ser Ile Ser Ser
            610                 615                 620

Leu Pro Glu Val Glu Pro Asp Pro Glu Ala Gly Ser Glu Gln Glu Val
625                 630                 635                 640

Phe Ser Ala Val Glu Gly Pro Ser Ala Glu Glu Thr Pro Ser Asp Thr
                    645                 650                 655
```

-continued

Glu Ser Pro Glu Val Leu Glu Thr Gln Leu Asp Ala His Gln Gly Leu
            660                 665                 670

Leu Gly Met Asp Pro Pro Gly Met Val Asp Phe Val Ala Ala Glu
        675                 680                 685

Ser Thr Glu Asp Leu Lys Ala Leu Ser Ser Glu Glu Glu Glu Met
690                 695                 700

Gly Gly Ala Ala Gln Glu Pro Glu Ser Leu Leu Pro Pro Ser Val Leu
705                 710                 715                 720

Asp Gln Ala Ser Val Ile Ala Glu Arg Phe Val Ser Phe Ser Arg
                725                 730                 735

Arg Ser Ser Val Ala Gln Glu Asp Ser Lys Ser Ser Gly Phe Gly Ser
                740                 745                 750

Pro Arg Leu Val Ser Arg Ser Ser Val Leu Ser Leu Glu Gly Ser
            755                 760                 765

Glu Lys Gly Leu Ala Arg His Gly Ser Ala Thr Asp Ser Leu Ser Cys
770                 775                 780

Gln Leu Ser Pro Glu Val Asp Ile Ser Val Gly Val Ala Thr Glu Asp
785                 790                 795                 800

Ser Pro Ser Val Asn Gly Met Glu Pro Ser Pro Gly Cys Pro Val
            805                 810                 815

Glu Pro Asp Arg Ser Ser Cys Lys Lys Lys Glu Ser Ala Leu Ser Thr
                820                 825                 830

Arg Asp Arg Leu Leu Leu Asp Lys Ile Lys Ser Tyr Tyr Glu Asn Ala
                835                 840                 845

Glu His His Asp Ala Gly Phe Ser Val Arg Arg Arg Glu Ser Leu Ser
            850                 855                 860

Tyr Ile Pro Lys Gly Leu Val Arg Asn Ser Ile Ser Arg Phe Asn Ser
865                 870                 875                 880

Leu Pro Arg Pro Asp Pro Glu Pro Val Pro Pro Val Gly Ser Lys Arg
                885                 890                 895

Gln Val Gly Ser Arg Pro Thr Ser Trp Ala Leu Phe Glu Leu Pro Gly
            900                 905                 910

Pro Ser Gln Ala Val Lys Gly Asp Pro Pro Pro Ile Ser Asp Ala Glu
            915                 920                 925

Phe Arg Pro Ser Ser Glu Ile Val Lys Ile Trp Glu Gly Met Glu Ser
930                 935                 940

Ser Gly Gly Ser Pro Gly Lys Gly Pro Gly Gln Gly Gln Ala Asn Gly
945                 950                 955                 960

Phe Asp Leu His Glu Pro Leu Phe Ile Leu Glu His Glu Leu Gly
                965                 970                 975

Ala Ile Thr Glu Glu Ser Ala Thr Ala Ser Pro Glu Ser Ser Pro
            980                 985                 990

Thr Glu Gly Arg Ser Pro Ala His Leu Ala Arg Glu Leu Lys Glu Leu
            995                 1000                1005

Val Lys Glu Leu Ser Ser Ser Thr Gln Gly Glu Leu Val Ala Pro
        1010                1015                1020

Leu His Pro Arg Ile Val Gln Leu Ser His Val Met Asp Ser His
    1025                1030                1035

Val Ser Glu Arg Val Lys Asn Lys Val Tyr Gln Leu Ala Arg Gln
        1040                1045                1050

Tyr Ser Leu Arg Ile Lys Ser Asn Lys Pro Val Met Ala Arg Pro
    1055                1060                1065

Pro Leu Gln Trp Glu Lys Val Ala Pro Glu Arg Asp Gly Lys Ser
        1070                1075                1080

```
Pro Thr Val Pro Cys Leu Gln Glu Glu Ala Gly Glu Pro Leu Gly
    1085                1090                1095

Gly Lys Gly Lys Arg Lys Pro Val Leu Ser Leu Phe Asp Tyr Glu
    1100                1105                1110

Gln Leu Met Ala Gln Glu His Ser Pro Pro Lys Pro Ser Ser Ala
    1115                1120                1125

Gly Glu Met Ser Pro Gln Arg Phe Phe Phe Asn Pro Ser Ala Val
    1130                1135                1140

Ser Gln Arg Thr Thr Ser Pro Gly Gly Arg Pro Ser Ala Trp Ser
    1145                1150                1155

Pro Leu Ser Pro Thr Glu Thr Phe Ser Trp Pro Asp Val Arg Glu
    1160                1165                1170

Leu Cys Ser Lys Tyr Ala Ser Arg Asp Glu Ala Arg Arg Ala Gly
    1175                1180                1185

Gly Gly Arg Pro Arg Gly Pro Pro Val Asn Arg Ser His Ser Val
    1190                1195                1200

Pro Glu Asn Met Val Glu Pro Pro Leu Ser Gly Arg Val Gly Arg
    1205                1210                1215

Cys Arg Ser Leu Ser Thr Lys Arg Gly Arg Gly Gly Glu Ala
    1220                1225                1230

Ala Gln Ser Pro Gly Pro Leu Pro Gln Ser Lys Pro Asp Gly Gly
    1235                1240                1245

Glu Thr Leu Tyr Val Thr Ala Asp Leu Thr Leu Glu Asp Asn Arg
    1250                1255                1260

Arg Val Ile Val Met Glu Lys Gly Pro Leu Pro Ser Pro Thr Ala
    1265                1270                1275

Gly Leu Glu Glu Ser Ser Gly Gln Gly Pro Ser Ser Pro Val Ala
    1280                1285                1290

Leu Leu Gly Gln Val Gln Asp Phe Gln Gln Ser Ala Glu Cys Gln
    1295                1300                1305

Pro Lys Glu Glu Gly Ser Arg Asp Pro Ala Asp Pro Ser Gln Gln
    1310                1315                1320

Gly Arg Val Arg Asn Leu Arg Glu Lys Phe Gln Ala Leu Asn Ser
    1325                1330                1335

Val Gly
    1340

<210> SEQ ID NO 3
<211> LENGTH: 1095
<212> TYPE: DNA
<213> ORGANISM: Homo sapiens
<220> FEATURE:
<221> NAME/KEY: misc_feature
<223> OTHER INFORMATION: A partial sequence of SEQ ID NO:1 consisting of
      the 581st to the 1675th nucleotides that comprises a region
      encoding Dbl homology domain and Pleckstrin homology domain, which
      encodes the amino acid sequence of SEQ ID NO:4.
<220> FEATURE:
<221> NAME/KEY: CDS
<222> LOCATION: (1)..(1095)

<400> SEQUENCE: 3 aag ctc agc tac ctg ggc cga gtg gtg cgg gag atc gtg gag aca gag    48
Lys Leu Ser Tyr Leu Gly Arg Val Val Arg Glu Ile Val Glu Thr Glu
1               5                   10                  15 cgc atg tac gta cag gac ctg cgc agc atc gtg gag gac tac ctc ttg    96
Arg Met Tyr Val Gln Asp Leu Arg Ser Ile Val Glu Asp Tyr Leu Leu
            20                  25                  30
```

| | | |
|---|---|---|
| aag atc att gac aca ccc ggg ctg ctg aag cca gaa cag gtc agc gcc<br>Lys Ile Ile Asp Thr Pro Gly Leu Leu Lys Pro Glu Gln Val Ser Ala<br>35          40                  45 | | 144 |
| ctc ttt ggg aac ata gaa aac atc tac gcg ctg aac agc cag ctc ctc<br>Leu Phe Gly Asn Ile Glu Asn Ile Tyr Ala Leu Asn Ser Gln Leu Leu<br>50              55              60 | | 192 |
| aga gac ctg gac agc tgc aat agt gac ccc gtg gct gtg gcc agc tgc<br>Arg Asp Leu Asp Ser Cys Asn Ser Asp Pro Val Ala Val Ala Ser Cys<br>65              70              75              80 | | 240 |
| ttt gtg gaa agg agc caa gag ttt gat atc tac act cag tat tgc aac<br>Phe Val Glu Arg Ser Gln Glu Phe Asp Ile Tyr Thr Gln Tyr Cys Asn<br>          85              90              95 | | 288 |
| aat tac ccc aac tcc gtg gcc gcc ctg acg gaa tgc atg cgg gac aag<br>Asn Tyr Pro Asn Ser Val Ala Ala Leu Thr Glu Cys Met Arg Asp Lys<br>      100             105             110 | | 336 |
| cag cag gcc aag ttc ttt cgg gac cgg cag gag cta cta cag cac tcg<br>Gln Gln Ala Lys Phe Phe Arg Asp Arg Gln Glu Leu Leu Gln His Ser<br>      115             120             125 | | 384 |
| ctg ccc ttg ggc tcc tac ctg ctg aag cca gtc cag cgc atc ctc aag<br>Leu Pro Leu Gly Ser Tyr Leu Leu Lys Pro Val Gln Arg Ile Leu Lys<br>130             135             140 | | 432 |
| tac cac ctg ctg ctc cag gaa att gcc aaa cat ttt gat gaa gaa gag<br>Tyr His Leu Leu Leu Gln Glu Ile Ala Lys His Phe Asp Glu Glu Glu<br>145             150             155             160 | | 480 |
| gat ggc ttt gag gtg gtg gag gat gcc att gac acc atg acc tgt gtg<br>Asp Gly Phe Glu Val Val Glu Asp Ala Ile Asp Thr Met Thr Cys Val<br>              165             170             175 | | 528 |
| gcc tgg tac atc aac gac atg aag agg agg cat gag cac gcg gtc cgg<br>Ala Trp Tyr Ile Asn Asp Met Lys Arg Arg His Glu His Ala Val Arg<br>          180             185             190 | | 576 |
| ctc cag gag att cag tca ctc ctc atc aac tgg aag ggg ccc gac ctg<br>Leu Gln Glu Ile Gln Ser Leu Leu Ile Asn Trp Lys Gly Pro Asp Leu<br>      195             200             205 | | 624 |
| acc acc tac ggg gag ctt gtc ctg gag ggc aca ttc cgc gtg cat cgc<br>Thr Thr Tyr Gly Glu Leu Val Leu Glu Gly Thr Phe Arg Val His Arg<br>210             215             220 | | 672 |
| gtg cgc aat gaa agg acc ttt ttc ctc ttt gac aaa aca ctg ctt atc<br>Val Arg Asn Glu Arg Thr Phe Phe Leu Phe Asp Lys Thr Leu Leu Ile<br>225             230             235             240 | | 720 |
| acc aag aag cgg ggc gat cac ttt gtc tac aag ggc aac atc ccg tgc<br>Thr Lys Lys Arg Gly Asp His Phe Val Tyr Lys Gly Asn Ile Pro Cys<br>              245             250             255 | | 768 |
| tcc tcc ctg atg ctg atc gaa agc acc aga gac tcc ctg tgc ttc act<br>Ser Ser Leu Met Leu Ile Glu Ser Thr Arg Asp Ser Leu Cys Phe Thr<br>          260             265             270 | | 816 |
| gtc acc cac tac aag cac agc aag cag cag tac agc atc cag gcc aag<br>Val Thr His Tyr Lys His Ser Lys Gln Gln Tyr Ser Ile Gln Ala Lys<br>      275             280             285 | | 864 |
| aca gtg gag gag aaa cgg aac tgg act cac cac atc aag agg ctc atc<br>Thr Val Glu Glu Lys Arg Asn Trp Thr His His Ile Lys Arg Leu Ile<br>      290             295             300 | | 912 |
| cta gag aac cac cat gcc acc att ccc cag aag gcc aag gaa gcc atc<br>Leu Glu Asn His His Ala Thr Ile Pro Gln Lys Ala Lys Glu Ala Ile<br>305             310             315             320 | | 960 |
| ttg gaa atg gat tcc tat tat ccc aat cgg tac cgc tgc agc cca gag<br>Leu Glu Met Asp Ser Tyr Tyr Pro Asn Arg Tyr Arg Cys Ser Pro Glu<br>              325             330             335 | | 1008 |
| cgg ctg aag aag gct tgg tcc tcc cag gat gag gtg tcc acc aat gtg<br>Arg Leu Lys Lys Ala Trp Ser Ser Gln Asp Glu Val Ser Thr Asn Val<br>          340             345             350 | | 1056 |

```
cgc cag ggg cgc cgg caa tct gag cca acc aaa cac ctg                  1095
Arg Gln Gly Arg Arg Gln Ser Glu Pro Thr Lys His Leu
        355                 360                 365

<210> SEQ ID NO 4
<211> LENGTH: 365
<212> TYPE: PRT
<213> ORGANISM: Homo sapiens

<400> SEQUENCE: 4

Lys Leu Ser Tyr Leu Gly Arg Val Val Arg Glu Ile Val Glu Thr Glu
1               5                   10                  15

Arg Met Tyr Val Gln Asp Leu Arg Ser Ile Val Glu Asp Tyr Leu Leu
            20                  25                  30

Lys Ile Ile Asp Thr Pro Gly Leu Leu Lys Pro Glu Gln Val Ser Ala
        35                  40                  45

Leu Phe Gly Asn Ile Glu Asn Ile Tyr Ala Leu Asn Ser Gln Leu Leu
    50                  55                  60

Arg Asp Leu Asp Ser Cys Asn Ser Asp Pro Val Ala Val Ala Ser Cys
65                  70                  75                  80

Phe Val Glu Arg Ser Gln Glu Phe Asp Ile Tyr Thr Gln Tyr Cys Asn
                85                  90                  95

Asn Tyr Pro Asn Ser Val Ala Ala Leu Thr Glu Cys Met Arg Asp Lys
            100                 105                 110

Gln Gln Ala Lys Phe Phe Arg Asp Arg Gln Glu Leu Leu Gln His Ser
        115                 120                 125

Leu Pro Leu Gly Ser Tyr Leu Leu Lys Pro Val Gln Arg Ile Leu Lys
    130                 135                 140

Tyr His Leu Leu Leu Gln Glu Ile Ala Lys His Phe Asp Glu Glu Glu
145                 150                 155                 160

Asp Gly Phe Glu Val Val Glu Asp Ala Ile Asp Thr Met Thr Cys Val
                165                 170                 175

Ala Trp Tyr Ile Asn Asp Met Lys Arg Arg His Glu His Ala Val Arg
            180                 185                 190

Leu Gln Glu Ile Gln Ser Leu Leu Ile Asn Trp Lys Gly Pro Asp Leu
        195                 200                 205

Thr Thr Tyr Gly Glu Leu Val Leu Glu Gly Thr Phe Arg Val His Arg
    210                 215                 220

Val Arg Asn Glu Arg Thr Phe Phe Leu Phe Asp Lys Thr Leu Leu Ile
225                 230                 235                 240

Thr Lys Lys Arg Gly Asp His Phe Val Tyr Lys Gly Asn Ile Pro Cys
                245                 250                 255

Ser Ser Leu Met Leu Ile Glu Ser Thr Arg Asp Ser Leu Cys Phe Thr
            260                 265                 270

Val Thr His Tyr Lys His Ser Lys Gln Gln Tyr Ser Ile Gln Ala Lys
        275                 280                 285

Thr Val Glu Glu Lys Arg Asn Trp Thr His His Ile Lys Arg Leu Ile
    290                 295                 300

Leu Glu Asn His His Ala Thr Ile Pro Gln Lys Ala Lys Glu Ala Ile
305                 310                 315                 320

Leu Glu Met Asp Ser Tyr Tyr Pro Asn Arg Tyr Arg Cys Ser Pro Glu
                325                 330                 335

Arg Leu Lys Lys Ala Trp Ser Ser Gln Asp Glu Val Ser Thr Asn Val
            340                 345                 350

Arg Gln Gly Arg Arg Gln Ser Glu Pro Thr Lys His Leu
        355                 360                 365
```

```
<210> SEQ ID NO 5
<211> LENGTH: 1102
<212> TYPE: DNA
<213> ORGANISM: Homo sapiens
<220> FEATURE:
<221> NAME/KEY: misc_feature
<223> OTHER INFORMATION: Polynucleotide having kozak consensus sequence
      and methionine codon in its 5'-terminal, followed by partial
      sequence of SEQ ID NO:1.
<220> FEATURE:
<221> NAME/KEY: CDS
<222> LOCATION: (5)..(1102)
<220> FEATURE:
<221> NAME/KEY: misc_feature
<222> LOCATION: (1)..(4)
<223> OTHER INFORMATION: kozak consensus sequence
<220> FEATURE:
<221> NAME/KEY: misc_feature
<222> LOCATION: (5)..(7)
<223> OTHER INFORMATION: methionine codon

<400> SEQUENCE: 5 cacc atg aag ctc agc tac ctg ggc cga gtg gtg cgg gag atc gtg gag      49
     Met Lys Leu Ser Tyr Leu Gly Arg Val Val Arg Glu Ile Val Glu
     1               5                   10                  15 aca gag cgc atg tac gta cag gac ctg cgc agc atc gtg gag gac tac       97
Thr Glu Arg Met Tyr Val Gln Asp Leu Arg Ser Ile Val Glu Asp Tyr
                 20                  25                  30 ctc ttg aag atc att gac aca ccc ggg ctg ctg aag cca gaa cag gtc      145
Leu Leu Lys Ile Ile Asp Thr Pro Gly Leu Leu Lys Pro Glu Gln Val
             35                  40                  45 agc gcc ctc ttt ggg aac ata gaa aac atc tac gcg ctg aac agc cag      193
Ser Ala Leu Phe Gly Asn Ile Glu Asn Ile Tyr Ala Leu Asn Ser Gln
         50                  55                  60 ctc ctc aga gac ctg gac agc tgc aat agt gac ccc gtg gct gtg gcc      241
Leu Leu Arg Asp Leu Asp Ser Cys Asn Ser Asp Pro Val Ala Val Ala
     65                  70                  75 agc tgc ttt gtg gaa agg agc caa gag ttt gat atc tac act cag tat      289
Ser Cys Phe Val Glu Arg Ser Gln Glu Phe Asp Ile Tyr Thr Gln Tyr
80                  85                  90                  95 tgc aac aat tac ccc aac tcc gtg gcc gcc ctg acg gaa tgc atg cgg      337
Cys Asn Asn Tyr Pro Asn Ser Val Ala Ala Leu Thr Glu Cys Met Arg
                100                 105                 110 gac aag cag cag gcc aag ttc ttt cgg gac cgg cag gag ctg cta cag      385
Asp Lys Gln Gln Ala Lys Phe Phe Arg Asp Arg Gln Glu Leu Leu Gln
            115                 120                 125 cac tcg ctg ccc ttg ggc tcc tac ctg ctg aag cca gtc cag cgc atc      433
His Ser Leu Pro Leu Gly Ser Tyr Leu Leu Lys Pro Val Gln Arg Ile
        130                 135                 140 ctc aag tac cac ctg ctg ctc cag gaa att gcc aaa cat ttt gat gaa      481
Leu Lys Tyr His Leu Leu Leu Gln Glu Ile Ala Lys His Phe Asp Glu
    145                 150                 155 gaa gag gat ggc ttt gag gtg gtg gag gat gcc att gac acc atg acc      529
Glu Glu Asp Gly Phe Glu Val Val Glu Asp Ala Ile Asp Thr Met Thr
160                 165                 170                 175 tgt gtg gcc tgg tac atc aac gac atg aag agg agg cat gag cac gcg      577
Cys Val Ala Trp Tyr Ile Asn Asp Met Lys Arg Arg His Glu His Ala
                180                 185                 190 gtc cgg ctc cag gag att cag tca ctc ctc atc aac tgg aag ggg ccc      625
Val Arg Leu Gln Glu Ile Gln Ser Leu Leu Ile Asn Trp Lys Gly Pro
            195                 200                 205 gac ctg acc acc tac ggg gag ctt gtc ctg gag ggc aca ttc cgc gtg      673
Asp Leu Thr Thr Tyr Gly Glu Leu Val Leu Glu Gly Thr Phe Arg Val
        210                 215                 220
```

```
cat cgc gtg cgc aat gaa agg acc ttt ttc ctc ttt gac aaa aca ctg    721
His Arg Val Arg Asn Glu Arg Thr Phe Phe Leu Phe Asp Lys Thr Leu
    225                 230                 235 ctt atc acc aag aag cgg ggc gat cac ttt gtc tac aag ggc aac atc    769
Leu Ile Thr Lys Lys Arg Gly Asp His Phe Val Tyr Lys Gly Asn Ile
240                 245                 250                 255 ccg tgc tcc tcc ctg atg ctg atc gaa agc acc aga gac tcc ctg tgc    817
Pro Cys Ser Ser Leu Met Leu Ile Glu Ser Thr Arg Asp Ser Leu Cys
                260                 265                 270 ttc act gtc acc cac tac aag cac agc aag cag cag tac agc atc cag    865
Phe Thr Val Thr His Tyr Lys His Ser Lys Gln Gln Tyr Ser Ile Gln
            275                 280                 285 gcc aag aca gtg gag gag aaa cgg aac tgg act cac cac atc aag agg    913
Ala Lys Thr Val Glu Glu Lys Arg Asn Trp Thr His His Ile Lys Arg
        290                 295                 300 ctc atc cta gag aac cac cat gcc acc att ccc cag aag gcc aag gaa    961
Leu Ile Leu Glu Asn His His Ala Thr Ile Pro Gln Lys Ala Lys Glu
    305                 310                 315 gcc atc ttg gaa atg gat tcc tat tat ccc aat cgg tac cgc tgc agc   1009
Ala Ile Leu Glu Met Asp Ser Tyr Tyr Pro Asn Arg Tyr Arg Cys Ser
320                 325                 330                 335 cca gag cgg ctg aag aag gct tgg tcc tcc cag gat gag gtg tcc acc   1057
Pro Glu Arg Leu Lys Lys Ala Trp Ser Ser Gln Asp Glu Val Ser Thr
                340                 345                 350 aat gtg cgc cag ggg cgc cgg caa tct gag cca acc aaa cac ctg       1102
Asn Val Arg Gln Gly Arg Arg Gln Ser Glu Pro Thr Lys His Leu
            355                 360                 365

<210> SEQ ID NO 6
<211> LENGTH: 366
<212> TYPE: PRT
<213> ORGANISM: Homo sapiens

<400> SEQUENCE: 6

Met Lys Leu Ser Tyr Leu Gly Arg Val Val Arg Glu Ile Val Glu Thr
1               5                   10                  15

Glu Arg Met Tyr Val Gln Asp Leu Arg Ser Ile Val Glu Asp Tyr Leu
            20                  25                  30

Leu Lys Ile Ile Asp Thr Pro Gly Leu Leu Lys Pro Glu Gln Val Ser
        35                  40                  45

Ala Leu Phe Gly Asn Ile Glu Asn Ile Tyr Ala Leu Asn Ser Gln Leu
    50                  55                  60

Leu Arg Asp Leu Asp Ser Cys Asn Ser Asp Pro Val Ala Val Ala Ser
65                  70                  75                  80

Cys Phe Val Glu Arg Ser Gln Glu Phe Asp Ile Tyr Thr Gln Tyr Cys
                85                  90                  95

Asn Asn Tyr Pro Asn Ser Val Ala Ala Leu Thr Glu Cys Met Arg Asp
            100                 105                 110

Lys Gln Gln Ala Lys Phe Phe Arg Asp Arg Gln Glu Leu Leu Gln His
        115                 120                 125

Ser Leu Pro Leu Gly Ser Tyr Leu Leu Lys Pro Val Gln Arg Ile Leu
    130                 135                 140

Lys Tyr His Leu Leu Leu Gln Glu Ile Ala Lys His Phe Asp Glu Glu
145                 150                 155                 160

Glu Asp Gly Phe Glu Val Val Glu Asp Ala Ile Asp Thr Met Thr Cys
                165                 170                 175

Val Ala Trp Tyr Ile Asn Asp Met Lys Arg Arg His Glu His Ala Val
            180                 185                 190
```

Arg Leu Gln Glu Ile Gln Ser Leu Leu Ile Asn Trp Lys Gly Pro Asp
                195                 200                 205

Leu Thr Thr Tyr Gly Glu Leu Val Leu Glu Gly Thr Phe Arg Val His
        210                 215                 220

Arg Val Arg Asn Glu Arg Thr Phe Phe Leu Phe Asp Lys Thr Leu Leu
225                 230                 235                 240

Ile Thr Lys Lys Arg Gly Asp His Phe Val Tyr Lys Gly Asn Ile Pro
                245                 250                 255

Cys Ser Ser Leu Met Leu Ile Glu Ser Thr Arg Asp Ser Leu Cys Phe
                260                 265                 270

Thr Val Thr His Tyr Lys His Ser Lys Gln Gln Tyr Ser Ile Gln Ala
            275                 280                 285

Lys Thr Val Glu Glu Lys Arg Asn Trp Thr His Ile Lys Arg Leu
        290                 295                 300

Ile Leu Glu Asn His His Ala Thr Ile Pro Gln Lys Ala Lys Glu Ala
305                 310                 315                 320

Ile Leu Glu Met Asp Ser Tyr Tyr Pro Asn Arg Tyr Arg Cys Ser Pro
                325                 330                 335

Glu Arg Leu Lys Lys Ala Trp Ser Ser Gln Asp Glu Val Ser Thr Asn
                340                 345                 350

Val Arg Gln Gly Arg Arg Gln Ser Glu Pro Thr Lys His Leu
            355                 360                 365

<210> SEQ ID NO 7
<211> LENGTH: 22
<212> TYPE: DNA
<213> ORGANISM: Artificial
<220> FEATURE:
<223> OTHER INFORMATION: Designed polynucleotide based on the sequence
      of SEQ ID NO:1 for use as a primer

<400> SEQUENCE: 7
gggagatgtc accacagcgt tt                                          22

<210> SEQ ID NO 8
<211> LENGTH: 29
<212> TYPE: DNA
<213> ORGANISM: Artificial
<220> FEATURE:
<223> OTHER INFORMATION: Designed polynucleotide based on the sequence
      of SEQ ID NO:1 for use as a primer

<400> SEQUENCE: 8
aatggatccc gaccgacaga gttcaaggc                                   29

<210> SEQ ID NO 9
<211> LENGTH: 34
<212> TYPE: DNA
<213> ORGANISM: Artificial
<220> FEATURE:
<223> OTHER INFORMATION: Designed polynucleotide based on the sequence
      of SEQ ID NO:1 for use as a primer

<400> SEQUENCE: 9
caccatgaag ctcagctacc tgggccgagt ggtg                             34

<210> SEQ ID NO 10
<211> LENGTH: 26
<212> TYPE: DNA
<213> ORGANISM: Artificial
<220> FEATURE:
<223> OTHER INFORMATION: Designed polynucleotide based on the sequence of SEQ ID NO:1 for use as a primer

<400> SEQUENCE: 10
caggtgtttg gttggctcag attgcc                                                  26

<210> SEQ ID NO 11
<211> LENGTH: 35
<212> TYPE: DNA
<213> ORGANISM: Artificial
<220> FEATURE:
<223> OTHER INFORMATION: Designed polynucleotide based on the sequence
      of proto-Dbl for use as a primer

<400> SEQUENCE: 11
aatagatctg gaaatggcag ttttaaagaa ccacg                                        35

<210> SEQ ID NO 12
<211> LENGTH: 29
<212> TYPE: DNA
<213> ORGANISM: Artificial
<220> FEATURE:
<223> OTHER INFORMATION: Designed polynucleotide based on the sequence
      of proto-Dbl for use as a primer

<400> SEQUENCE: 12
aatgtcgacc tgcttcaaca aaatatttc                                               29

<210> SEQ ID NO 13
<211> LENGTH: 29
<212> TYPE: DNA
<213> ORGANISM: Artificial
<220> FEATURE:
<223> OTHER INFORMATION: Designed polynucleotide based on the sequence
      of Cdc42 for use as a primer

<400> SEQUENCE: 13
caccatgcag acaattaagt gtgttgttg                                               29

<210> SEQ ID NO 14
<211> LENGTH: 25
<212> TYPE: DNA
<213> ORGANISM: Artificial
<220> FEATURE:
<223> OTHER INFORMATION: Designed polynucleotide based on the sequence
      of Cdc42 for use as a primer

<400> SEQUENCE: 14
tcatagcagc acacacctgc ggctc                                                   25

<210> SEQ ID NO 15
<211> LENGTH: 29
<212> TYPE: DNA
<213> ORGANISM: Artificial
<220> FEATURE:
<223> OTHER INFORMATION: Designed polynucleotide based on the sequence
      of RhoA for use as a primer

<400> SEQUENCE: 15
caccatggct gccatccgga agaaactgg                                               29

<210> SEQ ID NO 16
<211> LENGTH: 28
<212> TYPE: DNA
<213> ORGANISM: Artificial
<220> FEATURE:
<223> OTHER INFORMATION: Designed polynucleotide based on the sequence
      of RhoA for use as a primer

```
<400> SEQUENCE: 16
tcacaagaca aggcaaccag attttttc                                          28

<210> SEQ ID NO 17
<211> LENGTH: 29
<212> TYPE: DNA
<213> ORGANISM: Artificial
<220> FEATURE:
<223> OTHER INFORMATION: Designed polynucleotide based on the sequence
      of Rac1 for use as a primer

<400> SEQUENCE: 17
caccatgcag gccatcaagt gtgtggtgg                                         29

<210> SEQ ID NO 18
<211> LENGTH: 26
<212> TYPE: DNA
<213> ORGANISM: Artificial
<220> FEATURE:
<223> OTHER INFORMATION: Designed polynucleotide based on the sequence
      of Rac1 for use as a primer

<400> SEQUENCE: 18
ttacaacagc aggcattttc tcttcc                                            26

<210> SEQ ID NO 19
<211> LENGTH: 7
<212> TYPE: DNA
<213> ORGANISM: artificial
<220> FEATURE:
<223> OTHER INFORMATION: Designed oligonucleotide including Kozak
      consensus sequence followed by a methionine codon.

<400> SEQUENCE: 19 caccatg                                                                 7

<210> SEQ ID NO 20
<211> LENGTH: 576
<212> TYPE: DNA
<213> ORGANISM: homo sapiens
<220> FEATURE:
<221> NAME/KEY: misc_feature
<223> OTHER INFORMATION: Cdc42 gene

<400> SEQUENCE: 20
atgcagacaa ttaagtgtgt tgttgtgggc gatggtgctg ttggtaaaac atgtctcctg       60
atatcctaca caacaaacaa atttccatcg gaatatgtac cgactgtttt tgacaactat     120
gcagtcacag ttatgattgg tggagaacca tatactcttg gacttttga tactgcaggg      180 caagaggatt atgacagatt acgaccgctg agttatccac aaacagatgt atttctagtc    240 tgttttcag tggtctctcc atcttcattt gaaaacgtga agaaaagtg ggtgcctgag      300 ataactcacc actgtccaaa gactccttc ttgcttgttg ggactcaaat tgatctcaga     360
gatgacccct ctactattga gaaacttgcc aagaacaaac agaagcctat cactccagag    420
actgctgaaa agctggcccg tgacctgaag gctgtcaagt atgtggagtg ttctgcactt    480
acacagaaag gcctaaagaa tgtatttgac gaagcaatat tggctgccct ggagcctcca    540
gaaccgaaga gagccgcag gtgtgtgctg ctatga                               576

<210> SEQ ID NO 21
<211> LENGTH: 191
<212> TYPE: PRT
<213> ORGANISM: homo sapiens
<220> FEATURE:
```

<221> NAME/KEY: misc_feature
<223> OTHER INFORMATION: Cdc42

<400> SEQUENCE: 21

```
Met Gln Thr Ile Lys Cys Val Val Gly Asp Gly Ala Val Gly Lys
1               5                   10                  15

Thr Cys Leu Leu Ile Ser Tyr Thr Thr Asn Lys Phe Pro Ser Glu Tyr
            20                  25                  30

Val Pro Thr Val Phe Asp Asn Tyr Ala Val Thr Val Met Ile Gly Gly
            35                  40                  45

Glu Pro Tyr Thr Leu Gly Leu Phe Asp Thr Ala Gly Gln Glu Asp Tyr
    50                  55                  60

Asp Arg Leu Arg Pro Leu Ser Tyr Pro Gln Thr Asp Val Phe Leu Val
65                  70                  75                  80

Cys Phe Ser Val Val Ser Pro Ser Ser Phe Glu Asn Val Lys Glu Lys
                85                  90                  95

Trp Val Pro Glu Ile Thr His His Cys Pro Lys Thr Pro Phe Leu Leu
                100                 105                 110

Val Gly Thr Gln Ile Asp Leu Arg Asp Asp Pro Ser Thr Ile Glu Lys
            115                 120                 125

Leu Ala Lys Asn Lys Gln Lys Pro Ile Thr Pro Glu Thr Ala Glu Lys
    130                 135                 140

Leu Ala Arg Asp Leu Lys Ala Val Lys Tyr Val Glu Cys Ser Ala Leu
145                 150                 155                 160

Thr Gln Lys Gly Leu Lys Asn Val Phe Asp Glu Ala Ile Leu Ala Ala
                165                 170                 175

Leu Glu Pro Pro Glu Pro Lys Lys Ser Arg Arg Cys Val Leu Leu
                180                 185                 190
```

<210> SEQ ID NO 22
<211> LENGTH: 582
<212> TYPE: DNA
<213> ORGANISM: homo sapiens
<220> FEATURE:
<221> NAME/KEY: misc_feature
<223> OTHER INFORMATION: RhoA gene

<400> SEQUENCE: 22

| | | | | | |
|---|---|---|---|---|---|
| atggctgcca | tccggaagaa | actggtgatt | gttggtgatg | agcctgtgg | aaagacatgc | 60 |
| ttgctcatag | tcttcagcaa | ggaccagttc | ccagaggtgt | atgtgcccac | agtgtttgag | 120 |
| aactatgtgg | cagatatcga | ggtggatgga | aagcaggtag | agttggcttt | gtgggacaca | 180 |
| gctgggcagg | aagattatga | tcgcctgagg | cccctctcct | acccagatac | cgatgttata | 240 |
| ctgatgtgtt | tttccatcga | cagccctgat | agtttagaaa | acatcccaga | aaagtggacc | 300 |
| ccagaagtca | gcatttctg | tcccaacgtg | cccatcatcc | tggttgggaa | taagaaggat | 360 |
| cttcggaatg | atgagcacac | aaggcgggag | ctagccaaga | tgaagcagga | gccggtgaaa | 420 |
| cctgaagaag | gcagagatat | ggcaaacagg | attggcgctt | ttgggtacat | ggagtgttca | 480 |
| gcaaagacca | agatggagt | gagagaggtt | tttgaaatgg | ctacgagagc | tgctctgcaa | 540 |
| gctagacgtg | ggaagaaaaa | atctggttgc | cttgtcttgt | ga | | 582 |

<210> SEQ ID NO 23
<211> LENGTH: 193
<212> TYPE: PRT
<213> ORGANISM: homo sapiens
<220> FEATURE:
<221> NAME/KEY: misc_feature
<223> OTHER INFORMATION: RhoA

<400> SEQUENCE: 23

```
Met Ala Ala Ile Arg Lys Lys Leu Val Ile Val Gly Asp Gly Ala Cys
1               5                   10                  15

Gly Lys Thr Cys Leu Leu Ile Val Phe Ser Lys Asp Gln Phe Pro Glu
            20                  25                  30

Val Tyr Val Pro Thr Val Phe Glu Asn Tyr Val Ala Asp Ile Glu Val
        35                  40                  45

Asp Gly Lys Gln Val Glu Leu Ala Leu Trp Asp Thr Ala Gly Gln Glu
    50                  55                  60

Asp Tyr Asp Arg Leu Arg Pro Leu Ser Tyr Pro Asp Thr Asp Val Ile
65                  70                  75                  80

Leu Met Cys Phe Ser Ile Asp Ser Pro Asp Ser Leu Glu Asn Ile Pro
                85                  90                  95

Glu Lys Trp Thr Pro Glu Val Lys His Phe Cys Pro Asn Val Pro Ile
            100                 105                 110

Ile Leu Val Gly Asn Lys Lys Asp Leu Arg Asn Asp Glu His Thr Arg
        115                 120                 125

Arg Glu Leu Ala Lys Met Lys Gln Glu Pro Val Lys Pro Glu Glu Gly
    130                 135                 140

Arg Asp Met Ala Asn Arg Ile Gly Ala Phe Gly Tyr Met Glu Cys Ser
145                 150                 155                 160

Ala Lys Thr Lys Asp Gly Val Arg Glu Val Phe Glu Met Ala Thr Arg
                165                 170                 175

Ala Ala Leu Gln Ala Arg Arg Gly Lys Lys Ser Gly Cys Leu Val
            180                 185                 190

Leu
```

<210> SEQ ID NO 24
<211> LENGTH: 579
<212> TYPE: DNA
<213> ORGANISM: homo sapiens
<220> FEATURE:
<221> NAME/KEY: misc_feature
<223> OTHER INFORMATION: Rac1 gene

<400> SEQUENCE: 24

```
atgcaggcca tcaagtgtgt ggtggtggga gacggagctg taggtaaaac ttgcctactg    60
atcagttaca caaccaatgc atttcctgga gaatatatcc ctactgtctt tgacaattat   120
tctgccaatg ttatggtaga tggaaaaccg gtgaatctgg gcttatggga tacagctgga   180
caagaagatt atgacagatt acgcccccta tcctatccgc aaacagatgt gttcttaatt   240
tgcttttccc ttgtgagtcc tgcatcattt gaaaatgtcc gtgcaaagtg gtatcctgag   300
gtgcggcacc actgtcccaa cactcccatc atcctagtgg aactaaaact tgatcttagg   360
gatgataaag acacgatcga gaactgaag gagaagaagc tgactcccat cacctatccg   420
cagggtctag ccatggctaa ggagattggt gctgtaaaat acctggagtg ctcggcgctc   480
acacagcgag gcctcaagac agtgtttgac gaagcgatcc gagcagtcct ctgcccgcct   540
cccgtgaaga agaggaagag aaaatgcctg ctgttgtaa                          579
```

<210> SEQ ID NO 25
<211> LENGTH: 192
<212> TYPE: PRT
<213> ORGANISM: homo sapiens
<220> FEATURE:
<221> NAME/KEY: misc_feature
<223> OTHER INFORMATION: Rac1

<400> SEQUENCE: 25

Met Gln Ala Ile Lys Cys Val Val Val Gly Asp Gly Ala Val Gly Lys
1               5                   10                  15

Thr Cys Leu Leu Ile Ser Tyr Thr Thr Asn Ala Phe Pro Gly Glu Tyr
            20                  25                  30

Ile Pro Thr Val Phe Asp Asn Tyr Ser Ala Asn Val Met Val Asp Gly
        35                  40                  45

Lys Pro Val Asn Leu Gly Leu Trp Asp Thr Ala Gly Gln Glu Asp Tyr
    50                  55                  60

Asp Arg Leu Arg Pro Leu Ser Tyr Pro Gln Thr Asp Val Phe Leu Ile
65                  70                  75                  80

Cys Phe Ser Leu Val Ser Pro Ala Ser Phe Glu Asn Val Arg Ala Lys
                85                  90                  95

Trp Tyr Pro Glu Val Arg His His Cys Pro Asn Thr Pro Ile Ile Leu
            100                 105                 110

Val Gly Thr Lys Leu Asp Leu Arg Asp Asp Lys Asp Thr Ile Glu Lys
        115                 120                 125

Leu Lys Glu Lys Lys Leu Thr Pro Ile Thr Tyr Pro Gln Gly Leu Ala
    130                 135                 140

Met Ala Lys Glu Ile Gly Ala Val Lys Tyr Leu Glu Cys Ser Ala Leu
145                 150                 155                 160

Thr Gln Arg Gly Leu Lys Thr Val Phe Asp Glu Ala Ile Arg Ala Val
                165                 170                 175

Leu Cys Pro Pro Pro Val Lys Lys Arg Lys Arg Lys Cys Leu Leu Leu
            180                 185                 190

<210> SEQ ID NO 26
<211> LENGTH: 3652
<212> TYPE: DNA
<213> ORGANISM: Homo sapiens
<220> FEATURE:
<221> NAME/KEY: misc_feature
<223> OTHER INFORMATION: Gene encoding proto-Dbl (SEQ ID NO:27)
<220> FEATURE:
<221> NAME/KEY: CDS
<222> LOCATION: (175)..(2952)

<400> SEQUENCE: 26
tttttttttt ttcctcccaa cattgctgcc actgtgctaa tggaagcacc acggcagctt      60
tgtttgatag agattttttgg ctgccgtttt taaatactac ccaagaagca gctcgtattt    120
catcaatgtt gcgttgacaa ttggaaaaga aaagtgtaat tgcgtacagg cgaa atg      177
                                                              Met
                                                              1 gca gaa gca aat ccc cgg aga ggc aag atg agg ttc aga agg aat gcg      225
Ala Glu Ala Asn Pro Arg Arg Gly Lys Met Arg Phe Arg Arg Asn Ala
        5                   10                  15 gct tcc ttc cct ggg aac ttg cac ttg gtt ttg gtt tta cgt cct acc      273
Ala Ser Phe Pro Gly Asn Leu His Leu Val Leu Val Leu Arg Pro Thr
    20                  25                  30 agc ttt ctt caa cga acg ttc aca gac att gga ttt tgg ttt agt cag      321
Ser Phe Leu Gln Arg Thr Phe Thr Asp Ile Gly Phe Trp Phe Ser Gln
35                  40                  45 gag gat ttt atg cct aaa tta cca gtt gtt atg ctg agc tca gtt agt      369
Glu Asp Phe Met Pro Lys Leu Pro Val Val Met Leu Ser Ser Val Ser
50                  55                  60                  65 gat ttg ctg aca tac att gat gac aag caa tta acc cct gag tta ggc      417
Asp Leu Leu Thr Tyr Ile Asp Asp Lys Gln Leu Thr Pro Glu Leu Gly
            70                  75                  80

```
ggc acc ttg cag tac tgc cac agt gaa tgg atc atc ttc aga aat gct      465
Gly Thr Leu Gln Tyr Cys His Ser Glu Trp Ile Ile Phe Arg Asn Ala
            85                  90                  95 ata gaa aat ttt gcc ctc aca gtg aaa gaa atg gct cag atg tta cag      513
Ile Glu Asn Phe Ala Leu Thr Val Lys Glu Met Ala Gln Met Leu Gln
        100                 105                 110 tcc ttt gga act gaa ctg gct gag aca gaa cta cca gat gat att ccc      561
Ser Phe Gly Thr Glu Leu Ala Glu Thr Glu Leu Pro Asp Asp Ile Pro
    115                 120                 125 tca ata gaa gaa att ctg gca att cgt gct gaa agg tat cat ctg ttg      609
Ser Ile Glu Glu Ile Leu Ala Ile Arg Ala Glu Arg Tyr His Leu Leu
130                 135                 140                 145 aag aat gat att aca gct gta acc aaa gaa gga aaa att ctg cta aca      657
Lys Asn Asp Ile Thr Ala Val Thr Lys Glu Gly Lys Ile Leu Leu Thr
                150                 155                 160 aat ctg gaa gtg cct gac act gaa gga gct gtc agt tca aga cta gaa      705
Asn Leu Glu Val Pro Asp Thr Glu Gly Ala Val Ser Ser Arg Leu Glu
            165                 170                 175 tgt cat cgg caa ata agt ggt gac tgg caa act att aat aag ttg ctg      753
Cys His Arg Gln Ile Ser Gly Asp Trp Gln Thr Ile Asn Lys Leu Leu
        180                 185                 190 act caa gta cat gat atg gaa aca gct ttt gat gga ttt tgg gaa aaa      801
Thr Gln Val His Asp Met Glu Thr Ala Phe Asp Gly Phe Trp Glu Lys
    195                 200                 205 cat caa tta aaa atg gag cag tat ctg caa cta tgg aag ttt gag cag      849
His Gln Leu Lys Met Glu Gln Tyr Leu Gln Leu Trp Lys Phe Glu Gln
210                 215                 220                 225 gat ttt caa cag ctt gtg act gaa gtt gaa ttt cta tta aac caa caa      897
Asp Phe Gln Gln Leu Val Thr Glu Val Glu Phe Leu Leu Asn Gln Gln
                230                 235                 240 gca gaa ctg gct gat gta aca ggg act ata gct caa gta aaa caa aaa      945
Ala Glu Leu Ala Asp Val Thr Gly Thr Ile Ala Gln Val Lys Gln Lys
            245                 250                 255 ata aaa aaa ttg gaa aac tta gat gaa aat tct cag gag cta tta tca      993
Ile Lys Lys Leu Glu Asn Leu Asp Glu Asn Ser Gln Glu Leu Leu Ser
        260                 265                 270 aag gcc cag ttt gtg ata tta cat gga cac aag ctt gca gca aat cac     1041
Lys Ala Gln Phe Val Ile Leu His Gly His Lys Leu Ala Ala Asn His
    275                 280                 285 cat tat gca ctt gat tta atc tgc cag agg tgc aat gag cta cgt tac     1089
His Tyr Ala Leu Asp Leu Ile Cys Gln Arg Cys Asn Glu Leu Arg Tyr
290                 295                 300                 305 ctt tct gat att ttg gtt aat gag ata aaa gca aaa cgg ata caa ctc     1137
Leu Ser Asp Ile Leu Val Asn Glu Ile Lys Ala Lys Arg Ile Gln Leu
                310                 315                 320 agc agg acc ttc aaa atg cat aaa ctc cta cag cag gct cgt caa tgc     1185
Ser Arg Thr Phe Lys Met His Lys Leu Leu Gln Gln Ala Arg Gln Cys
            325                 330                 335 tgt gat gaa ggg gaa tgt ctt cta gct aat cag gaa ata gat aag ttt     1233
Cys Asp Glu Gly Glu Cys Leu Leu Ala Asn Gln Glu Ile Asp Lys Phe
        340                 345                 350 cag tct aaa gaa gat gct cag aaa gct ctc caa gac att gaa aat ttt     1281
Gln Ser Lys Glu Asp Ala Gln Lys Ala Leu Gln Asp Ile Glu Asn Phe
    355                 360                 365 ctt gaa atg gct cta ccc ttt ata aat tat gaa cct gaa aca ctg cag     1329
Leu Glu Met Ala Leu Pro Phe Ile Asn Tyr Glu Pro Glu Thr Leu Gln
370                 375                 380                 385 tat gaa ttt gat gta ata tta tct cct gag ctt aag gtt caa atg aag     1377
Tyr Glu Phe Asp Val Ile Leu Ser Pro Glu Leu Lys Val Gln Met Lys
                390                 395                 400
```

```
act ata caa ctc aag ctt gaa aac att cga agt ata ttt gag aac cag     1425
Thr Ile Gln Leu Lys Leu Glu Asn Ile Arg Ser Ile Phe Glu Asn Gln
            405                 410                 415 cag gct ggt ttc agg aac ctg gca gat aag cat gtg agg cca atc caa     1473
Gln Ala Gly Phe Arg Asn Leu Ala Asp Lys His Val Arg Pro Ile Gln
        420                 425                 430 ttt gtg gta ccc aca cct gaa aat ttg gtc aca tct ggg aca cca ttt     1521
Phe Val Val Pro Thr Pro Glu Asn Leu Val Thr Ser Gly Thr Pro Phe
    435                 440                 445 ttt tca tct aaa caa ggg aag aag act tgg aga caa aat cag agc aac     1569
Phe Ser Ser Lys Gln Gly Lys Lys Thr Trp Arg Gln Asn Gln Ser Asn
450                 455                 460                 465 tta aaa att gaa gtg gtg cct gat tgt cag gag aag aga agt tct ggt     1617
Leu Lys Ile Glu Val Val Pro Asp Cys Gln Glu Lys Arg Ser Ser Gly
                470                 475                 480 cca tcc tcc agt ttg gac aat ggc aat agc ttg gat gtt tta aag aac     1665
Pro Ser Ser Ser Leu Asp Asn Gly Asn Ser Leu Asp Val Leu Lys Asn
            485                 490                 495 cac gta cta aat gaa ctg ata cag act gag aga gtt tat gtt cga gaa     1713
His Val Leu Asn Glu Leu Ile Gln Thr Glu Arg Val Tyr Val Arg Glu
        500                 505                 510 ctg tat act gtt ttg ttg ggt tat aga gcg gag atg gat aat cca gag     1761
Leu Tyr Thr Val Leu Leu Gly Tyr Arg Ala Glu Met Asp Asn Pro Glu
    515                 520                 525 atg ttt gat ctt atg cca cct ctc ctg aga aat aaa aag gac att ctc     1809
Met Phe Asp Leu Met Pro Pro Leu Leu Arg Asn Lys Lys Asp Ile Leu
530                 535                 540                 545 ttt gga aac atg gca gaa ata tat gaa ttc cat aac gac att ttc ttg     1857
Phe Gly Asn Met Ala Glu Ile Tyr Glu Phe His Asn Asp Ile Phe Leu
                550                 555                 560 agc agc ctg gaa aat tgt gct cat gct cca gaa aga gtg gga cct tgt     1905
Ser Ser Leu Glu Asn Cys Ala His Ala Pro Glu Arg Val Gly Pro Cys
            565                 570                 575 ttc ctg gaa agg aag gat gat ttt cag atg tat gca aaa tat tgt cag     1953
Phe Leu Glu Arg Lys Asp Asp Phe Gln Met Tyr Ala Lys Tyr Cys Gln
        580                 585                 590 aat aag ccc aga tca gaa aca att tgg agg aag tat tca gaa tgc gca     2001
Asn Lys Pro Arg Ser Glu Thr Ile Trp Arg Lys Tyr Ser Glu Cys Ala
    595                 600                 605 ttt ttc cag gaa tgt caa aga aag tta aaa cac aga ctt aga ctg gat     2049
Phe Phe Gln Glu Cys Gln Arg Lys Leu Lys His Arg Leu Arg Leu Asp
610                 615                 620                 625 tcc tat tta ctc aaa cca gtg caa cga atc act aaa tat cag tta ttg     2097
Ser Tyr Leu Leu Lys Pro Val Gln Arg Ile Thr Lys Tyr Gln Leu Leu
                630                 635                 640 ttg aag gag cta tta aaa tat agc aaa gac tgt gaa ggt tct gct ctg     2145
Leu Lys Glu Leu Leu Lys Tyr Ser Lys Asp Cys Glu Gly Ser Ala Leu
            645                 650                 655 ttg aag aag gca ctc gat gca atg ctg gat tta ctg aag tca gtt aat     2193
Leu Lys Lys Ala Leu Asp Ala Met Leu Asp Leu Leu Lys Ser Val Asn
        660                 665                 670 gat tct atg cat cag att gca ata aat ggc tat att gga aac tta aat     2241
Asp Ser Met His Gln Ile Ala Ile Asn Gly Tyr Ile Gly Asn Leu Asn
    675                 680                 685 gaa ctg ggc aag atg ata atg caa ggt gga ttc agc gtt tgg ata ggg     2289
Glu Leu Gly Lys Met Ile Met Gln Gly Gly Phe Ser Val Trp Ile Gly
690                 695                 700                 705 cac aag aaa ggt gct aca aaa atg aag gat ttg gct aga ttc aaa cca     2337
His Lys Lys Gly Ala Thr Lys Met Lys Asp Leu Ala Arg Phe Lys Pro
                710                 715                 720
```

| | | |
|---|---|---|
| atg cag cga cac ctt ttc ttg tat gaa aaa gcc att gtt ttt tgc aaa<br>Met Gln Arg His Leu Phe Leu Tyr Glu Lys Ala Ile Val Phe Cys Lys<br>725                           730                       735 | | 2385 |
| agg cgt gtt gaa agt gga gaa ggc tct gac aga tac ccg tca tac agt<br>Arg Arg Val Glu Ser Gly Glu Gly Ser Asp Arg Tyr Pro Ser Tyr Ser<br>        740                       745                       750 | | 2433 |
| ttt aaa cac tgt tgg aaa atg gat gaa gtt gga atc act gaa tat gta<br>Phe Lys His Cys Trp Lys Met Asp Glu Val Gly Ile Thr Glu Tyr Val<br>        755                       760                    765 | | 2481 |
| aaa ggt gat aac cgc aag ttt gaa atc tgg tat ggt gaa aag gaa gaa<br>Lys Gly Asp Asn Arg Lys Phe Glu Ile Trp Tyr Gly Glu Lys Glu Glu<br>770                       775                     780                    785 | | 2529 |
| gtt tat att gtc cag gct tct aat gta gat gtg aag atg acg tgg cta<br>Val Tyr Ile Val Gln Ala Ser Asn Val Asp Val Lys Met Thr Trp Leu<br>                    790                     795                    800 | | 2577 |
| aaa gaa ata aga aat att ttg ttg aag cag cag gaa ctt ttg aca gtt<br>Lys Glu Ile Arg Asn Ile Leu Leu Lys Gln Gln Glu Leu Leu Thr Val<br>805                       810                       815 | | 2625 |
| aaa aaa aga aag caa cag gat caa tta aca gaa cgg gat aag ttt cag<br>Lys Lys Arg Lys Gln Gln Asp Gln Leu Thr Glu Arg Asp Lys Phe Gln<br>820                       825                     830 | | 2673 |
| att tct ctt cag cag aat gat gaa aag caa cag gga gct ttt ata agt<br>Ile Ser Leu Gln Gln Asn Asp Glu Lys Gln Gln Gly Ala Phe Ile Ser<br>835                       840                     845 | | 2721 |
| act gag gaa act gaa ttg gaa cac acc agc act gtg gtg gag gtc tgt<br>Thr Glu Glu Thr Glu Leu Glu His Thr Ser Thr Val Val Glu Val Cys<br>850                       855                     860                    865 | | 2769 |
| gag gca att gcg tca gtt cag gca gaa gca aat aca gtt tgg act gag<br>Glu Ala Ile Ala Ser Val Gln Ala Glu Ala Asn Thr Val Trp Thr Glu<br>                    870                     875                    880 | | 2817 |
| gca tca caa tct gca gaa atc tct gaa gaa cct gcg gaa tgg tca agc<br>Ala Ser Gln Ser Ala Glu Ile Ser Glu Glu Pro Ala Glu Trp Ser Ser<br>885                       890                     895 | | 2865 |
| aac tat ttc tac cct act tat gat gaa aat gaa gaa gaa aat agg ccc<br>Asn Tyr Phe Tyr Pro Thr Tyr Asp Glu Asn Glu Glu Glu Asn Arg Pro<br>        900                       905                       910 | | 2913 |
| ctc atg aga cct gtg tcg gag atg gct ctc cta tat tga tgaagctact<br>Leu Met Arg Pro Val Ser Glu Met Ala Leu Leu Tyr<br>915                     920                     925 | | 2962 |
| atgtcaaatg gcaagtagct cttccctgcc tgcttctcag ctcatttgga aaaatactgc | | 3022 |
| gcaaaagaca ttgagctcaa atgatgcaga tgttgtttc aggttaatgg acacgcaaag | | 3082 |
| aaaccacagc acatacttct tttctttcat ttaataaagc ttttaattat ggtacgctgt | | 3142 |
| cttttttaaaa tcatgtattt aatgtgtcag atattgtgct tgaaagattc tcatctcaga | | 3202 |
| atactttttgg acttgaaaat tatttcttct ctactttgta accaaatgca atcggtgtgc | | 3262 |
| cttggattat ttagtttatt aatgaattaa gtcaaaatta cggctgcaaa atggctaagg | | 3322 |
| tcaagtaaag cacaacatta tgatttaata tgcttttgtt gaaaccacag cttttgtgcc | | 3382 |
| cattgtttta acttgtgtga acaatacaa agcccagaaa ttcttttcgg ggcatgagta | | 3442 |
| aattttgttc agggctactg tctgtatgtg cccagataaa attttcatga gagtagttta | | 3502 |
| caaaagccgt atttaaaagt taatattttc acacttttttt tctggatttc tgcttataat | | 3562 |
| taatgtaact taaattagtt gtgctctgct attttctgta tatttcatgt tgtaattctt | | 3622 |
| tttttcaaat aaaaattaat tcttcaggtt | | 3652 |

<210> SEQ ID NO 27
<211> LENGTH: 925

<212> TYPE: PRT
<213> ORGANISM: Homo sapiens

<400> SEQUENCE: 27

```
Met Ala Glu Ala Asn Pro Arg Arg Gly Lys Met Arg Phe Arg Arg Asn
1               5                   10                  15

Ala Ala Ser Phe Pro Gly Asn Leu His Leu Val Leu Val Leu Arg Pro
            20                  25                  30

Thr Ser Phe Leu Gln Arg Thr Phe Thr Asp Ile Gly Phe Trp Phe Ser
        35                  40                  45

Gln Glu Asp Phe Met Pro Lys Leu Pro Val Val Met Leu Ser Ser Val
50                  55                  60

Ser Asp Leu Leu Thr Tyr Ile Asp Asp Lys Gln Leu Thr Pro Glu Leu
65                  70                  75                  80

Gly Gly Thr Leu Gln Tyr Cys His Ser Glu Trp Ile Ile Phe Arg Asn
                85                  90                  95

Ala Ile Glu Asn Phe Ala Leu Thr Val Lys Glu Met Ala Gln Met Leu
            100                 105                 110

Gln Ser Phe Gly Thr Glu Leu Ala Glu Thr Glu Leu Pro Asp Asp Ile
        115                 120                 125

Pro Ser Ile Glu Glu Ile Leu Ala Ile Arg Ala Glu Arg Tyr His Leu
130                 135                 140

Leu Lys Asn Asp Ile Thr Ala Val Thr Lys Glu Gly Lys Ile Leu Leu
145                 150                 155                 160

Thr Asn Leu Glu Val Pro Asp Thr Glu Gly Ala Val Ser Ser Arg Leu
                165                 170                 175

Glu Cys His Arg Gln Ile Ser Gly Asp Trp Gln Thr Ile Asn Lys Leu
            180                 185                 190

Leu Thr Gln Val His Asp Met Glu Thr Ala Phe Asp Gly Phe Trp Glu
        195                 200                 205

Lys His Gln Leu Lys Met Glu Gly Tyr Leu Gln Leu Trp Lys Phe Glu
210                 215                 220

Gln Asp Phe Gln Gln Leu Val Thr Glu Val Glu Phe Leu Leu Asn Gln
225                 230                 235                 240

Gln Ala Glu Leu Ala Asp Val Thr Gly Thr Ile Ala Gln Val Lys Gln
                245                 250                 255

Lys Ile Lys Lys Leu Glu Asn Leu Asp Glu Asn Ser Gln Glu Leu Leu
            260                 265                 270

Ser Lys Ala Gln Phe Val Ile Leu His Gly His Lys Leu Ala Ala Asn
        275                 280                 285

His His Tyr Ala Leu Asp Leu Ile Cys Gln Arg Cys Asn Glu Leu Arg
290                 295                 300

Tyr Leu Ser Asp Ile Leu Val Asn Glu Ile Lys Ala Lys Arg Ile Gln
305                 310                 315                 320

Leu Ser Arg Thr Phe Lys Met His Lys Leu Gln Gln Ala Arg Gln
                325                 330                 335

Cys Cys Asp Glu Gly Glu Cys Leu Leu Ala Asn Gln Glu Ile Asp Lys
            340                 345                 350

Phe Gln Ser Lys Glu Asp Ala Gln Lys Ala Leu Gln Asp Ile Glu Asn
        355                 360                 365

Phe Leu Glu Met Ala Leu Pro Phe Ile Asn Tyr Glu Pro Glu Thr Leu
370                 375                 380

Gln Tyr Glu Phe Asp Val Ile Leu Ser Pro Glu Leu Lys Val Gln Met
385                 390                 395                 400
```

```
Lys Thr Ile Gln Leu Lys Leu Glu Asn Ile Arg Ser Ile Phe Glu Asn
                405                 410                 415

Gln Gln Ala Gly Phe Arg Asn Leu Ala Asp Lys His Val Arg Pro Ile
            420                 425                 430

Gln Phe Val Val Pro Thr Pro Glu Asn Leu Val Thr Ser Gly Thr Pro
        435                 440                 445

Phe Phe Ser Ser Lys Gln Gly Lys Lys Thr Trp Arg Gln Asn Gln Ser
    450                 455                 460

Asn Leu Lys Ile Glu Val Val Pro Asp Cys Gln Glu Lys Arg Ser Ser
465                 470                 475                 480

Gly Pro Ser Ser Ser Leu Asp Asn Gly Asn Ser Leu Asp Val Leu Lys
                485                 490                 495

Asn His Val Leu Asn Glu Leu Ile Gln Thr Glu Arg Val Tyr Val Arg
            500                 505                 510

Glu Leu Tyr Thr Val Leu Leu Gly Tyr Arg Ala Glu Met Asp Asn Pro
        515                 520                 525

Glu Met Phe Asp Leu Met Pro Pro Leu Leu Arg Asn Lys Lys Asp Ile
    530                 535                 540

Leu Phe Gly Asn Met Ala Glu Ile Tyr Glu Phe His Asn Asp Ile Phe
545                 550                 555                 560

Leu Ser Ser Leu Glu Asn Cys Ala His Ala Pro Glu Arg Val Gly Pro
                565                 570                 575

Cys Phe Leu Glu Arg Lys Asp Asp Phe Gln Met Tyr Ala Lys Tyr Cys
            580                 585                 590

Gln Asn Lys Pro Arg Ser Glu Thr Ile Trp Arg Lys Tyr Ser Glu Cys
        595                 600                 605

Ala Phe Phe Gln Glu Cys Gln Arg Lys Leu Lys His Arg Leu Arg Leu
    610                 615                 620

Asp Ser Tyr Leu Leu Lys Pro Val Gln Arg Ile Thr Lys Tyr Gln Leu
625                 630                 635                 640

Leu Leu Lys Glu Leu Leu Lys Tyr Ser Lys Asp Cys Glu Gly Ser Ala
                645                 650                 655

Leu Leu Lys Lys Ala Leu Asp Ala Met Leu Asp Leu Leu Lys Ser Val
            660                 665                 670

Asn Asp Ser Met His Gln Ile Ala Ile Asn Gly Tyr Ile Gly Asn Leu
        675                 680                 685

Asn Glu Leu Gly Lys Met Ile Met Gln Gly Gly Phe Ser Val Trp Ile
    690                 695                 700

Gly His Lys Lys Gly Ala Thr Lys Met Lys Asp Leu Ala Arg Phe Lys
705                 710                 715                 720

Pro Met Gln Arg His Leu Phe Leu Tyr Glu Lys Ala Ile Val Phe Cys
                725                 730                 735

Lys Arg Arg Val Glu Ser Gly Glu Gly Ser Asp Arg Tyr Pro Ser Tyr
            740                 745                 750

Ser Phe Lys His Cys Trp Lys Met Asp Glu Val Gly Ile Thr Glu Tyr
        755                 760                 765

Val Lys Gly Asp Asn Arg Lys Phe Glu Ile Trp Tyr Gly Glu Lys Glu
    770                 775                 780

Glu Val Tyr Ile Val Gln Ala Ser Asn Val Asp Val Lys Met Thr Trp
785                 790                 795                 800

Leu Lys Glu Ile Arg Asn Ile Leu Leu Lys Gln Gln Glu Leu Leu Thr
                805                 810                 815

Val Lys Lys Arg Lys Gln Gln Asp Gln Leu Thr Glu Arg Asp Lys Phe
            820                 825                 830
```

```
Gln Ile Ser Leu Gln Gln Asn Asp Glu Lys Gln Gln Gly Ala Phe Ile
        835                 840                 845

Ser Thr Glu Thr Glu Leu Glu His Thr Ser Thr Val Val Glu Val
850                 855                 860

Cys Glu Ala Ile Ala Ser Val Gln Ala Glu Ala Asn Thr Val Trp Thr
865                 870                 875                 880

Glu Ala Ser Gln Ser Ala Glu Ile Ser Glu Glu Pro Ala Glu Trp Ser
                885                 890                 895

Ser Asn Tyr Phe Tyr Pro Thr Tyr Asp Glu Asn Glu Glu Glu Asn Arg
                900                 905                 910

Pro Leu Met Arg Pro Val Ser Glu Met Ala Leu Leu Tyr
                915                 920                 925
```

ANTIBODY TO A GUANINE NUCLEOTIDE EXCHANGE FACTOR

This application is a divisional of U.S. patent application Ser. No. 10/594,707, filed Jan. 19, 2007 (now U.S. Pat. No. 7,667,013), which, in turn, is a National Stage Application of PCT/JP2005/005918, filed Mar. 29, 2005.

TECHNICAL FIELD

The present invention relates to proteins acting as guanine nucleotide exchange factors on Rho family proteins that are one group of a small GTP-binding protein, and to a polynucleotide encoding the protein. Specifically, the present invention relates to a protein that binds to the Rho family small GTP-binding protein Cdc42, a polynucleotide encoding the protein, a recombinant vector containing the polynucleotide, and a transformant transfected with the recombinant vector. Further, the present invention relates to a method of producing the protein, and an antibody specific to the protein. Furthermore, the present invention relates to a method of identifying a compound that inhibits the function of the protein and/or the expression of the polynucleotide. Further, the present invention relates to a method of diagnosing a stomach tumor, comprising measuring the amount of expression of the polynucleotide. Furthermore, the present invention relates to an agent for preventing and/or treating a stomach tumor, containing an inhibitor for the function of the protein and/or an inhibitor for the expression of the polynucleotide, and a method of preventing and/or treating a stomach tumor, comprising using an inhibitor for the function of the protein and/or an inhibitor for the expression of the polynucleotide. Further, the present invention relates to a reagent kit containing at least one of the following components: the protein; the polynucleotide; the recombinant vector; the transformant; and the antibody.

BACKGROUND OF INVENTION

A Rho family small GTP-binding protein (hereinafter, may be simply referred to as a Rho family protein) belongs to one group of small GTP-binding proteins (hereinafter, may be simply referred to as a small G protein). A small G protein works as a signal amplifier between a cell membrane receptor, and an effector participating in an intracellular signal transduction pathway. Further, the small G protein specifically binds to guanosine 5'-triphosphate (GTP) or guanosine 5'-diphosphate (GDP), and shows an enzyme activity of hydrolyzing the bound GTP to GDP. When an extracellular signaling substance binds to a cell membrane receptor, its signal is transduced to a small G protein, which subsequently leads to a reaction exchanging a GDP bound to the small G protein for an intracellular GTP (hereinafter, the reaction may be abbreviated to GDP/GTP exchange reaction). Consequently, an active (GTP binding form) small G protein is generated. The active small G protein acts on the effector to amplify the signal. Then, the active small G protein hydrolyzes the bound GTP to GDP by its enzyme activity, and thereby becomes inactivated. Thus, the active small G protein works as a molecular switch in an intracellular signal transduction pathway by exchanging the guanine nucleotides.

Cdc42, Rac1, RhoA and the like are known as Rho family proteins. Cdc42 regulates filopodia formation in a fibroblast. Rac 1 regulates superoxide production in leukocytes and macrophages, while it regulates cell membrane ruffling and lamellipodia formation in fibroblasts. Further, Cdc42 and Rac1 are capable of activating the c-Jun N-terminal kinase signal transduction pathway. Thus, Rho family proteins are involved in various kinds of cell function by regulating the intracellular signal transduction. For example, cytoskeleton restructuring, cell adhesion, gene expression, and the like are known as a Rho family protein-mediated cell functions. Such functions mediated by Rho family proteins are considered to regulate morphogenesis during ontogeny, migration of leukocytes and the like, axon degeneration, tumor metastasis, and tumor invasion.

Rho guanine nucleotide exchange factor (hereinafter, may be abbreviated as Rho-GEF) is a member of a family of proteins involved in the molecular switching of a Rho family protein. Rho-GEF can function to accelerate the GDP/GTP exchange reaction of a Rho family protein, and can thereby accelerate the activation of the Rho family protein. Rho-GEF plays an important role through this function, in regulating Rho family protein-mediated intracellular signal transduction. Hereinafter, the function of accelerating the GDP/GTP exchange reaction may be referred to as GEF activity.

Rho-GEF has a characteristic domain structure, such as a Dbl homology domain (hereinafter, may be abbreviated as DH domain) and a pleckstrin homology domain (hereinafter, may be abbreviated as PH domain). The DH/PH tandem structure is a typical domain structure for Rho-GEF. Hereinafter, the tandem structure of DH domain and PH domain may be referred to as DH/PH domain.

The DH/PH domain is an important domain participating in the Rho-GEF-mediated activation of a Rho family protein, and is considered to be an active domain of Rho-GEF. For example, it has been reported that a protein, which comprises a C-terminal region of the amino acid sequence of proto-Dbl, and contains a DH/PH domain, activated a Rho family protein (Non-Patent Reference 1). proto-Dbl is a prototype of Rho-GEF. Specifically, this report showed that a protein consisting of a C-terminal region within the entire amino acid sequence of Proto-Dbl with 925 amino acids, which was generated by deletion of the N-terminal amino acid residues from the 1$^{st}$ to the 497$^{th}$, activated a Rho family protein, and consequently participated in cellular morphological change. From these facts, the activation of proto-Dbl is considered to be an oncogenic activation. Hereinafter, a protein that consists of the C-terminal region of proto-Dbl is referred to as an oncogenic-Dbl. It has been reported that oncogenic-Dbl bind to RhoA, Cdc42 and Rac1, and that they have a GEF activity for Cdc42 and RhoA while they do not exert a GEF activity to Rac1 (Non-Patent Reference 2).

Vav (Non-Patent Reference 3 and 4), ost (Non-Patent Reference 5), lbc (Non-Patent Reference 6), and the like, are known to be genes that encode proto-Dbl family proteins. These genes are known to be involved in cancer. Further, trio (Non-Patent Reference 7), kalirin (Non-Patent Reference 8), and the like, are reported to be genes that encode proteins working as Rho-GEF. A trio knocked-out mouse shows an abnormal skeletal muscle structure and an abnormal brain structure in embryogenesis. Kalirin is involved in axon formation in neurons. Thus, each protein working as a Rho-GEF is involved in a cellular function particular to each kind of protein, and activates a different Rho family protein.

Literatures referred in the present description are listed hereunder.

Non-patent Reference 1: Bi, F. et al., Molecular and Cellular Biology, 2001, Vol. 21, p. 1463-1474

Non-patent Reference 2: Hart, M. J. et al., Journal of Biological Chemistry, 1994, Vol. 269, p. 62-65

Non-patent Reference 3: Katzav, S. et al., EMBO Journal, 1989, Vol. 8, p. 2283-2290

Non-patent Reference 4: Costello, P. S. et al., Proceedings of The National Academy of Sciences of The United States of America, 1999, Vol. 96, p. 3035-3040

Non-patent Reference 5: Horii, Y. et al., EMBO Journal, 1994, Vol. 13, p. 4776-4786

Non-patent Reference 6: Toksoz, D. et al., Oncogene, 1994, Vol. 9, p. 621-628

Non-patent Reference 7: O'Brien, S. P. et al., Proceedings of The National Academy of Sciences of The United States of America, 2000, Vol. 97, p. 12074-12078

Non-patent Reference 8: Penzes, P. et al., Journal of Neuroscience, 2001, Vol. 21, p. 8426-8434

Non-patent Reference 9: Sambrook et al., Eds., "Molecular Cloning, A Laboratory Manual, $2^{nd}$ Edition", 1989, Cold Spring Harbor Laboratory Non-patent Reference 10: Muramatsu Masami., Ed., "Labomanual Genetic Engineering", 1988, Maruzen Co., Ltd.

Non-patent Reference 11: Madin, K. et al., Proceedings of The National Academy of Sciences of The United States of America, 2000, Vol. 97, p. 559-564

Non-patent Reference 12: Ulmer, K. M. Science, 1983, Vol. 219, p. 666-671

Non-patent Reference 13: Ehrlich, H. A., Ed., PCR Technology. Principles and Applications for DNA Amplification, 1989, Stockton Press Non-patent Reference 14: Saiki, R. K. et al., Science, 1985, Vol. 230, p. 1350-1354

Non-patent Reference 15: Jikken Igaku (Experimental Medicine), 1994, Vol. 12, No. 6, p. 35

Non-patent Reference 16: Frohman, M. A. et al., Proceedings of The National Academy of Sciences of The United States of America, 1988, Vol. 85, No. 23, p. 8998-9002

Non-patent Reference 17: Sanger, F. et al., Proceedings of The National Academy of Sciences of The United States of America, 1977, Vol. 74, p. 5463-5467

Non-patent Reference 18: Maxam, A. M. et al., Methods in Enzymology, 1980, Vol. 65, p. 499-560

Non-patent Reference 19: Ohara, O. et al., DNA Research, 1997, Vol. 4, p. 53-59

DISCLOSURE OF THE INVENTION

An object of the present invention is to provide a novel Rho-GEF, and a gene encoding the Rho-GEF. Further, the object of the present invention includes providing a recombinant vector that contains the gene, and a transformant transfected with the recombinant vector. Furthermore, an object of the present invention includes providing a method of producing the Rho-GEF, and an antibody recognizing the Rho-GEF. Further, an object of the present invention includes providing a method of identifying a compound that inhibits the function of the Rho-GEF and/or the expression of the gene. Furthermore, an object of the present invention includes providing a method of preventing and/or treating a disease due to the abnormal function of the Rho-GEF and/or the abnormal expression of the gene, a method of diagnosing the disease, and a reagent kit.

The present inventors have concentrated their efforts to meet the aforementioned objects and have discovered a gene encoding a novel Rho-GEF, and have successfully obtained a novel Rho-GEF by using the gene. Further, the present inventors revealed experimentally that a partial protein of the Rho-GEF containing the DH/PH domain, bound to Rho family proteins such as RhoA, Cdc42 and Rac1, respectively. Furthermore, the present inventors proved that the protein accelerated the activation of Cdc42. Moreover, the present inventors found that the tissue expression of the Rho-GEF gene is approximately 5 times or more higher, specifically 4.5 times or more higher, in a case with adenocarcinoid tumor of the stomach, compared to that in a normal stomach tissue. The present invention has been thus achieved.

In various embodiments, the present invention relates to a polynucleotide shown by the nucleotide sequence set forth in SEQ ID NO: 1, in the sequence listing or by the complementary nucleotide sequence, or a polynucleotide encoding a protein shown by the amino acid sequence set forth in SEQ ID NO: 2 in the sequence listing, or a polynucleotide shown by the complementary nucleotide sequence of the polynucleotide.

The present invention also relates to a polynucleotide shown by the nucleotide sequence set forth in SEQ ID NO: 3, or SEQ ID NO: 5 in the sequence listing, or by the complementary nucleotide sequence, or a polynucleotide encoding a protein shown by the amino acid sequence set forth in SEQ ID NO: 4 or SEQ ID NO: 6 in the sequence listing, or a polynucleotide shown by the complementary nucleotide sequence of the polynucleotide.

The present invention further relates to a polynucleotide that contains a polynucleotide shown by the nucleotide sequence set forth in SEQ ID NO: 3 in the sequence listing, or by the complementary nucleotide sequence or, a polynucleotide that contains a polynucleotide encoding a protein shown by the amino acid sequence set forth in SEQ ID NO: 4 in the sequence listing, or a polynucleotide shown by the complementary nucleotide sequence of the polynucleotide, wherein the polynucleotide encodes a protein that accelerates the activation of Cdc42.

The present invention still further relates to a polynucleotide shown by a nucleotide sequence having a homology of at least approximately 70% with the nucleotide sequence of the aforementioned polynucleotide, wherein the polynucleotide encodes a protein that accelerates the activation of Cdc42.

The present invention also relates to a polynucleotide with a mutation, or an induced mutation, such as deletion, substitution, or addition of one or more nucleotides in the nucleotide sequence of the aforementioned polynucleotide, wherein the polynucleotide encodes a protein that accelerates the activation of Cdc42.

The present invention further relates to polynucleotides that hybridize to the aforementioned polynucleotide under stringent conditions, wherein the polynucleotides encode proteins that accelerate the activation of Cdc42.

The present invention still further relates to recombinant vectors containing any one of the aforementioned polynucleotides.

The present invention also relates to transformants that have been transfected with any of the aforementioned recombinant vectors.

The present invention further relates to transformants that have been transfected with any of the aforementioned recombinant vectors and recombinant vectors containing a polynucleotide encoding Cdc42.

The present invention still further relates to a protein shown by the amino acid sequence set forth in SEQ ID NO: 2 in the sequence listing.

The present invention also relates to proteins shown by the amino acid sequence set forth in SEQ ID NO: 4 or SEQ ID NO: 6 in the sequence listing.

The present invention further relates to proteins encoded by any one of the aforementioned polynucleotides.

The present invention still further relates to methods of producing any one of the aforementioned proteins, comprising a step of culturing the aforementioned transformants.

The present invention also relates to antibodies that recognize any one of the aforementioned proteins.

The present invention further relates to a method of identifying a compound that inhibits the function of any one of the aforementioned proteins, and/or the expression of any one of the aforementioned polynucleotides. The method can comprise detecting the presence, absence or change in the function and/or the expression of any of the aforementioned proteins or polynucleotides, under conditions where the interaction of a compound with the protein and/or the polynucleotide are allowed, and determining whether the compound inhibits the function of the protein and/or the expression of the polynucleotide.

The present invention still further relates to the aforementioned identification method, wherein the function of the protein is a function of binding to Cdc42, and/or a function of accelerating the activation of Cdc42.

The present invention also relates to a method of identifying a compound that inhibits the function of any one of the aforementioned proteins, and/or the expression of any one of the aforementioned polynucleotides, comprising using at least one of the aforementioned proteins, the aforementioned polynucleotides, the aforementioned recombinant vectors, the aforementioned transformants, and the aforementioned antibodies.

The present invention further relates to the aforementioned identification method, wherein the function of the protein is a function of binding to Cdc42, and/or a function of accelerating the activation of Cdc42.

The present invention still further relates to a method of determining whether a tissue specimen derived from human stomach tissue is a tissue derived from a human stomach tumor or not, comprising measuring the amount of expression of any one of the aforementioned polynucleotides in the tissue specimen.

The present invention also relates to the aforementioned determination method, wherein the method determines that the tissue specimen is a tissue derived from a human stomach tumor in the case where the amount of expression of any one of the aforementioned polynucleotides in the tissue specimen is 4.5 times or more higher than that in a control tissue derived from a normal human stomach.

The present invention further relates to agents for preventing and/or treating stomach tumors, comprising a compound with an active ingredient that inhibits the function of any one of the aforementioned proteins, and/or a compound that inhibits the expression of any one of the aforementioned polynucleotides.

The present invention still further relates to methods of preventing and/or treating stomach tumors, comprising administering a compound that inhibits the function of any one of the aforementioned proteins, and/or a compound that inhibits the expression of any one of the aforementioned polynucleotides.

The present invention also relates to a reagent kit containing at least one of the aforementioned proteins, the aforementioned polynucleotides, the aforementioned recombinant vectors, the aforementioned transformants, and the aforementioned antibodies.

ADVANTAGE OF THE INVENTION

The present invention can provide novel proteins that can bind to a Rho family protein, and are capable of accelerating a GDP/GTP exchange reaction to activate the Rho family protein, and polynucleotides encoding the protein. The present proteins can bind respectively to RhoA, Cdc42, and Rac1, that are Rho family proteins. Further, the present protein accelerates the activation of Cdc42. The present proteins and polynucleotides can be used for elucidating and regulating the signal transduction pathway and cellular function which are mediated by Rho family proteins. Further, the present proteins and polynucleotides can be used for carrying out diagnosis, prevention and/or treatment of a disease due to an abnormal function of the present proteins and/or an abnormal expression of the present polynucleotides, for example, a stomach tumor.

BRIEF DESCRIPTION OF THE DRAWINGS

FIG. 3-B shows that active Cdc42 which binds to PAK-1 was increased in a cell in which hj03796DH/PH was co-expressed with Cdc42 (lane 4), compared to that in a cell in which only Cdc42 was expressed. In the figure, GEF means hj03796DH/PH, and Rho means a Rho family protein. The white arrow head indicates a Rho family protein. (Example 4)

DETAILED DESCRIPTION OF THE INVENTION

Figure 1:
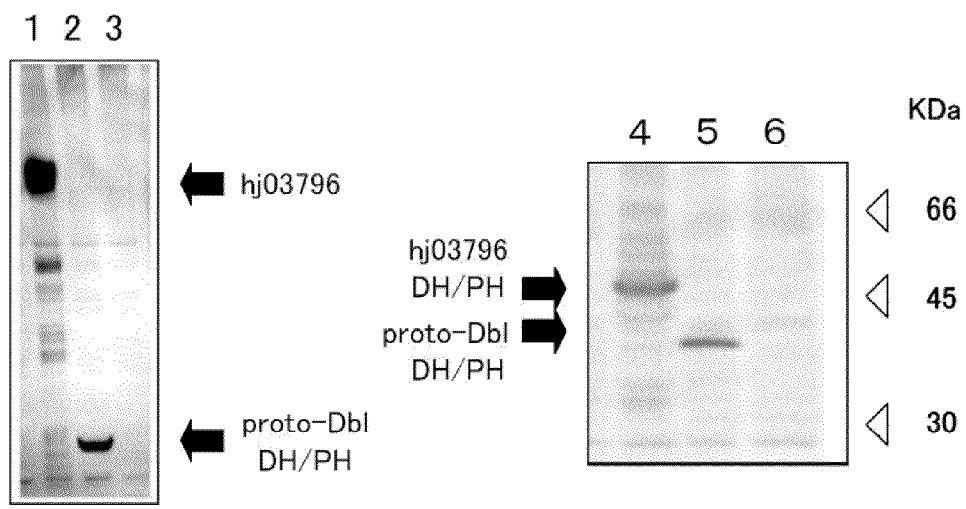
FIG. 1 shows a band corresponding to a protein encoded by hj03796, or a protein fragment (hj03796 DH/PH) containing the DH/PH domain of the protein, that was detected (lanes 1 and 4, respectively) by Western blotting of a cell lysate prepared from a cell that was transfected with a vector constructed by using cDNA clone hj03796, or by using DNA consisting of a partial sequence of the cDNA, containing a DH/PH domain coding region. Proto-Dbl DH/PH was used as a positive control (lanes 2 and 5). Such a band was not detected in a protein solution prepared in the same manner from a control cell that had not been transfected with the vector (lanes 3 and 6). (Example 2)

Embodiments of the present invention are explained in further detail below. In the present specification, the term "polynucleotide" may be used as a generic term which includes the following: an isolated full-length DNA and/or RNA; a synthetic full-length DNA and/or RNA; an isolated DNA oligonucleotide and/or RNA oligonucleotide; or a synthetic DNA oligonucleotide and/or RNA oligonucleotide. Such DNA and/or RNA used herein comprise two or more nucleotides.

In the present specification, the term "protein" may be used as a generic term which includes the following: an isolated or a synthetic full-length protein; an isolated or a synthetic full-length polypeptide; and an isolated or a synthetic full-length oligopeptide. A protein, a polypeptide or an oligopeptide used herein comprises two or more amino acids. Hereinafter, an amino acid may be represented by a single letter or by three letters.

An aspect of the present invention relates to a novel polynucleotide. The present polynucleotide was identified from a long-chain cDNA library derived from human brain tissue as a gene having a region encoding a DH/PH domain that is a characteristic domain for Rho-GEF. The long-chain cDNA library derived from human brain tissue is a cDNA library comprising cDNA clones whose complete base sequence was determined after isolating cDNA fragments by dbEST (database of Expressed Sequence Tags) analysis from a cDNA library, constructed by an ordinary method employing commercially available polyA$^+$RNA derived from human brain tissue, fetal brain tissue, and cerebral hippocampus tissue as a starting material.

The specific embodiment of the polynucleotide, according to the present invention, can be a polynucleotide shown by the nucleotide sequence set forth in SEQ ID NO: 1 in the sequence listing, or by the complementary nucleotide sequence thereof. The polynucleotide shown by the nucleotide sequence set forth in SEQ ID NO: 1 is 4977 bp long and contains an open reading frame (ORF) encoding 1340 amino acid residues (SEQ ID NO: 2). The region in the nucleotide sequence set forth in SEQ ID NO: 1, which consists of the nucleotides from the $602^{nd}$ to the $1126^{th}$, encodes a DH domain consisting of 175 amino acid residues from the $97^{th}$ valine (Val) to the $271^{st}$ aspartic acid (Asp), of the amino acid sequence set forth in SEQ ID NO: 2. The region in the nucleotide sequence set forth in SEQ ID NO: 1, which consists of the nucleotides from the $1202^{nd}$ to the $1495^{th}$, encodes a PH domain consisting of 98 amino acid residues from the $297^{th}$ leucine (Leu) to the $394^{th}$ leucine (Leu) of the amino acid sequence set forth in SEQ ID NO: 2. The region in the nucleotide sequence set forth in SEQ ID NO: 1, which consists of the nucleotides from the $602^{nd}$ to the $1495^{th}$, encodes a DH/PH domain consisting of 298 amino acid residues from the $97^{th}$ valine (Val) to the $394^{th}$ leucine (Leu) of the amino acid sequence set forth in SEQ ID NO: 2. A polynucleotide encoding a protein shown by the amino acid sequence set forth in SEQ ID NO: 2, or a polynucleotide shown by the complementary nucleotide sequence of the polynucleotide is also included in the scope of the present invention.

The embodiment of the polynucleotide according to the present invention can also be a polynucleotide shown by the nucleotide sequence set forth in SEQ ID NO: 3, or SEQ ID NO: 5, or by the complementary nucleotide sequence thereof. The polynucleotide shown by the nucleotide sequence set forth in SEQ ID NO: 3 is a polynucleotide shown by the nucleotide sequence from the $581^{st}$ nucleotide to the $1675^{th}$ nucleotide, of the nucleotide sequence set forth in SEQ ID NO: 1. The polynucleotide shown by the nucleotide sequence set forth in SEQ ID NO: 5, is a polynucleotide which consists of a polynucleotide shown by the nucleotide sequence set forth in SEQ ID NO: 3, and an oligonucleotide (SEQ ID NO: 19) ligated to its 5'-terminal. The oligonucleotide (SEQ ID NO: 19) consists of a kozak consensus sequence (hereinafter, may be referred to as a kozak sequence) and a methionine codon. The polynucleotide shown by the nucleotide sequence set forth in SEQ ID NO: 3, or SEQ ID NO: 5, contains a region encoding a DH/PH domain that is an active domain of Rho-GEF.

The polynucleotide according to the present invention is preferably a polynucleotide that encodes a protein having a function of accelerating the activation of a Rho family protein, or a polynucleotide shown by the complementary nucleotide sequence of the polynucleotide. For example, a polynucleotide shown by the nucleotide sequence set forth in SEQ ID NO: 5, or the complementary nucleotide sequence thereof, is preferable for such a polynucleotide. Co-expression of the polynucleotide shown by the nucleotide sequence set forth in SEQ ID NO: 5 with a gene encoding a Rho family protein in a mammalian cell, resulted in the accelerated activation of the Rho family protein (See Example 4). Thus, it can be considered that a protein encoded by the polynucleotide shown by the nucleotide sequence set forth in SEQ ID NO: 5, accelerates the activation of a Rho family protein. The polynucleotide shown by the nucleotide sequence set forth in SEQ ID NO: 5, is a polynucleotide which consists of a polynucleotide (SEQ ID NO: 3) shown by the nucleotide sequence from the 580 nucleotide to the $1675^{th}$ nucleotide of the nucleotide sequence set forth in SEQ ID NO: 1, and an oligonucleotide (SEQ ID NO: 19) ligated to its 5'-terminal. The oligonucleotide (SEQ ID NO: 19) consists of a kozak sequence and a methionine codon. The protein encoded by the polynucleotide shown by the nucleotide sequence set forth in SEQ ID NO: 5 is a protein encoded by a polynucleotide shown by the nucleotide sequence set forth in SEQ ID NO: 3, and includes a methionine added to its N-terminal, by a peptide bond. Because the added oligonucleotide (SEQ ID NO: 19) consisting of a kozak sequence and a methionine codon was for the purpose of expressing the polynucleotide shown by the nucleotide sequence set forth in SEQ ID NO: 3, it does not affect the function of the expressed protein. Therefore, the present inventors believe that the polynucleotide shown by the nucleotide sequence set forth in SEQ ID NO: 3, encodes a protein having a function of accelerating the activation of a Rho family protein, although it does not have the oligonucleotide (SEQ ID NO: 19) consisting of a kozak sequence and a methionine codon.

The protein encoded by the polynucleotide shown by the nucleotide sequence set forth in SEQ ID NO: 3, and the protein encoded by the polynucleotide shown by the nucleotide sequence set forth in SEQ ID NO: 5, both accelerate the activation of a Rho family protein as described above. The protein encoded by the polynucleotide shown by the nucleotide sequence set forth in SEQ ID NO: 3 can be, for example, a protein shown by the amino acid sequence set forth in SEQ ID NO: 4. The protein encoded by the polynucleotide shown by the nucleotide sequence set forth in SEQ ID NO: 5 can be, for example, a protein shown by the amino acid sequence set forth in SEQ ID NO: 6. A polynucleotide encoding a protein shown by the amino acid sequence set forth in SEQ ID NO: 4, or SEQ ID NO: 6, or a polynucleotide shown by the complementary nucleotide sequence of the polynucleotide, is also included in the scope of the present invention.

Since the polynucleotide shown by the nucleotide sequence set forth in SEQ ID NO: 3 can be considered to encode a protein that accelerates the activation of a Rho family protein, the present inventors believe that a polynucleotide containing the polynucleotide shown by the nucleotide sequence set forth in SEQ ID NO: 3, also encodes a protein that accelerates the activation of a Rho family protein. Further, the present inventors believe that a polynucleotide containing the polynucleotide encoding the protein shown by the amino acid sequence set forth in SEQ ID NO: 4, also encodes a protein that accelerates the activation of a Rho family protein. The polynucleotide containing the polynucleotide shown by the nucleotide sequence set forth in SEQ ID NO: 3 can be, for example, the polynucleotide shown by the nucleotide sequence set forth in SEQ ID NO: 1. The present inventors believe that the polynucleotide shown by the nucleotide sequence set forth in SEQ ID NO: 1, also encodes a protein that accelerates the activation of a Rho family protein.

A polynucleotide containing the polynucleotide shown by the nucleotide sequence set forth in SEQ ID NO: 3, a complementary nucleotide sequence, a polynucleotide containing the polynucleotide encoding the protein shown by the amino acid sequence set forth in SEQ ID NO: 4, and the polynucleotide shown by the complementary nucleotide sequence of the polynucleotide, are also included in the scope of the present invention. A polynucleotide that also encodes a protein capable of accelerating the activation of a Rho family protein is more preferable for such a polynucleotide. Further, a polynucleotide having a DH/PH domain coding region is still more preferable for such a polynucleotide.

A Rho family protein, the activation of which is accelerated by the protein encoded by the polynucleotide according to the present invention, may be exemplified by Cdc42 proteins, RhoA proteins, Rac1 proteins, and preferable by Cdc42 proteins. A Rho family protein is not limited to these specific examples, and can be any Rho family protein as long as its activation is accelerated by the protein encoded by the present polynucleotide. The function of the protein encoded by the present polynucleotide, to accelerate the activation of a Rho family protein, can be measured by using, for example, an effector pull-down assay (see Example 4).

Cdc42, RhoA and Rac1 are proteins respectively shown by the amino acid sequences set forth in SEQ ID NO: 21, SEQ ID NO: 23 and SEQ ID NO: 25. Cdc42 gene, RhoA gene and Rac1 gene are genes respectively shown by the nucleotide sequences set forth in SEQ ID NO: 20, SEQ ID NO: 22 and SEQ ID NO: 24. Cdc42, RhoA, Rac 1 and their genes are not limited to the specific examples shown by the aforementioned sequences. They can be a protein or a gene with a mutation of one or several sites in the aforementioned sequence as long as it has a function of Cdc42, RhoA and Rac1 generally known. Further, a mutant can be prepared for use by introducing a mutation into one or several sites of the aforementioned sequence in order to increase or decrease the function of the protein and the gene. Cdc42, RhoA and Rac1 can be produced, for example, by culturing a transformant that was prepared by transfecting with a recombinant vector containing the corresponding gene by using well-known gene manipulation techniques.

A polynucleotide according to the present invention can be prepared based on the sequence information concerning the specific example provided by the present invention, such as the polynucleotide shown by the nucleotide sequence set forth in SEQ ID NO: 1 in the sequence listing. The production of the polynucleotide can be carried out easily by using gene manipulation techniques that are well known per se (refer to Non-Patent References 9 and 10).

Specifically, the polynucleotide of the present invention can be acquired by preparing a cDNA library in accordance with an ordinary method, from a suitable source in which expression of the polynucleotide was found, and then selecting a desired clone from the cDNA library. As a cDNA source, various kinds of cells and tissues in which expression of the present polynucleotide was found, or cultured cells derived from these cells and tissues, for example, cells derived from human brain tissue, or the like, can be used. Isolation of total RNA from these sources, isolation and purification of mRNA, acquisition of cDNA, the cloning thereof, and the like, can each be performed in accordance with an ordinary method. It is also possible to use a cDNA library that was constructed from commercially available polyA$^+$ RNA derived from human brain tissue, fetal brain tissue, or cerebral hippocampus tissue. A method for selecting a desired clone from a cDNA library is not particularly limited, and any methods generally used can be employed. For example, selection of a desired clone can be performed by using a probe or primer capable of selectively hybridizing to the present polynucleotide. Specifically, a plaque hybridization method, colony hybridization method, or the like, which uses a probe capable of selectively hybridizing to the present polynucleotide, or a combination of these methods, can be employed. As a probe, a polynucleotide chemically synthesized based on the sequence information of the present polynucleotide, and the like, can generally be used. The present polynucleotide prepared, or a polynucleotide shown by the partial nucleotide sequence of the present polynucleotide, is suitable for use as a probe, as well. Furthermore, a sense primer and an anti-sense primer, which were designed based on the sequence information of the present polynucleotide, can also be used as such a probe.

Selection of a desired clone from a cDNA library can be performed, for example, by detecting the expression of the protein in each clone, utilizing a known protein expression system, and further determining a biological function of the protein as an indicator. A function of the protein encoded by the present polynucleotide, for example, can be the function of binding to a Rho family protein, such as RhoA, Cdc42, Rac1, and the like, and can be accelerating the activation of a Rho family protein. Any known expression system can be used as a protein expression system. For example, a cell free protein expression system can be conveniently used as such a system (Non-Patent Reference 11).

The phrase "activation of a Rho family protein" as used herein, means an exchange reaction, wherein guanosine 5'-diphosphate (GDP), that is bound to a Rho family protein, is exchanged for guanosine 5'-triphosphate (GTP). This exchange reaction comprises a dissociation reaction of GDP from a Rho family protein, and a binding reaction of GTP to the resultant Rho family protein, without a nucleotide being bound. The phrase "accelerating the activation of a Rho family protein" means accelerating the dissociation reaction of GDP from a Rho family protein, which is a rate-determining step of this exchange reaction.

The polynucleotide according to the present invention can be also prepared preferably by using a DNA/RNA amplification method. For example, a polymerase chain reaction can be used (hereinafter, may be abbreviated as PCR: Non-Patent References 12 to 14). When the full-length cDNA is difficult to obtain from a cDNA library, a RACE method (Non-Patent Reference 15), particularly the 5'-RACE method (Non-Patent Reference 16), or the like, can be suitably employed. Primers to be used for PCR can be suitably designed based on the nucleotide sequence information of the polynucleotide, and can be obtained by synthesis in accordance with any conventional method. Isolation and purification of amplified DNA/RNA fragments can be carried out according to any conventional method, such as gel electrophoresis, or the like.

A determination of the nucleotide sequence of DNA thus obtained can be carried out by any conventional method, such as the dideoxy method (Non-Patent Reference 17), and the Maxam-Gilbert method (Non-Patent Reference 18), or by simply using a commercially available sequencing kit, or the like.

The polynucleotides according to the present invention are not limited to the aforementioned polynucleotides, and can include polynucleotides having a sequence homology with the aforementioned polynucleotides and encoding proteins capable of accelerating the activation of a Rho family protein, or polynucleotides shown by the complementary nucleotide sequences of the polynucleotides. A suitable sequence homology with the entire base sequence is normally about 50% or more, preferably about 70% or more, more preferably about 80% or more, and even more preferably about 90% or more. Further, polynucleotides having a DH/PH domain coding region are still more preferable for such polynucleotides. A suitable sequence homology with the DH/PH domain coding region is preferably about 70% or more, more preferably about 80% or more, and even more preferably about 90% or more. In addition, it is still more preferable that the DH/PH domain has its specific function, such as a function of accelerating the activation of a Rho family protein.

The polynucleotides of the present invention include polynucleotides shown by a nucleotide sequence with a mutation, such as deletion, substitution, addition or insertion, of one or more nucleotides in the nucleotide sequences of the aforementioned DNA, or polynucleotides shown by complementary nucleotide sequences. The number of mutated nucleotides is, for example, from 1 to 100, preferably from 1 to 30, more preferably from 1 to 20, even more preferably from 1 to 10, and still more preferably from 1 to several in number. The extent of mutation, the position of a mutation, and the like, are not particularly limited as long as the polynucleotides with mutations encode proteins functioning to accelerate the activation of a Rho family protein, and/or preferably proteins having DH/PH domain. The polynucleotides with mutations may be natural polynucleotides or may be mutated polynucleotides. Further, they also may be polynucleotides prepared by introducing a mutation into a natural gene. Techniques for introducing a mutation are known in the art. For example, site-directed mutagenesis, genetic homologous recombination, primer extension, PCR, and the like, can be used independently or in suitable combinations. Specifically, for example, a method described in publications (Non-Patent References 9 and 10), or a modified method thereof, can be used for conducting the introduction of a mutation. In addition, Ulmer's techniques (Non-Patent Reference 12) can also be utilized.

The polynucleotides of the present invention can also be polynucleotides that hybridize to the aforementioned polynucleotides under stringent conditions. A hybridization condition can be found, for example, in a method described in publications (Non-Patent Reference 9), or the like. More specifically, the phrase "under stringent conditions" refers to, for example, a condition of heating at 42° C. in a solution containing 6×SSC, 0.5% SDS and 50% formamide, and then washing at 68° C. in a solution containing 0.1×SSC and 0.5% SDS. Such polynucleotides are not required to have complementary sequences with the present polynucleotides as long as they hybridize to the present polynucleotides. It is desirable that the encoding proteins are preferably proteins functioning to accelerate the activation of a Rho family protein, and/or more preferably proteins having a DH/PH domain.

The polynucleotides of the present invention also include oligonucleotides shown by a partial nucleotide sequence of a given region of the aforementioned polynucleotides. The minimum unit of such an oligonucleotide consists of consecutive nucleotides within the region, preferably of 5 or more, more preferable of 10 or more, and even more preferably of 20 or more consecutive nucleotides. These oligonucleotides can be prepared by designing a desired sequence based on the nucleotide sequence information of the present polynucleotides, and then synthesizing them using a well-known chemical synthesis method. An automated DNA/RNA synthesizer can be conveniently used for preparing the oligonucleotides. These oligonucleotides can be used, for example, as primers for amplifying the present genes or the present gene fragments, and as probes for detecting the present genes or their transcription products thereof.

Oligonucleotides shown by a partial nucleotide sequence with a given region of the polynucleotides according to present invention can be preferably exemplified by an oligonucleotide shown by the nucleotide sequence set forth in SEQ ID NO: 7, SEQ ID NO: 8, SEQ ID NO: 9 or SEQ ID NO: 10, in the sequence listing.

The polynucleotides of the present invention are human derived polynucleotides. However, the present invention includes polynucleotides derived from a mammal, for example, a polynucleotide derive from mouse, horse, sheep, cow, dog, monkey, cat, bear, rat, rabbit or the like, as long as the polynucleotide is a polynucleotide having sequence homology with the present polynucleotides, and that encode a protein that accelerates the activation of a Rho family protein, preferably polynucleotides having a DH/PH coding domain.

The polynucleotides of the present invention also may have a desired gene at the 5'-terminal side or the 3'-terminal side thereof, as long as the expression of the polynucleotides or the function of proteins encoded by the polynucleotides, for example, the function of accelerating the activation of a Rho family protein, is not inhibited. A gene capable of being added to the present polynucleotide can be specifically exemplified by the genes of enzymes, such as glutathione S-transferase (GST), β-galactosidase (β-Gal), horseradish peroxidase (HRP) or alkaline phosphatase (ALP), or of tag peptides such as His-tag, Myc-tag, HA-tag, FLAG-tag or Xpress-tag. The present polynucleotides can be added to one of these genes, or to multiple kinds of these genes, in combination. Addition of these genes can be performed by using conventional gene manipulation techniques, and is useful to facilitate detection of a gene or mRNA.

Another aspect of the present invention relates to recombinant vectors containing a polynucleotide of the present invention. The recombinant vectors can be prepared by inserting one or more of the present polynucleotides into a suitable vector DNA.

The vector DNA is not particularly limited as long as it can be replicated within a host, and can be suitably selected in accordance with the kind of host and purpose of use. The vector DNA may be vector DNA obtained by extracting natural DNA, or may be vector DNA lacking a part of DNA other than a segment necessary for replication. Typical vector DNAs include, for example, a vector DNA derived from a plasmid, a bacteriophage or a virus. A plasmid DNA can be exemplified by a plasmid derived from *Escherichia coli*, a plasmid derived from *Bacillus subtilis*, or a plasmid derived from yeast. A bacteriophage DNA can be exemplified by a λ phage. Vector DNA derived from a virus can be exemplified by a vector derived from an animal virus, such as a retrovirus, vaccinia virus, adenovirus, papovavirus, SV 40, fowlpox virus, and pseudorabies virus, or a vector derived from an insect virus such as baculovirus. Further, vector DNA derived from a transposon, an insertion element, a yeast chromosome element, or the like, may be used. Alternatively, a vector DNA prepared by combining two or more of these, for example, a vector DNA (cosmid, phagemid or the like) prepared by combining genetic elements of a plasmid and a bacteriophage, may be used.

Any vector DNA can be used in accordance with the desired purpose, for example, an expression vector, cloning vector or the like. The recombinant expression vector containing the polynucleotide of the present invention is useful for the production of proteins encoded by the present polynucleotides.

It is necessary for the polynucleotide of the present invention to be incorporated into vector DNA in such a way as to allow the function of the polynucleotide to appear. The vector DNA contains at least one of the present polynucleotides and a promoter, as construction elements. In addition to these elements, as desired, a genetic sequence that encodes information relating to replication and control, may be incorporated in combination into the vector DNA, by using a well-known method. Such a genetic sequence can be exemplified by a ribosome binding sequence, terminator, signal sequence, cis element such as an enhancer, splicing signal, and a selective marker such as dihydrofolate reductase gene, ampicillin-resistant gene and neomycin-resistant gene. The vector DNA may contain one or more kinds of genetic sequences selected from the aforementioned members.

As a method of incorporating the polynucleotide, according to the present invention, into a vector DNA, any known method can be employed. For example, a method may be used which comprises cleaving a gene containing the present polynucleotide at specific sites, by treating it with suitable restriction enzymes, and then mixing it with a similarly treated vector DNA, for ligation using a ligase. Alternatively, a desired recombinant vector may be prepared by using a method that comprises ligating one of the present polynucleotides with a suitable linker, and then inserting it into the multi-cloning site of a vector, suitable for the desired purpose.

A further aspect of the present invention relates to transformants obtained by transforming a host with the recombinant vectors according to the present invention. A transformant, prepared by introducing a recombinant expression vector that contains a polynucleotide according to the present invention, is useful for producing a protein encoded by the present polynucleotides. The present transformants may further incorporate one or more kinds of vector DNAs, each containing a desired gene other than the present polynucleotides. A vector DNA that contains a desired gene other than a present polynucleotide, can be exemplified by vector DNA that contains a gene encoding a Rho family protein, such as, RhoA, Rac1, Cdc42, or the like. A transformant prepared by transfecting with both of the expression vectors, one of which contains a present polynucleotide and the other contains a gene encoding a Rho family protein, may be used for a method of identifying a compound that inhibits the acceleration of the activation of a Rho family protein, by a protein encoded by a present polynucleotide. Such a transformant can be preferably exemplified by a transformant prepared by transfecting with a recombinant vector according to the present invention, and a recombinant vector that contains a polynucleotide encoding Cdc42.

Any suitable prokaryotes and eukaryotes can be employed as a host. Examples of suitable prokaryotes include bacteria belonging to the *Escherichia* genus, such as, *Escherichia coli*, bacteria belonging to the *Bacillus* genus, such as, *Bacillus subtilis*, bacteria belonging to the *Pseudomonas* genus, such as, *Pseudomonas putida*, and bacteria belonging to the *Rhizobium* genus, such as, *Rhizobium meliloti*. Examples of suitable eukaryotes include yeasts, insect cells, and mammalian cells. Yeasts can be exemplified by *Saccharomyces cerevisiae* and *Schizosaccharomyces pombe*. Insect cells can be exemplified by Sf9 cells and Sf2 cells. Mammalian cells can be exemplified by monkey kidney-derived cells, such as COS cells, Vero cells, Chinese hamster ovary cells (CHO cell), mouse L cells, rat GH3 cells, human FL cells, human 293EBNA cells, and *Xenopus laevis* oocytes. It is preferable to use mammalian cells, and more preferable to use 293EBNA cells.

All known methods can be used for introducing a vector DNA into a host. For example, a standard method described in publications, for example, Non-Patent Reference 9, may be utilized. When gene stability is a consideration, it is preferable to use a method that integrates the gene onto a chromosome. Meanwhile, it is convenient to use an autonomous replication system that utilizes an extranuclear gene. Specifically, calcium phosphate transfection, DEAE-dextran mediated transfection, microinjection, cationic lipid-mediated transfection, electroporation, transduction, scrape loading, ballistic introduction, infection, and the like, may be mentioned.

When employing a prokaryote as a host, it is preferable to use a recombinant vector which is capable of autonomous replication within the bacterium, and is also composed of a promoter, a ribosomal binding sequence, the polynucleotide of the present invention, and a transcription termination sequence. It may also contain a gene that regulates the promoter. When employing bacteria as a host, any promoter may be used as long as it can lead to expression in bacteria, such as *Escherichia coli*. For example, a promoter derived from *Escherichia coli* or a phage can be used, such as a trp promoter, lac promoter, PL promoter or PR promoter. An artificially designed and modified promoter such as a tac promoter may also be used. A method of introducing a recombinant vector into bacteria is not particularly limited, and any methods that introduce DNA into bacteria can be employed. Preferable examples of such a method include using calcium ions, electroporation, or the like.

When employing a mammalian cell as a host, it is preferable to use the recombinant vector which is capable of autonomous replication within the cell, and is also composed of a promoter, RNA splice site, a polynucleotide of the present invention, polyadenylated site and a transcription termination sequence. As desired, it may also contain an origin of replication. A SRα promoter, SV 40 promoter, LTR promoter, CMV promoter, and the like, can be used as a promoter. An early gene promoter of cytomegalovirus, and the like, may be used, as well. As a method of introducing the recombinant vector into a mammalian cell, preferably, for example, electroporation, the calcium phosphate technique, lipofection, or the like, may be used. A most preferable method to be used may be lipofection.

When using yeast as a host, the promoter is not particularly limited as long as it can lead to expression in yeast. Examples of such a promoter include the gall promoter, gal 10 promoter, heat shock protein promoter, MFα1 promoter, PHOS promoter, PGK promoter, GAP promoter, ADH promoter, and AOX1 promoter. A method of introducing a recombinant vector into yeast is not particularly limited as long as it is a method that introduces the DNA into the yeast. Preferable examples of such a method include electroporation, a spheroplast method, a lithium acetate method or the like.

When using an insect cell as a host, it is preferable to use a calcium phosphate technique, lipofection, or electroporation for a method of introducing a recombinant vector.

A further aspect of the present invention relates to proteins encoded by a polynucleotide according to the present invention.

A specific embodiment of a protein according to the present invention can be, for example, a protein encoded by the polynucleotide shown by the nucleotide sequence set forth in SEQ ID NO: 1. Such a protein can be a protein shown by the amino acid sequence set forth in SEQ ID NO: 2. The protein has a DH domain in its amino acid sequence from the 97$^{th}$ valine (Val) to the 271$^{st}$ aspartic acid (Asp), and a PH domain in its amino acid sequence from the 297$^{th}$ leucine (Leu) to the 394$^{th}$ leucine (Leu). Thus, the protein has a DH/PH domain in its amino acid sequence from the 97$^{th}$ valine (Val) to the 394$^{th}$ leucine (Leu).

An embodiment of a protein according to the present invention can also be a protein encoded by the polynucleotides shown by the nucleotide sequences set forth in SEQ ID NO: 3 or SEQ ID NO: 5. The protein encoded by the polynucleotide shown by the nucleotide sequence set forth in SEQ ID NO: 3 can be a protein shown by the amino acid sequence set forth in SEQ ID NO: 4. In addition, the protein encoded by the polynucleotide shown by the nucleotide sequence set forth in SEQ ID NO: 5 can be a protein shown by the amino acid sequence set forth in SEQ ID NO: 6. The amino acid sequence set forth in SEQ ID NO: 4 corresponds to the amino acid sequence set forth in SEQ ID NO: 2 from the 90$^{th}$ lysine (Lys) to the 454$^{th}$ leucine (Leu). In addition, the amino acid sequence set forth in SEQ ID NO: 6 is an amino acid sequence consisting of the amino acid sequence set forth in SEQ ID NO: 4, and a methionine added to its N-terminal by a peptide bond. Namely, the protein shown by each of these amino acid sequences contains a DH/PH domain.

A protein according to the present invention is preferably a protein having the function of accelerating the activation of a Rho family protein. For example, a protein encoded by the polynucleotide shown by the nucleotide sequence set forth in SEQ ID NO: 5, is preferable for such a protein. Co-expression of the polynucleotide shown by the nucleotide sequence set forth in SEQ ID NO: 5, with a gene encoding a Rho family protein, such as RhoA, Cdc42, and Rac1 in a mammalian cell, resulted in observing by a pull-down assay, that the protein encoded by the polynucleotide bound to each of the Rho family proteins (See Example 3). Further, the activation of Cdc42 was accelerated in the cell (See Example 4). Based on these findings, it can be considered that a protein encoded by the polynucleotide, shown by the nucleotide sequence set forth in SEQ ID NO: 5 binds to a Rho family protein, and accelerates the activation thereof. A protein encoded by the polynucleotide shown by the nucleotide sequence set forth in SEQ ID NO: 5, is a protein which consists of a protein encoded by the polynucleotide shown by the nucleotide sequence set forth in SEQ ID NO: 3, and a methionine added to its N-terminal by a peptide bond. The protein encoded by the polynucleotide shown by the nucleotide sequence set forth in SEQ ID NO: 5, is a protein obtained by adding an oligonucleotide (SEQ ID NO: 19), consisting of a kozak sequence and a methionine codon, to the 5'-terminal of the polynucleotide shown by the nucleotide sequence set forth in SEQ ID NO: 3, for the purpose of expressing the polynucleotide. The added methionine does not significantly affect the function of the expressed protein. Therefore, the protein encoded by the polynucleotide shown by the nucleotide sequence set forth in SEQ ID NO: 3, is believed to bind to a Rho family protein and accelerate the activation thereof, even without a methionine added to the N-terminal.

Thus, the protein encoded by the polynucleotide shown by the nucleotide sequence set forth in SEQ ID NO: 3, is believed to bind to a Rho family protein and accelerate the activation thereof in a similar manner as the protein encoded by the polynucleotide shown by the nucleotide sequence set forth in SEQ ID NO: 5. In addition, a DH/PH domain that is contained in these proteins is known to be an important domain concerning the activation of a Rho family protein.

A protein that contains the protein encoded by the polynucleotide shown by the nucleotide sequence set forth in SEQ ID NO: 3, is believed to also bind to Rho family proteins, and accelerate the activation thereof. Such a protein can be a protein encoded by a polynucleotide that contains the polynucleotide shown by the nucleotide sequence set forth in SEQ ID NO: 3. Further, since the polynucleotide shown by the nucleotide sequence set forth in SEQ ID NO: 3 encodes the protein shown by the amino acid sequence set forth in SEQ ID NO: 4, a protein encoded by a polynucleotide that contains the polynucleotide encoding the protein shown by the amino acid sequence set forth in SEQ ID NO: 4, can be an example of such a protein. Specifically, a protein encoded by a polynucleotide that contains the polynucleotide shown by the nucleotide sequence set forth in SEQ ID NO: 3, may be exemplified by a protein encoded by the polynucleotide shown by the nucleotide sequence set forth in SEQ ID NO: 1. A protein encoded by the polynucleotide shown by the nucleotide sequence set forth in SEQ ID NO: 1, can be exemplified by a protein shown by the amino acid sequence set forth in SEQ ID NO: 2. All of these proteins exemplified herein are believed to bind to a Rho family protein, and accelerate the activation thereof.

The present invention includes a protein that is encoded by a polynucleotide that contains the polynucleotide shown by the nucleotide sequence set forth in SEQ ID NO: 3, or by its complementary nucleotide sequence, or that is encoded by a polynucleotide that contains the polynucleotide encoding the protein shown by the amino acid sequence set forth in SEQ ID NO: 4, or by its complementary nucleotide sequence, each of which is a polynucleotide encoding a protein that accelerates the activation of a Rho family protein.

The protein according to the present invention is not limited to a protein as exemplified above, and any protein is included in the scope of the present invention as long as it is encoded by a polynucleotide according to the present invention. Preferably, a protein that is encoded by a polynucleotide according to the present invention, and that has the function of accelerating the activation of a Rho family protein, may be mentioned. Such a protein can be exemplified by a protein that is encoded by a polynucleotide shown by a nucleotide sequence having a homology of at least 70% with the nucleotide sequence of any one of the polynucleotides selected from the group consisting of the following: a polynucleotide shown by the nucleotide sequence set forth in SEQ ID NO: 1, or its complementary nucleotide sequence; a polynucleotide encoding the protein shown by the amino acid sequence set forth in SEQ ID NO: 2, or a polynucleotide shown by the complementary nucleotide sequence of the polynucleotide; a polynucleotide shown by the nucleotide sequence set forth in SEQ ID NO: 3, or SEQ ID NO: 5, or by a complementary nucleotide sequence; and a polynucleotide encoding a protein shown by the amino acid sequence set forth in SEQ ID NO: 4, or SEQ ID NO: 6, or a polynucleotide shown by the complementary nucleotide sequence of the polynucleotide, where the protein accelerates the activation of a Rho family protein. Further, the present protein also includes a protein that is encoded by a polynucleotide shown by a nucleotide sequence with a mutation, such as deletion, substitution, addition or the like, or an induced mutation, of one or more nucleotides in the nucleotide sequence of any one of the polynucleotides selected from the aforementioned polynucleotide group, where the protein is encoded by a polynucleotide encoding a protein that accelerates the activation of a Rho family protein. Furthermore, the present protein may also include a protein encoded by a polynucleotide that hybridizes to any one of the polynucleotides selected from the aforementioned polynucleotide group, under stringent conditions, and encodes a protein that accelerates the activation of a Rho family protein.

A protein according to the present invention can be more specifically, for example, a protein that has a sequence homology with the protein shown by the amino acid sequence set forth in SEQ ID NO: 2, SEQ ID NO: 4, or SEQ ID NO: 6, and that has the function of accelerating the activation of a Rho family protein. A suitable sequence homology with the amino acid sequence is normally about 50% or more, preferably about 70% or more, more preferably about 80% or more, and even more preferably about 90% or more. Further, a protein having a DH/PH domain is still more preferable for such a protein. A suitable sequence homology with the DH/PH domain is preferably about 70% or more, more preferably about 80% or more, and even more preferably about 90% or more. In addition, it is still more preferable that the DH/PH domain has a specific function of accelerating the activation of a Rho family protein. Further, a protein of the present invention includes a protein that is shown by an amino acid sequence with a mutation, such as deletion, substitution, addition, or the like, of one or more amino acids in the amino acid sequence set forth in SEQ ID NO: 2, SEQ ID NO: 4, or SEQ ID NO: 6, and has the function of accelerating the activation of a Rho family protein. The number of mutated amino acids is, for example from 1 to 100, preferably from 1 to 30, more preferably from 1 to 20, even more preferably from 1 to 10, and still more preferably from 1 to several in number. The extent of mutation, the position of a mutation, and the like, of the amino acid are not particularly limited as long as a protein with a mutation has the function of accelerating the activation of a Rho family protein, and preferably is a protein having a DH/PH domain. Such a protein with a mutation may be a protein generated in nature, for example, due to mutation or post translational modification. Further, it also may be a protein prepared by introducing a mutation into a natural gene. Techniques for introducing a mutation are known in the art. For example, known gene manipulation techniques can be used for preparation. When introducing a mutation, in view of avoiding a change in the fundamental properties (such as physical properties, function, physiological activity, and immunological activity) of the protein, mutual substitution among homologous amino acids (polar amino acids, non-polar amino acids, hydrophobic amino acids, hydrophilic amino acids, positively-charged amino acids, negatively-charged amino acids and aromatic amino acids or the like) may be readily conceived.

A protein according to the present invention further includes a protein shown by a partial sequence of the aforementioned protein. For example, a protein that is shown by a partial sequence of the protein shown by the amino acid sequence set forth in SEQ ID NO: 2, SEQ ID NO: 4, or SEQ ID NO: 6, is also included in the scope of the present invention. The minimum unit of such a protein consists of consecutive amino acids, preferably 5 or more, more preferably 8 or more, even more preferably 12 or more, or 15 or more.

A protein of the present invention is a human derived protein. However, the present invention includes proteins derived from mammals, for example, proteins derived from a mouse, horse, sheep, cow, dog, monkey, cat, bear, rat, rabbit, or the like, as long as the protein is a protein having a sequence homology with the present proteins, and having a function of accelerating the activation of a Rho family protein, and preferably is a protein having a DH/PH domain.

A protein of the present invention may be a protein prepared from a cell in which a gene encoding the present protein is expressed by means of a gene manipulation technique, or from any suitable biological sample. A protein also may be a product of a cell-free synthesis system, or a chemical synthesis product. These can be subsequently further purified for use. In addition, the present protein may be a protein being expressed in a cell that contains a gene encoding the present protein. The cell may be a transformant prepared by transfecting a vector that contains a gene encoding the present protein.

A protein of the present invention can be modified to the extent that no significant functional change is involved, such as modification of its constituent amino groups, carboxyl groups, or the like, or by an amidation or the like. A present protein can also be labeled with the other protein, or the like, that is added to the N-terminal or C-terminal, directly or indirectly, via a linker peptide, or the like, or by means of gene manipulation techniques, or the like. Labeling is preferably conducted in a way not to inhibit the fundamental properties of the present protein. Even more preferably, labeling is conducted in a way not to inhibit the function of the present protein of accelerating the activation of a Rho family protein. A substance used for labeling (a labeling substance) can be exemplified by enzymes such as GST, β-Gal, HRP, ALP, or the like, tag peptides such as His-tag, Myc-tag, HA-tag, FLAG-tag, Xpress-tag or the like, fluorescent substances, such as fluorescein isothiocyanate, phycoerythrin or the like, a maltose binding protein, an immunogloblin Fc-fragment, biotin, or the like. However, it is not limited to these specific examples. Labeling can also be carried out using a radioactive isotope. One or more kinds of labeling substances in combination can be added to the present protein. These labeling substances allow the detection and/or purification of the present protein to become easier, by measuring the substance itself, or the function thereof. In addition, these substances allow, for example, the detection of the binding of the present protein to the other protein, and the measurement of the function of the present protein.

A further aspect of the present invention relates to a method of producing a protein according to the present invention. The present protein can be prepared, for example, by standard gene manipulation techniques (refer to Non-Patent References 9, 10, 12, 13, and the like) based on the nucleotide sequence information of a gene encoding the present protein. For example, a cDNA library may first be prepared from various kinds of cells or tissues in which the expression of the present polynucleotide was found, or cultured cells derived from these cells and tissues, in accordance with conventional methods. Then, the polynucleotide encoding the present protein may be amplified from the cDNA library, by using a primer that selectively hybridizes to the gene encoding the protein. The amplified polynucleotide may be used for the expression induction by using known gene manipulation techniques resulting in the production of the present protein.

Specifically, for example, the present proteins can be produced by culturing the transformants according to the present invention, and then collecting the present proteins from the culture product obtained. The transformant can be cultured according to known culture conditions and culture methods that are suitable for each host. Cultivation can be carried out by employing an indicator, such as the present proteins themselves that are expressed by the transformant, or a function thereof. For example, a function can be accelerating the activation of a Rho family protein. Alternatively, cultivation may be carried out by employing such an indicator as the present proteins themselves produced in a host or outside a host, or the amount of the protein. Otherwise, subculturing or batch culturing may be carried out by employing such an indicator as the amount of transformant in the culture medium.

When the proteins according to the present invention are expressed in a transformant, or on its cell membrane, the proteins may be extracted from the disrupted transformant. Further, when the present proteins are secreted outside the transformant, the cultured medium can be used as is, or the cultured medium, after removing the transformant by centrifugation or the like, can be used.

As desired, the proteins according to the present invention can be isolated and/or purified from a cultured medium of the transformant or from the transformant, by various isolation methods that utilize the physical properties or chemical properties thereof. Isolation and/or purification can be carried out by employing an indicator such as a function of the present proteins, for example, the function of accelerating the activation of a Rho family protein. Examples of isolation methods include ammonium sulfate precipitation, ultrafiltration, gel chromatography, ion-exchange chromatography, affinity chromatography, high performance liquid chromatography, and dialysis. These methods may be used independently, or in suitable combinations. It is preferable to employ a method of specific absorption using specific antibodies to the present proteins which are prepared based on the amino acid information of the proteins. For example, affinity chromatography that utilizes a column bound with specific antibodies can be used.

The proteins of the present invention can also be produced according to conventional chemical synthesis methods. For example, solid phase synthesis, solution phase synthesis, and the like, are known as chemical synthesis methods for proteins, and any of these methods can be used. These kinds of protein synthesis methods more specifically include a so-called stepwise elongation method that sequentially binds each amino acid, one at a time, to elongate a chain based on amino acid sequence information, and a fragment condensation method that previously synthesizes fragments consisting of several amino acids, and subsequently subjects the respective fragments to a coupling reaction. The present proteins can be synthesized by either of these methods. A condensation method used for the aforementioned protein synthesis methods can also be carried out according to conventional methods. Examples of condensation methods include an azide method, mixed anhydride method, DCC method, active ester method, oxidation-reduction method, DPPA (diphenylphosphoryl azide) method, DCC+additive (1-hydroxybenzotriazole, N-hydroxysuccinamide, N-hydroxy-5-norbornane-2,3-dicarboxylmide, and the like) method, and Woodward's method. The present protein obtained by chemical synthesis can be suitably purified in accordance with various kinds of conventional purification methods as described above.

Proteins shown by partial sequences of the proteins according to the present invention can also be obtained by cleaving the proteins according to the present invention, by a suitable peptidase.

A further aspect of the present invention relates to antibodies recognizing the proteins according to the present invention. The antibodies can be prepared using the present proteins as antigens. The antigens to be used may be the present proteins or fragments thereof. The fragments to be used consist of amino acids of at least eight, preferably at least ten, more preferably at least twelve, and even more preferably fifteen or more amino acids. In order to prepare specific antibodies to the present proteins, it is preferable to use a region comprising a characteristic amino acid sequence of the present proteins. The amino acid sequence of this region is not necessarily required to be homologous or identical to a sequence of the proteins or fragments thereof. An amino acid sequence of a site that is exposed outward on a tertiary structure thereof, may be preferable for such an amino acid sequence. Even if the amino acid sequence of the exposure site is not continuous on the primary structure, it is sufficient for the amino acid sequence to be continuous with respect to the exposure site. The antibodies are not particularly limited, and can be any antibody as long as it can specifically recognize the present proteins. The phrase "specifically recognize the present proteins" means to recognize the present proteins, for example, to bind to the present proteins, but not recognize or weakly recognize proteins other than the present proteins. The presence or absence of the recognition can be determined by known antigen-antibody binding reactions.

The antibodies can be produced by utilizing known antibody producing methods. For example, the antibodies can be obtained by administering to an animal an antigen alone, or an antigen bound to a carrier, with or without an adjuvant, and thereby inducing immunity, such as a humoral response, and/or a cellular response. Any known carrier can be used as long as it does not exhibit an adverse action against the host, and is capable of increasing the antigenicity of the antigen. Specifically, examples of the carrier include cellulose, polymeric amino acids, albumin, and keyhole limpet hemocyanin. Examples of the adjuvant include Freund's complete adjuvant (FCA), Freund's incomplete adjuvant (FIA), Ribi (MPL), Ribi (TDM), Ribi (MPL+TDM), *Bordetella pertussis* vaccine, muramyldipeptide (MDP), aluminium adjuvant (ALUM), and combinations of these. Mouse, rat, rabbit, goat, horse, or the like, can be preferably used as animals for immunization.

A polyclonal antibody can be acquired from the serum of an animal that was administered with an antigen by using any known method for recovering an antibody. Immunoaffinity chromatography may be employed as a preferable example of the method for recovering an antibody.

A monoclonal antibody can be produced by collecting an antibody-producing cell, (for example, lymphocytes derived from spleen or lymph nodes,) from an animal that was administered with an antigen, and then employing a means of transformation of the cell into an immortalized cell, (for example, a myeloma strain such as P3-X63-Ag8 line). For example, the antibody-producing cell is fused with an immortalized cell by any known method to prepare a hybridoma which is subsequently subjected to cloning. The various cloned hybridomas are used to screen for a hybridoma that produces an antibody specifically recognizing a protein of the present invention. The antibody can be then recovered from a culture solution of that hybridoma.

A polyclonal antibody or monoclonal antibody, which is capable of recognizing or binding to a protein of the present invention, can be utilized as an antibody for purification of the present protein, reagent, labeling marker or the like. In particular, an antibody that inhibits the function of the present protein can be used for regulating the function of the present protein, and is useful for elucidating, preventing, improving, and/or treating various kinds of diseases due to an abnormality of a present protein, in amount and/or function.

A still further aspect of the present invention relates to methods of identifying compounds that inhibit the function of the proteins, according to the present invention, or compounds that inhibit the expression of the polynucleotides, according to the present invention. The present identification methods can be carried out using at least one member selected from the proteins, the polynucleotides, the recombinant vectors, the transformants, and the antibodies which are provided in the present invention, by employing any known pharmaceutical screening system. The present identification methods include any methods that are carried out in vitro or in vivo. The present identification methods allow screening for antagonists, by drug design based on the structure of the present proteins, screening for an inhibitor of the expression at the gene level by utilizing a protein synthesis system, screening for a substance recognized by an antibody by utilizing the antibody, or the like.

The method of identifying a compound that inhibits the function of the proteins according to the present invention can be carried out using an experimental system capable of measuring the function of the present protein, which comprises making the present protein coexist with a compound to be tested (test compound), under conditions allowing the interaction of the present protein with the test compound, and measuring the function of the present protein, subsequently, comparing the function of the present protein in the presence of the test compound with the function of the present protein in the absence of the test compound, and finally detecting the presence, the absence, or the change of the function of the present protein, such as decrease, increase, elimination, and appearance. Where the function of the present protein is decreased or eliminated in the presence of a test compound, in comparison to the function of the present protein in the absence of the test compound, it can be determined that the test compound inhibits the function of the present protein. The function of the proteins can be measured by direct detection of the function, or by introducing, for example, a signal as an indicator of the function, into an experimental system, and detecting the signal. Examples of a signal include enzymes such as GST, tag peptides such as His-tag, Myc-tag, HA-tag, FLAG-tag, or Xpress-tag, or a fluorescent substance. Any other labeling substance can be used as long as it is used in a conventional method of identifying a compound.

The function of the proteins according to the present invention may be, for example, a function of accelerating the activation of a Rho family protein, and a function of binding to a Rho family protein.

The identification methods, utilizing a binding function of the proteins according to the present invention, to a Rho family protein as an indicator, can be carried out, for example, by expressing the present proteins using gene manipulation techniques to obtain the proteins, and detecting the binding of the proteins to a Rho family protein in the presence or absence of a test compound. Specifically, for example, the present proteins can be subjected to a reaction in the presence or absence of a test compound, with a Rho family protein that is expressed as a GST-fusion protein by using gene manipulation techniques followed by binding to glutathione-Sepharose. The identification of compounds that inhibit the binding function of the present proteins to a Rho family protein, can be achieved by measuring the present proteins that bind to the Rho family proteins bound to glutathione-Sepharose. Where the binding of both proteins is decreased or eliminated, in the presence of a test compound, in comparison to the binding of both proteins in the absence of the test compound, it can be determined that the test compound inhibits the binding function of the present proteins to the Rho family proteins. The quantitative measurement of the present proteins can be carried out, for example, by using antibodies according to the present invention. An antibody labeled with a labeling substance such as enzymes (e.g. HRP or ALP), a radioactive isotope, a fluorescent substance, or biotin may be used. Alternatively, a labeled second antibody may be used. In the case of using the present proteins fused with a tag-peptide, the quantitative measurement thereof can be carried out using an antibody against the tag-peptide. Alternatively, the present proteins may be used after labeling directly with a labeling substance, such as the aforementioned enzyme, radioactive isotope, fluorescent substance, biotin, or the like. In such a case, the quantitative measurement can be carried out by measuring the labeling substance.

More specifically, compounds that inhibit the binding of the proteins according to the present invention, to a Rho family protein, can be identified using suitable cells in which a polynucleotide encoding the present protein are co-expressed with a polynucleotide encoding a Rho family protein, and using an experimental system which detects the binding of both proteins, by pull-down assay (Example 3).

A well known two-hybrid method can also be used for an identification method of the present invention. For example, the method can be carried out wherein a plasmid for expressing a fusion protein of the protein according to the present invention and a DNA binding protein, a plasmid for expressing a fusion protein of a Rho family protein and a transcription activating protein, and a plasmid containing a reporter gene that is linked to a suitable promoter gene are introduced to a yeast, a eukaryotic cell, or the like. The identification of a compound that inhibits the binding of the present protein to a Rho family protein can be achieved by comparing the amount of expression of the reporter gene, in the presence of a test compound, with an amount of expression of the reporter gene in the absence of the test compound. In the case that the amount of expression of the reporter gene in the presence of the test compound is decreased or eliminated, compared to the amount of expression of the reporter gene in the absence of the test compound, it can be determined that the test compound inhibits the binding function of the present protein to a Rho family protein. Any reporter genes that are used in a conventional reporter assay can be used herein. A reporter gene can be exemplified by a gene encoding a protein having an enzyme activity, such as, luciferase, $\beta$-Gal, chloramphenicol acetyl transferase, or the like. The expression of the reporter gene can be detected by determining the activity of the gene product, for example, an enzyme activity in the case of using the reporter gene exemplified in the above.

A surface plasmon resonance sensor, such as, the BIACORE system, or the like, can also be used in the method of identifying a compound that inhibits the binding of a protein of the present invention to a Rho family protein. Alternatively, Scintillation proximity assay (SPA), or a method employing fluorescence resonance energy transfer (FRET), can also be used for carrying out the present identification method.

A identification methods utilizing an acceleration function of the proteins according to the present invention, on the activation of a Rho family protein as an indicator, can be carried out, for example, by allowing a present protein to co-exist with a Rho family protein, the activation of which can be accelerated by the present protein, and measuring the amount of activation of a Rho family protein in the presence or absence of a test compound. In the case that the amount of an activated Rho family protein in the presence of a test compound is decreased, compared to the amount of an activated Rho family protein in the absence of the test compound, it can be determined that the test compound inhibits an acceleration function of the present protein on the activation of a Rho family protein. An activated Rho family protein can be quantitatively measured by using an antibody raised against the protein. For example, an activated Rho family protein can be quantitatively measured using an effector molecule capable of binding to the activated Rho family protein, but not binding or weakly binding to the non-activated Rho family protein. Specifically, as shown in Example 4, it is conducted to detect the binding of an activated Rho family protein, to a GST-fusion protein containing a binding site of an effector molecule to a Rho family protein, by a pull-down assay. Then, an amount of the activated Rho family protein is measured by electrophoresis and Western blotting. An effector molecule that binds to an activated Rho family protein is different depending on the type of Rho family protein. Therefore, a suitable effector protein may be selected for use according to the kind of a Rho family protein used. For example, activated Cdc42 and activated Rac1 are known to bind to the effector molecule PAK-1. While activated RhoA binds to the effector molecule, Rhotekin.

An identification method utilizing an acceleration function of the proteins according to the present invention, on the activation of a Rho family protein as an indicator, can be also carried out by allowing the present proteins to co-exist with a Rho family protein being bound to radioactive isotope-labeled GDP. The activation of which can be accelerated by the present proteins and with GTP, and the amount of an activated Rho family protein, in the presence or absence of a test compound, can be subsequently measured. The activated Rho family protein can be quantitatively determined by measuring the decreased amount of the Rho family protein being bound to a radioactive isotope-labeled GDP.

The phrase "inhibiting the function of accelerating the activation of a Rho family protein" means to inhibit the acceleration of the activation of a Rho family protein, where the acceleration is caused by a protein according to the present invention.

A Rho family protein used in an identification method according to the present invention may be a protein lacking a part thereof, or a protein labeled with a labeling substance described above, as long as the binding thereof, with a protein according to the present invention, and the acceleration of the activation thereof, by the present protein, is not affected.

A method of identifying a compound that inhibits the expression of a polynucleotide according to the present invention can be carried out using an experimental system capable of measuring the expression of the present polynucleotide, which comprises making the present polynucleotide coexist with a test compound, under conditions allowing the interaction of the present polynucleotide with the test compound, and measuring the expression of the present polynucleotide. The method can comprise subsequently comparing the expression of the present polynucleotide in the presence of the test compound, with the expression of the present polynucleotide in the absence of the test compound, and finally detecting the presence, the absence, or the change of the expression of the present polynucleotide, such as decrease, increase, elimination or the appearance thereof. In the case that the expression of the present polynucleotide is decreased or eliminated in the presence of a test compound, in comparison to the expression of the present polynucleotide in the absence of the test compound, it can be determined that the test compound inhibits the expression of the present polynucleotide. Specifically, for example, the present identification method can be carried out using an experimental system using a transformant according to the present invention, for expressing a present polynucleotide, which comprises contacting the transformant with a test compound, and then measuring the expression of the present polynucleotide. The expression of the present polynucleotide can be measured easily by detecting the amount of an expressed protein, or by detecting the function of the protein, for example, the function of accelerating the activation of a Rho family protein. Further, the expression of a present polynucleotide can be measured also by introducing, for example, a signal as an indicator of the expression into the experimental system, and detecting the signal. Examples of a signal include: enzymes such as GST; tag peptides such as His-tag, Myc-tag, HA-tag, FLAG-tag, or Xpress-tag; or a fluorescent substance. A method of detecting these signals is well known to those skilled in the art.

A method of identifying a compound that inhibits the expression of a polynucleotide according to the present invention can also be carried out by, for example, preparing a vector, that comprises a promoter region of a gene corresponding to the present polynucleotide and a reporter gene linked downstream of the promoter region instead of the present polynucleotide, and contacting a cell, e.g. a eukaryotic cell, which contains the vector, with the test compound, and then determining the presence or absence of, or a change in expression of the reporter gene. Any reporter genes that are used in a conventional reporter assay can be used herein. A reporter gene can be exemplified by a gene encoding a protein having an enzyme activity, such as, luciferase, β-Gal, chloramphenicol acetyl transferase, or the like. The expression of the reporter gene can be detected by determining the activity of the gene product, for example, an enzyme activity in the case of using a reporter gene exemplified above.

A compound obtained by an identification method according to the present invention can be utilized as a candidate compound for an inhibitor or an antagonist of the function of a present protein, for example, the function of accelerating the activation of a Rho family protein. Further, the compound can be utilized as a candidate compound for an inhibitor of the expression of a polynucleotide according to the present invention. These candidate compounds can be prepared as a medicament by taking into consideration the balance between usefulness and toxicity. Therefore, it can be expected that these compounds may have an effect of preventing and/or treating various kinds of symptoms due to an abnormality in the function of the present protein, and/or an abnormality in the expression of a present polynucleotide. The compounds according to the present invention include compounds that are obtained by other methods than the present identification methods if they are capable of inhibiting the function of a present protein, and/or the expression of a present polynucleotide.

A further aspect of the present invention relates to a medicament or a pharmaceutical composition which is based on inhibiting or antagonizing the function of a present protein, and/or the expression of a present polynucleotide. A medicament or a pharmaceutical composition according to the present invention can contain a protein, a polynucleotide, a recombinant vector, a transformant, an antibody, or a compound, which is provided according to the present invention, as an effective ingredient.

A medicament according to the present invention can be a medicament that contains an effective amount of at least one member selected from a protein, a polynucleotide, a recombinant vector, a transformant, an antibody, or the compound, which is provided according to the present invention, as an effective ingredient. In general, it is preferable to prepare a pharmaceutical composition using one or more kinds of pharmaceutically acceptable carriers (pharmaceutical carriers).

An amount of the effective ingredient contained in the pharmaceutical composition according to the present invention can be suitably selected from a wide range. In general, a suitable amount may fall within a range of approximately 0.00001 to 70 wt %, preferably approximately 0.0001 to 5 wt %.

A pharmaceutical carrier may be a diluent or excipient, which can be generally used in accordance with the form of use of the pharmaceutical composition, such as, a filler, an extender, a binder, a wetting agent, a disintegrator, and/or a lubricant. These can be suitably selected and used in accordance with the form of use of the pharmaceutical composition used.

The pharmaceutical carrier may be, for example, water, a pharmaceutically acceptable organic solvent, collagen, polyvinyl alcohol, polyvinylpyrrolidone, carboxyvinyl polymer, sodium alginate, soluble dextran, sodium carboxymethyl starch, pectin, xanthan gum, acacia gum, casein, gelatin, agar, glycerin, propylene glycol, polyethylene glycol, vaseline, paraffin, stearyl alcohol, stearic acid, human serum albumin, mannitol, sorbitol and lactose. One or a combination of two or more kinds of these carriers may be suitably selected, and used in accordance with the form of use of a pharmaceutical composition of the present invention.

As desired, various ingredients used in conventional protein preparations can be suitably used herein, such as a stabilizer, a bacteriocide, a buffer agent, an isotonizing agent, a chelating agent, a pH adjuster, or a surfactant, for preparing the pharmaceutical composition.

As a stabilizer, the following may be used: human serum albumin, common L-amino acids, sugars, and cellulose derivatives. These can be used independently or in combination with a surfactant, and the like. Use of these in such a combination may give increased stability to an effective ingredient. An L-amino acid is not particularly limited, and may be any one of glycine, cysteine, glutamic acid, and the like. A sugar is not particularly limited, and may be any one of the monosaccharides (such as glucose, mannose, galactose, and fructose), sugar alcohols (such as mannitol, inositol, and xylitol), disaccharides (such as sucrose, maltose, and lactose), polysaccharides (dextran, hydroxypropylstarch, chondroitin sulfate, and hyaluronic acid), derivatives thereof, and so on. A cellulose derivative is not particularly limited, and may be any one of methylcellulose, ethylcellulose, hydroxyethylcellulose, hydroxypropylcellulose, hydroxypropylmethylcellulose, sodium carboxymethylcellulose, and the like.

A surfactant is not particularly limited, and can be both an ionic surfactant and/or a non-ionic surfactant. As a surfactant, the following may be used: polyoxyethyleneglycol sorbitan alkyl ester base; polyoxyethylene alkyl ether base; sorbitan monoacyl ester base; or a fatty acid glyceride base.

As a buffer agent, the following may be used: boric acid; phosphoric acid; acetic acid; citric acid; ε-aminocaproic acid; glutamic acid; and/or a salt thereof, for example, an alkali metal salt and/or an alkaline earth metal salt, such as a sodium salt, a potassium salt, a calcium salt and a magnesium salt.

As an isotonizing agent, the following may be used: sodium chloride; potassium chloride; sugars; or glycerin.

As a chelating agent, sodium edentate and citric acid may be used.

The medicaments and the pharmaceutical compositions according to the present invention can be used as solution preparations. Alternatively, they can be freeze-dried, so as to be preservable. They can be used by dissolving them in water, a buffered solution containing saline, and the like, and then adjusting them to a suitable concentration, at the time of use.

The medicaments and the pharmaceutical compositions according to the present invention can be used as agents for preventing and/or treating a disease due to an abnormality in the function of a present protein and/or an abnormality in the expression of a present polynucleotide. In addition, the medicaments and the pharmaceutical compositions can be used in methods for preventing and/or treating the aforementioned disease.

For abnormal symptoms due to an excess of a function of a protein according to the present invention, and/or the expression of a polynucleotide according to the present invention, an effective amount of an inhibitor that inhibits the function of a present protein and/or the expression of a present polynucleotide, may be administered to a subject together with a pharmaceutically acceptable carrier. The administration may result in obtaining an effect such as prevention, improvement, or treatment of the abnormal symptoms. Alternatively, the similar effect can be obtained by inhibiting the spontaneous expression of a present polynucleotide using an expression block method. The inhibition of the expression of a present polynucleotide can be achieved, for example, by using an anti-sense oligonucleotide, such as an oligonucleotide consisting of a partial sequence of a present polynucleotide. An oligonucleotide corresponding to a non-coding region of a present polynucleotide as well as an oligonucleotide corresponding to a coding region thereof, is useful as an anti-sense oligonucleotide used herein. In order to specifically inhibit the expression of a present polynucleotide, it is preferable to use a nucleotide sequence of a characteristic region of the polynucleotide.

The tissue distribution of the polynucleotide shown by the nucleotide sequence set forth in SEQ ID NO: 1, in the sequence listing, which is a specific example of a polynucleotide according to the present invention, was found to be approximately 5 times or more higher, specifically 4.5 times or more higher, in a stomach adenocarcinoid tumor, which is one of stomach tumors, as compared to that in a normal stomach tissue. The protein encoded by the polynucleotide shown by the nucleotide sequence set forth in SEQ ID NO: 1, has a DH/PH domain that is an active domain of Rho-GEF. Meanwhile, the polynucleotide (SEQ ID NO: 5), also has a DH/PH domain coding region, which consists of the polynucleotide (SEQ ID NO: 3), shown by the nucleotide sequence from the $581^{st}$ to the $1675^{th}$ nucleotides of the nucleotide sequence set forth in SEQ ID NO: 1, and includes an oligonucleotide (SEQ ID NO: 19) ligated to its 5'-terminal. The oligonucleotide (SEQ ID NO: 19) consists of a kozak sequence and a methionine codon. When the polynucleotide (SEQ ID NO: 5) was co-expressed with a gene encoding a Rho family protein, in a mammalian cell, the product of the polynucleotide was bound to the Rho family protein, and the activation of the Rho family protein was accelerated. It can be considered from these findings that the protein encoded by the polynucleotide shown by the nucleotide sequence set forth in SEQ ID NO: 5, works as a Rho-GEF. The oligonucleotide (SEQ ID NO: 19) consisting of a kozak sequence and a methionine codon, which was added to the 5'-terminal of the polynucleotide shown by the nucleotide sequence set forth in SEQ ID NO: 3, does not significantly affect the function of the expressed protein. Therefore, the present inventors believe that the protein encoded by the polynucleotide shown by the nucleotide sequence set forth in SEQ ID NO: 3 also works as a Rho-GEF. Further, the nucleotide sequence set forth in SEQ ID NO: 1 contains the nucleotide sequence set forth in SEQ ID NO: 3. Therefore, the present inventors believe that the protein encoded by the polynucleotide shown by the nucleotide sequence set forth in SEQ ID NO: 1 also works as a Rho-GEF. Among the Rho-GEF genes isolated so far, vav (Non-Patent References 3 and 4), ost (Non-Patent Reference 5), ibc (Non-Patent Reference 6), and the like are known to relate to cancer. Thus, the present inventors believe that the high expression of the present polynucleotides relate to a stomach tumor. Therefore, the medicaments and the pharmaceutical compositions according to the present invention may be useful as agents for preventing and/or treating a stomach tumor. In addition, the medicaments and the pharmaceutical compositions may be used in methods of preventing and/or treating a stomach tumor.

Suitable dosage ranges of the medicament and the pharmaceutical composition according to the present invention are not particularly limited, and can be determined in accordance with the following: effectiveness of the ingredients contained therein; the administration form; the route of administration; the type of disease; the characteristics of the subject (e.g., body weight, age, symptomatic conditions, and whether a subject is taking other pharmaceutical agents); and the judgment of a physician in charge. In general, a suitable dosage may fall, for example, within a range of about 0.01 μg to 100 mg, per 1 kg of the body weight of the subject, and preferably within a range of about 0.1 μg to 1 mg, per 1 kg of body weight. However, the dosage may be altered using conventional experiments for optimization of a dosage that are well known in the art. The aforementioned dosage can be divided for administration once to several times a day. Alternatively, periodic administration once every few days or few weeks can be employed.

When administering the medicament or the pharmaceutical composition according to the present invention, the medicament or the pharmaceutical composition may be used alone, or may be used together with other compounds or medicaments useful for preventing and/or treating the target disease.

In terms of a route of administration, it may be either systemic administration or local administration. The route of administration that is appropriate for a particular disease, symptomatic condition, or other factors, should be selected. For example, parenteral administration including normal intravenous injection, intra-arterial administration, subcutaneous administration, intracutaneous administration, and intramuscular administration can be employed. Oral administration can be also employed. Further, transmucosal administration or dermal administration can be employed. In the case of use for cancer disease, it may be preferable to employ a direct administration into the tumor by injection, and the like.

In terms of an administration form, various forms can be selected in accordance with a treatment purpose. For example, a solid formulation may be employed such as a tablet, pill, powder, powdered drug, fine granule, granule, or a capsule. Alternatively, a liquid formulation can be employed such as an aqueous formulation, ethanol formulation, suspension, fat emulsion, liposome formulation, clathrate such as cyclodextrin, syrup, or an elixir. These can be further classified, according to the administration route, into an oral formulation, parenteral formulation (drip injection formulation or injection formulation), nasal formulation, inhalant formulation, transvaginal formulation, suppositorial formulation, sublingual agents, eye drop formulation, ear drop formulation, ointment formulation, cream formulation, transdermal absorption formulation, transmucosal absorption formulation, and the like, which can be respectively blended, formed and prepared according to conventional methods.

The proteins, polynucleotides, recombinant vectors, transformants, antibodies, or the compounds, which are provided in the present invention, can be used by themselves as a means for diagnosing a disease, such as a diagnostic marker or a diagnostic reagent.

According to the present invention, for example, use of all or a part of a polynucleotide according to the present invention allows the specific detection of the presence or absence of an abnormality in a polynucleotide or a gene containing the polynucleotide, or the presence or absence of expression thereof, in an individual, or in various kinds of tissues. The detection of a polynucleotide according to the present invention allows for a diagnosis of susceptibility to, onset of, and/or prognosis of, a disease due to an abnormality in the amount of a polynucleotide or a gene containing the polynucleotide, and/or, an abnormality in the function thereof.

Diagnosis of a disease can be carried out, for example, by detecting the presence of a polynucleotide according to the present invention, by determining the existing amount thereof, and/or by identifying a mutation, with respect to a sample to be tested (test sample). In comparison to a normal control sample, a change in the existence of a present polynucleotide, and a quantitative change thereof, can be detected. Alternatively, an amplified product obtained by amplifying a present polynucleotide using a known method may be subjected, for example, to the measurement of a change in size. In comparison to a normal genotype, a mutation such as deletion or insertion can be detected. Further, a polynucleotide amplified from a test sample may be subjected, for example, to hybridization to a labeled polynucleotide according to the present invention, which allows the isolation of a point mutation. The detection of such a change or a mutation allows the aforementioned diagnosis.

The present invention can provide a qualitative or quantitative measurement method, for a polynucleotide according to the present invention, in a test sample. Further, a qualitative or quantitative measurement method for the mutation, in the specific region of a polynucleotide, can also be provided.

The tissue distribution of the polynucleotide shown by the nucleotide sequence set forth in SEQ ID NO: 1, was found to be approximately 5 times or more higher, specifically 4.5 times or more higher, in a stomach adenocarcinoid tumor, which is one of stomach tumors, compared to that in a normal stomach tissue. Meanwhile, as described in the above, it can be considered that the high expression of a present polynucleotide relates to a stomach tumor. Therefore, the detection of the increased amount of expression of the polynucleotide in a test sample allows execution of a method of determining whether the test sample is a test sample that is derived from a stomach tumor or not. Such a determination method may also be included in the scope of the present invention. In this determination method, the increased amount of expression of the polynucleotide can be detected by comparing a test sample with a normal control sample. A human stomach-derived tissue may be preferably used as a test sample. A normal human stomach-derived tissue may be preferably used as a control sample. In the case that the amount of expression of the polynucleotide is increased compared to that in a control sample, preferably approximately 5 times or more, more preferably approximately 4.5 times or more, it can be determined that the test sample is a human stomach tumor-derived sample. The polynucleotides according to the present invention other than the polynucleotide shown by the nucleotide sequence set forth in SEQ ID NO: 1 can also be used for carrying out this determination method. The polynucleotide shown by the nucleotide sequence set forth in SEQ ID NO: 3 can be used for such a polynucleotide. The phrase "amount of expression of the polynucleotide according to the present invention" means the amount of the transcription product of the polynucleotide.

A test sample is not particularly limited as long as it contains a nucleic acid of a polynucleotide according to the present invention, a gene containing the polynucleotide, or a mutant gene thereof. For example, a sample derived from a living organism such as a cell, blood, urine, saliva, spinal fluid, biopsy tissue, or autopsy material, and the like, may be used as a test sample. Alternatively, as desired, a nucleic acid may be extracted from a sample to prepare a nucleic acid sample for use. A nucleic acid may be a genomic DNA which is directly used to the detection. Alternatively, a nucleic acid may be enzymatically amplified by employing PCR, or other amplification methods, prior to analysis. RNA or cDNA may be similarly used. A nucleic acid sample may also be prepared according to various methods, for facilitating detection of a target sequence, for example, denaturation, digestion with restriction enzymes, electrophoresis, or dot blotting.

Any known gene detection methods can be used for detecting a polynucleotide according to the present invention, or a gene containing the polynucleotide. Specifically, for example, plaque hybridization, colony hybridization, Southern blotting, Northern blotting, the NASBA method (nucleic acid sequence-based amplification method), reverse transcription-polymerase chain reaction (RT-PCR), or the like can be used. In addition, in situ RT-PCR, in situ hybridization, or the like, which allows cell level measurement, can be used for the detection. In such a gene detection method, it is useful to use an oligonucleotide, which consists of a partial sequence of a polynucleotide according to the present invention, and has the property as a probe or a primer, for carrying out the isolation and/or the amplification of the polynucleotide, a gene containing the polynucleotide, or a mutant gene thereof. The phrase "oligonucleotide having the property as a probe" means an oligonucleotide that is capable of specifically hybridizing only to a present polynucleotide, and consists of a characteristic sequence of a present polynucleotide. The phrase "oligonucleotide having the property as a primer" means an oligonucleotide that is capable of specifically amplifying only a present polynucleotide, and consists of a characteristic sequence of a present polynucleotide. Further, when detecting a mutant gene capable of being amplified, a primer or a probe having a sequence with a predetermined length, which contains a mutation site within the gene, is prepared and used. A probe and a primer may have a nucleotide sequence consisting of, preferably, from about 5 to 50 nucleotides, more preferably, from about 10 to 35 nucleotides, and even more preferably, from about 15 to 30 nucleotides. Specifically, an oligonucleotide shown by the nucleotide sequence set forth in SEQ ID NO: 7, SEQ ID NO: 8, SEQ ID NO: 9, or SEQ ID NO: 10 can be preferably used as a primer for amplifying a polynucleotide of the present invention, or a fragment thereof, or as a probe for detecting a present polynucleotide. A labeled probe is normally used as the probe, but the unlabeled probe can also be used. Alternatively, the detection can also be carried out by measuring the specific binding to a ligand that was labeled directly or indirectly. Various methods are known for labeling a probe and a ligand. For example, nick translation, random priming, or a method utilizing kinase treatment, may be used. Labeling substances suitable for use include a radioactive isotope, biotin, a fluorescent substance, a chemiluminescent substance, an enzyme, an antibody, and the like.

PCR is preferable as a gene detection method, from the viewpoint of sensitivity. Any well-known method of PCR can be employed, as long as it is a method that uses a primer capable of specifically amplifying a polynucleotide according to the present invention, a gene containing the polynucleotide, or a mutant gene thereof. For example, RT-PCR may be employed. In addition, various modified PCT methods used in the art can be applied.

In addition to detection of a gene, PCR allows quantitative measurement of a polynucleotide according to the present invention, a gene containing the polynucleotide, or a mutant gene thereof. Such an assay method may be exemplified by a competitive assay, such as, an MSSA method (multi-channel simplex simulated annealing method), or PCR-SSCP (PCR-single strand conformation polymorphism), which is known as a mutation detection method that utilizes a change in mobility accompanying a structural change of a single-stranded DNA.

According to the present invention, for example, use of a protein according to the present invention allows the specific detection of, the presence or absence of, an abnormality in the protein itself, and in its function, in an individual or in various kinds of tissues. The detection of an abnormality in a protein according to the present invention, and in its function, allows a diagnosis of susceptibility to, onset of, and/or prognosis of, a disease due to an abnormality in the amount of the protein and/or an abnormality in its function.

The diagnosis of a disease by detecting a protein can be carried out, for example, by detecting the presence of a protein, by determining the existing amount thereof, and/or by identifying a mutation, with respect to a sample to be tested (test sample). That is to say, a protein according to the present invention, and/or its mutant, may be quantitatively or qualitatively measured. In comparison to a normal control sample, a change in the existence of a present protein, and a quantitative change thereof, can be detected. Alternatively, in comparison to a normal control sample, a mutation can be detected, for example, by determining an amino acid sequence. The detection of such a change or a mutation allows the aforementioned diagnosis. A biological sample derived from a living organism, such as blood, serum, urine, biopsy tissue, and the like, may be used as a test sample.

A protein according to the present invention, and the protein with a mutation, can be measured using a protein according to the present invention, a fragment thereof, or an antibody against the protein or the fragment. Specifically, for example, the protein shown by the amino acid sequence set forth in SEQ ID NO: 2, SEQ ID NO: 4, or SEQ ID NO: 6, a protein shown by the amino acid sequence having a deletion, substitution, insertion, or addition of one or several or more amino acids, in the amino acid sequence of the protein, the fragment thereof, or an antibody against the protein or the fragment, can be used.

Any protein detection methods, or protein quantitation methods which are well known in the art, can be used for quantitative or qualitative measurement of the protein. For example, the amino acid sequence analysis of a present protein allows a detection of a mutant protein. More preferably, an antibody (a polyclonal antibody or a monoclonal antibody) may be used for detecting the difference in the protein sequence, or the presence or absence of the protein.

The present invention can provide a qualitative or quantitative measurement method for a present protein in a test sample, or a qualitative or quantitative measurement method for a mutation in the specific region of the protein.

Specifically, the aforementioned detection may be carried out by subjecting a test sample to immunoprecipitation, using a specific antibody raised against a present protein, and then analyzing the present protein by Western blotting or immunoblotting. Further, the detection of a present protein in a paraffin tissue section, or a frozen tissue section, may be carried out by means of immuno-histochemical techniques using a specific antibody raised against the present protein.

The preferable methods of detecting a present protein or its mutant, may be, for example, enzyme-linked immunosorvent assay (ELISA), radio immuno assay (RIA), immunoradiometric assay (IRMA), and immunoenzymometric assay (IEMA), including a sandwich method using a monoclonal antibody and/or a polyclonal antibody. Alternatively, competitive binding assay, and the like may be employed.

A protein, polynucleotide, recombinant vector, transformant, and/or antibody, which are provided according to the present invention, can each be used by themselves or in combination as a reagent, or the like. The reagent may be contained in a substance such as a buffer solution, a salt, a stabilizer, and/or an antiseptic agent, in addition to at least one member selected from a protein, a polynucleotide, a recombinant vector, a transformant, and an antibody which are provided according to the present invention. A known formulation means may be introduced, in accordance with the respective properties, at the time of formulation. The reagent can be used, for example, in a determination method, a method of identifying a compound, or a method of measuring the present protein, or a present polynucleotide, which is provided according to the present invention. In addition, the reagent is useful, for example, in elucidating an intracellular signal transduction pathway wherein a protein or a polynucleotide according to the present invention may be involved and the reagent can be used in fundamental research, such as research for a disease due to an abnormality of the protein or the polynucleotide.

The present invention further provides a reagent kit containing at least one member selected from a protein, a polynucleotide, a recombinant vector, a transformant, and an antibody which are provided according to the present invention. The kit may further contain a substance necessary for carrying out a measurement, such as a labeling substance, for detecting a protein or a polynucleotide according to the present invention, an agent for detecting the labeling substance, a reaction diluent, a standard antibody, a buffer solution, a washing agent, and a reaction terminating solution. As a labeling substance, the proteins described above, radioactive isotype, or the like, can be used. A labeling substance may be previously linked to the protein or the polynucleotide according to the present invention. The present reagent kit can be used, for example, in the determination method, the method of identifying a compound, or the method of measuring a present protein, or a present polynucleotide, which is provided according to the present invention. In addition, the present reagent kit can also be used as a test agent or a test kit in the test method using the aforementioned measurement method. The present reagent kit can further be used as a diagnostic agent, or a diagnostic kit in the diagnostic method using the aforementioned measurement method.

Hereinafter, the present invention may be explained more specifically with the following examples.

Example 1

Construction of Human Brain-Derived cDNA Library and Isolation of Gene

A cDNA library was constructed according to a conventional method employing a polyA+ RNA derived from human brain, fetal brain, and brain hippocampus (Clontech Inc.: catalog Nos. 6516-1, 6525-1, and 6578-1), as starting material. The nucleotide sequences of cDNA clones were determined after isolating cDNA fragments by dbEST analysis. Specifically, a cDNA library was constructed in accordance with the method of Ohara et al. (Non-Patent Reference 19). Approximately 50,000 recombinants were randomly selected from the cDNA library. Then, with respect to approximately 30,000 cDNA clones among them, their 5'-terminal and 3'-terminal nucleotide sequences were determined. Further, approximately 1,100 cDNA clones were selected by mainly in-vitro transcription translation experiments, and their nucleotide sequences were determined according to the method of Ohara et al.

The ORF was predicted for cDNA clones, whose entire nucleotide sequences were determined, by a conventional analysis method using a computer program. Subsequently, the ORF region was analyzed by a domain motif search, to identify a cDNA containing a region encoding a DH/PH domain that is an active domain of Rho-GEF.

The identified cDNA clone hj03796 is a DNA (SEQ ID NO: 1) having a novel nucleotide sequence of 4977 bp long, containing an ORF that encodes 1340 amino acid residues (SEQ ID NO: 2). The DH domain consists of 175 amino acid residues from the $97^{th}$ valine (Val) to the $271^{st}$ aspartic acid (Asp) of the amino acid sequence set forth in SEQ ID NO: 2. The PH domain consists of 98 amino acid residues from the $297^{th}$ leucine (Leu) to the $394^{th}$ leucine (Leu) of the amino acid sequence set forth in SEQ ID NO: 2. The DH domain coding region and the PH domain coding region in the nucleotide sequence set forth in SEQ ID NO: 1 correspond to the nucleotides from the $602^{nd}$ to the $1126^{th}$ nucleotide, and the nucleotides from the $1202^{nd}$ to the $1495^{th}$ nucleotide, respectively.

Example 2

DNA Expression and Purification

The clone hj03796 that was identified in Example 1, was used for expressing the protein encoded by the clone in a 293EBNA cell (Invitrogen) as a FLAG-tagged protein. A protein that consists of a partial sequence of the protein encoded by the clone and contains a DH/PH domain was expressed in a 293EBNA cell. The expression was confirmed by Western blotting.

At first, an expression vector containing hj03796 gene was constructed. The gene was amplified by pfu turbo (Stratagene) using pBluescript II-hj03796 (hj03796 was inserted into the SalI-NoI site of pBluescript II SK+: Kazusa DNA Research Institute) as a template and K0599s3 (SEQ ID NO: 7) and asBam1 (SEQ ID NO: 8) as primers. The amplified gene was cleaved with HincII/BamHI to obtain a gene fragment. pBluescript II-hj03796 was cleaved with SalI/HincII to obtain a gene fragment pDsRed2-N1 (Clontech) was cleaved with SalI/HincII to obtain a gene fragment. These fragments were subjected to ligation, and then introduced into a competent cell. Subsequently, DNA was purified from the transformed *Escherichia coli* using a purification kit. The purified DNA was cleaved with SalI/BamHI to obtain an hj03796 fragment. The hj03796 fragment was inserted into a SalI/BamHI site of a vector DNA, pFLAG-CMV5b (SIGMA), to obtain an hj03796 expression vector. Correct insertion of the sequence treated with restriction enzyme was verified by sequencing. The sequencing reaction was carried out using a DNA Sequencing Kit (ABI). Electrophoresis and analysis were performed using an ABI PRISM 377.

Next, a vector was constructed by Gateway™ cloning technology (Invitrogen) for expressing a protein that consists of a partial sequence of the full-length protein encoded by hj03796 clone and contains a DH/PH domain (hereinafter, the protein may be referred to hj03796DH/PH). A polynucleotide, which consists of a homologous region to a DH/PH domain coding region of proto-Dbl (the region corresponding to the nucleotides from the $581^{st}$ to the $1675^{th}$ nucleotide of SEQ ID NO: 1), and an oligonucleotide (SEQ ID NO: 19) ligated to its 5'-terminal, was amplified by pfu turbo (Stratagene) using pBluescript II-hj03796 as a template. The oligonucleotide (SEQ ID NO: 19) consists of a kozak sequence and a methionine codon. After that, the amplified product was inserted into pENTR/SD/D-TOPO in a reaction using TOPO cloning system to prepare an entry vector. The primers, 03796D/P-F1 (SEQ ID NO: 9) and 03796D/P-R3 (SEQ ID NO: 10), were used for the amplification reaction. The entry vector was then subjected to a recombination reaction in the presence of LR clonase, using a C-terminal 3×FLAG-tagged protein-expression vector to prepare an expression vector to express hj03796DH/PH as a 3×FLAG-tagged protein. Correct insertion of the nucleotide sequence of the DH/PH domain coding region of hj03796 was verified by sequencing. The sequencing reaction was carried out using DYEnamic ET Terminator Cycle Sequencing Kit (Amersham Biosciences). Electrophoresis and analysis were performed using an ABI PRISM 377.

An expression vector of a DH/PH domain of proto Dbl, a known Rho-GEF, was constructed for the purpose of using a DH/PH domain of proto Dbl as a control for hj03796DH/PH. Hereinafter, a DH/PH domain of proto Dbl may be referred to as proto-Dbl DH/PH. The DH/PH domain coding region of proto-Dbl (from the $1485^{th}$ to the $2429^{th}$ nucleotide of the proto-Dbl nucleotide sequence, where the positions are indicated by a number from the beginning of the start codon, ATG) was amplified by pfu turbo using brain first strand DNA of Multiple Tissue cDNA Panels (Clontech) as a template. After that, the amplified product was inserted into a BgIII-SalI site of pFLAG-CMV5a (SIGMA) in a ligation reaction to prepare an expression vector for expressing proto-Dbl DH/PH as a FLAG-tagged protein. The primers, D/P-s1 (BgIII) (SEQ ID NO: 11) and D/P-as1 (SalI) (SEQ ID NO: 12), were used for the amplification reaction. Sequencing was carried out to verify correct insertion of the nucleotide sequence of the DH/PH domain coding region of proto-Dbl. As a result, it was found that one nucleotide was different from the disclosed sequence. However, this one nucleotide difference did not cause a substitution of the amino acid. Specifically, in comparison to the disclosed sequence of proto-Dbl (accession number: X12556), the nucleotide sequence of the DH/PH domain coding region of proto-Dbl, which was inserted to the expression vector, was found to have an adenine (A) instead of thymine (T) at the position 1962 from the beginning of the start codon, ATG of the disclosed sequence. The nucleotide sequence of the DH/PH domain coding region of proto-Dbl, which was inserted into the expression vector, consists of the nucleotide sequence of the disclosed sequence of proto-Dbl from the $1480^{th}$ to the $2433^{rd}$ nucleotides, from the beginning of the start codon, ATG; and the sequence ATGGCA ligated its 5'-terminal. Therefore, the nucleotide of the position 489 in the DH/PH domain coding region of proto-Dbl, which was inserted to the expression vector from the beginning of the start codon, ATG, was different from the corresponding nucleotide of the disclosed sequence. The nucleotides of the disclosed sequence from the $1960^{th}$ to the $1962^{nd}$ nucleotides, from the beginning of the start codon, ATG, are GGT, which codes glycine. The nucleotides of the nucleotide sequence of the DH/PH domain coding region of proto-Dbl, which was inserted to the expression vector from the $487^{th}$ to the $489^{nd}$ nucleotides from the beginning of the start codon, ATG, are GGA, which codes glycine, as well. Thus, an amino acid substitution due to the one nucleotide difference was not observed. The disclosed nucleotide sequence of proto-Dbl, and the amino acid sequence encoded by the disclosed nucleotide sequence, are shown in SEQ ID NO: 26 and SEQ ID NO: 27, respectively. The nucleotide sequence of proto-Dbl, as shown in SEQ ID NO: 26, is the nucleotide sequence disclosed in an open data base provided by NCBI (National Center for Biotechnology Information) at the time of browsing on Feb. 24, 2005.

Each expression vector was transfected into 293EBNA cells by lipofection. Specifically, each vector in serum-free DMEM was mixed with LipofectAMINE 2000 (Invitrogen) in DMEM, and then incubated at room temperature for 20 minutes. The obtained mixture was added to 293EBNA cells. The cells had been seeded the day before transfection, and cultured at 37° C. in the presence of 5% $CO_2$. The cells subjected to transfection were incubated at 37° C., for 2 days, in the presence of 5% $CO_2$. After culturing, the cells were washed with phosphate-buffered physiological saline containing ethylene diamine tetra acetic acid (PBS-EDTA), and then lysed with lysis buffer containing 1% protease inhibitor cocktail (1/100 concentration: SIGMA) to prepare a cell lysate. The lysis buffer was composed of 25 mM Tris-HCl (pH 7.5), 150 mM NaCl, 1 mM $CaCl_2$, and 1% Triton X-100.

Each cell lysate was mixed with an equal volume of SDS-PAGE sample buffer, and subjected to heat treatment at 100° C. for 5 minutes, to prepare a sample for electrophoresis. SDS-polyacrylamide gel electrophoresis was carried out, and then the gel was equilibrated for 5 minutes or more, in blotting buffer. The proteins were transferred onto a PVDF membrane. After blotting, the PVDF membrane was subjected to blocking at 4° C. overnight, in a solution (TBS-T+BA) prepared by mixing TBS-T with Block Ace (Dainippon Pharmaceutical) at a ratio of 3:1. After blocking, the PVDF membrane was washed with TBS-T, with shaking, for 10 minutes or more. The SDS-PAGE sample buffer was composed of 1.7% Tris, 0.13 M HCl, 22% glycerol, 4.6% SDS, and 0.22 g/mL bromophenol blue. The blotting buffer was composed of 25 mM Tris, 40 mM ε-amino-n-caproic acid, 20% methanol, and 0.05% SDS. The TBS-T was composed of 150 mM NaCl, 10 mM Tris-HCl (pH 7.5), and 0.05% Tween-20.

The PVDF membrane was added to anti-FLAG M2 monoclonal antibody (SIGMA) that was diluted to 1000-fold with TBS-T+BA, and incubated at 37° C. for 1 hour or more. After that, the PVDF membrane was washed three times with TBS-T with shaking (10 minutes or more for each wash), and then added with HRP-labeled anti-mouse IgG antibody (Cell Signaling Technology) that was diluted to 1000-fold with TBS-T+BA, and incubated at 37° C. for 1 hour or more. Finally, the PVDF membrane was washed three times with TBS-T shaking (10 minutes or more for each wash), followed by detection of the expressed protein that reacted with an anti-FLAG antibody, by using the ECL Plus Western Blotting Detection System (Amersham biosciences). The chemiluminescence was visualized with a detection device, Lumino Imaging Analyzer (TOYOBO).

The result is shown in FIG. 1. The hj03796 expressed as a FLAG-tagged protein was detected as a single band between 220 kDa and 97.4 kDa (lane 1 in FIG. 1). The hj03796DH/PH was detected by the anti-FLAG antibody as a single band at approximately 50 kDa (lane 4 in FIG. 1). The deduced molecular weights of a protein encoded by hj03796 (hereinafter, the protein may be referred to hj03796 protein) and hj03796DH/PH, are approximately 150 kDa, and approximately 43 kDa, respectively. Therefore, the aforementioned single bands are believed to be hj03796, and hj03796DH/PH, respectively. In addition, proto-Dbl DH/PH was detected by the anti-FLAG antibody as a single band at approximately 40 kDa (lanes 2 and 5 in FIG. 1). None of these bands were detected in the protein solution obtained in the same manner from a control cell that was not transfected with the vector (lanes 3 and 6).

Thus, hj03796 protein, hj03796DH/PH and proto-Dbl DH/PH were obtained.

Example 3

Detection of Binding to a Rho Family Protein

The hj03796 DH/PH(C-terminal FLAG-tagged protein) expression vector constructed in Example 2 was used in studying the binding of hj03796 DH/PH to a Rho family protein, by using a pull-down assay.

Cdc42, RhoA, and Rac1 were used as Rho family proteins. The expression vector for expressing each of these proteins as an N-terminal GST-fusion protein was constructed as described later.

The proto-Dbl DH/PH was used as a positive control. The expression vector for expressing the proto-Dbl DH/PH as a C-terminal FLAG-tagged protein was the same as that constructed in Example 2. The proto-Dbl is a proto-type of Rho-GEF, and its activation is considered to be an oncogenic activation. The activation of proto-Dbl is caused by a deletion of the N-terminal side of its amino acid sequence from the $1^{st}$ to $497^{th}$ nucleotides. That is to say, the C-terminal region of proto-Dbl containing the DH/PH domain, activates a Rho family protein (Non-Patent Reference 1). Such a region has been referred to as an oncogenic-Dbl. The proto-Dbl DH/PH used in this Example is a deletion mutant of a proto-Dbl having an amino acid sequence of proto-Dbl from the $494^{th}$ to the $811^{th}$ nucleotides, which is shorter than the oncogenic-Dbl. It has been reported that the oncogenic-Dbl bound to Cdc42, RhoA, and Rac1, and that it exhibited the GEF activity for Cdc42 and RhoA, while it did not exhibit the GEF activity for Rac1 (Non-Patent Reference 2).

The specificity of the binding of the hj03796 DH/PH, or the proto-Dbl DH/PH, to a Rho family protein was examined using an N-terminal GST-fusion β-glucuronidase (hereinafter, may be abbreviated as GST-GUS) as a negative control.

The hj03796 DH/PH expression vector, or the proto-Dbl DH/PH expression vector, was mixed with the Rho family protein expression vector in a serum-free DMEM, subsequently mixed with LipofectAMINE 2000 in DMEM, and incubated at room temperature for 20 minutes. The obtained mixture was added to 293EBNA cells. The cells had been seeded the day before at $6.0 \times 10^4$ cells/well in a 24 well plate, and cultured at 37° C. overnight in the presence of 5% $CO_2$, for use in this experiment. The cells subjected to transfection were incubated at 37° C. for 2 days in the presence of 5% $CO_2$. After culturing, the cells were washed with PBS-EDTA, and then lysed with lysis buffer (the same composition as in Example 2) containing 1% protease inhibitor cocktail (SIGMA), to prepare a cell lysate.

Each cell lysate was subjected to a pull-down assay for detecting the binding of the hj03796 DH/PH, or the proto-Dbl DH/PH, to a Rho family protein. 300 μL of each cell lysate, 20 μL of Glutathione Sepharose 4B in the lysis buffer, and 100 μL of the lysis buffer were mixed. Each sample was prepared in such a way that the final concentration of $MgCl_2$ and dithiothreitol (DTT) was 1 mM. After reacting at 4° C. for 1 hour with rotating by rotator, each sample was washed three times with 1 mL of cold lysis buffer (the final concentration of $MgCl_2$ was 1 mM) by centrifugation at 1,000 rpm for 15 seconds at 4° C. After washing and removing the supernatant, the Glutathione Sepharose 4B was added with 40 μL of a solution that was prepared by mixing SDS-PAGE sample buffer (the same composition as in Example 2) with an equal volume of the lysis buffer. After that, it was mixed with a mixer and subjected to a heat treatment at 100° C. for 5 minutes, to prepare a sample for electrophoresis. SDS-polyacrylamide gel electrophoresis was carried out, and then the gel was equilibrated for 5 minutes or more in a blotting buffer (the same composition as in Example 2). The proteins were transferred onto a PVDF membrane. After blotting, the PVDF membrane was subjected to blocking at 4° C. overnight, in TBS-T+BA (the same composition as in Example 2). After blocking, the PVDF membrane was washed with TBS-T (the same composition as in Example 2) with shaking for 10 minutes or more.

The PVDF membrane was added to anti-FLAG M2 monoclonal antibodies (SIGMA) that was diluted to 1000-fold with TBS-T+BA, and incubated at 37° C. for 1 hour or more. After that, the PVDF membrane was washed three times with TBS-T with shaking (10 minutes or more for each wash), and then added to HRP-labeled anti-mouse IgG antibody (Cell Signaling Technology) that was diluted to 1000-fold with TBS-T+BA and incubated at 37° C. for 1 hour or more. Finally, the PVDF membrane was washed three times with TBS-T with shaking (10 minutes or more for each wash), followed by detection of the expressed protein that reacted with anti-FLAG antibodies by using the ECL Plus Western Blotting Detection System (Amersham biosciences). The chemiluminescence was visualized with a Lumino Imaging Analyzer (TOYOBO) detection device.

Figure 2:
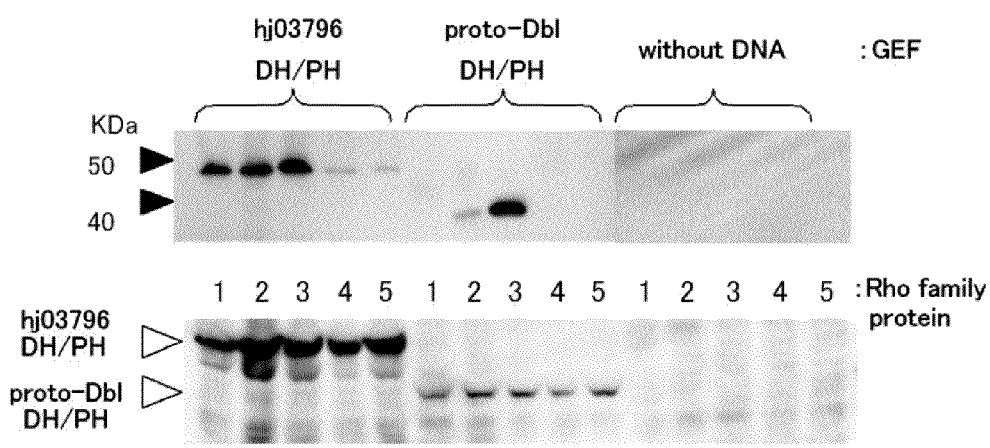
FIG. 2 shows, in the upper panel, a band corresponding to the binding of proteins (hj03796DH/PH), that are encoded by DNA consisting of a partial sequence of the cDNA clone hj03796, and that contain a DH/PH domain coding region to Rac1 (lane 1), RhoA (lane 2), and Cdc42 (lane 3). The proteins were detected from a cell lysate prepared from cells in which the DNA was co-expressed with Rac1 gene (lane 1), RhoA gene (lane 2), or Cdc42 gene (lane 3). The pull-down assay was used for measuring the binding. Such a band was not observed when using a GST-fusion β-glucuronidase instead of the Rho family proteins, as a negative control, or when the Rho family protein gene was not expressed (lanes 4 and 5, respectively). Proto-Dbl DH/PH was used as a positive control. The expression of hj03796DH/PH, or proto-Dbl DH/PH, was almost equivalent in each cell lysate (the lower panel). (Example 3)

When the anti-FLAG antibodies gave a band at the expected molecular weight, it was determined that the hj03796 DH/PH or the proto-Dbl DH/PH bound to a Rho family protein. As shown in FIG. 2, a band at approximately 50 kDa, corresponding to hj03796 DH/PH, was detected in all samples prepared from the cells in which hj03796 DH/PH was co-expressed with Rho family proteins, Rac1, RhoA, or Cdc42 (the upper panel of FIG. 2: lanes 1, 2 and 3 of hj03796 DH/PH). Meanwhile, a band at approximately 40 kDa, corresponding to proto-Dbl DH/PH, was detected in both samples prepared from the cells in which proto-Dbl DH/PH was co-expressed with RhoA or Cdc42 (the upper panel of FIG. 2: lanes 2 and 3 of proto-Dbl DH/PH). On the other hand, such a band was not detected in the sample prepared from the cell in which proto-Dbl DH/PH was co-expressed with Rac1 (the upper panel of FIG. 2; lane 1 of proto-Dbl DH/PH). Such a band was not detected in the sample prepared from the cell in which hj03796 DH/PH or proto-Dbl DH/PH was co-expressed with GST-fusion β-glucuronidase (the upper panel of FIG. 2; lane 4). Thus, hj03796 DH/PH and proto-Dbl DH/PH did not bind to GST-GUS. In addition, such a band was not observed when not expressing the Rho family protein (lane 5). The amount of expression of hj03796 DH/PH and proto-Dbl DH/PH in each cell was almost the same when compared to the cell lysate (the lower panel of FIG. 2).

These results revealed that the hj03796 DH/PH bound to Cdc42, RhoA, or Rac1. Therefore, the hj03796 full-length protein that contains the hj03796 DH/PH is considered to bind to these Rho family proteins, and possibly to have a function as Rho-GEF.

The expression vector used in this Example, for expressing Cdc42, RhoA, or Rac1 as an N-terminal GST-fusion protein, was constructed as described below.

The expression vector for Cdc42, RhoA, or Rac1 was constructed using Gateway™ cloning technology (Invitrogen). A gene that encodes each Rho family protein, Cdc42, RhoA, or Rac1, was amplified by pfu turbo (Stratagene), using spleen first strand DNA of Multiple Tissue cDNA Panels (Clontech) as a template. The amplified product was inserted into pENTR/D in a reaction using the TOPO cloning system to prepare an entry vector. The primers, Cdc42-s1 (SEQ ID NO: 13) and Cdc42-as1 (SEQ ID NO: 14), were used for the amplification reaction for Cdc42. The primers, RhoA-s1 (SEQ ID NO: 15) and RhoA-as1 (SEQ ID NO: 16), were used for the amplification reaction for RhoA. The primers, Rac 1-s1 (SEQ ID NO: 17) and Rac1-as1 (SEQ ID NO: 18), were used for the amplification reaction for Rac1. The constructed entry vector was then subjected to a recombination reaction in the presence of LR clonase, by using pDEST27 that is an N-terminal GST-fusion protein-expression vector, to prepare an expression vector for a GST-fusion Rho family protein. Correct insertion of the nucleotide sequence of the coding region of each gene was verified by sequencing. The sequencing reaction was carried out using a DYEnamic ET Terminator Cycle Sequencing Kit (Amersham Biosciences). Electrophoresis and analysis were performed using an ABI PRISM 377.

Example 4 hj03796 DH/PH Induced Acceleration of the Activation of Cdc42

The GEF activity of hj03796 DH/PH for a Rho family protein was examined using the hj03796 DH/PH(C-terminal FLAG-tagged protein) expression vector constructed in Example 2, by an effector pull-down assay. Cdc42, RhoA, and Rac1 were used as a Rho family protein. Each of these Rho family proteins was expressed as an N-terminal 3×FLAG-tagged protein.

The hj03796 DH/PH(C-terminal FLAG-tagged protein) expression vector and the expression vector for expressing any one of the aforementioned Rho family proteins were transfected into 293EBNA cells that were plated in a 24 well plate. The transfection of cells with the vectors was carried out using a LipofectAMINE 2000. Cells which were not transfected with any vector, but were treated only with LipofectAMINE 2000, were used as a negative control. On the day after gene transfection, the cell was lysed with the lysis buffer containing a protease inhibitor cocktail of 1/100 concentration (SIGMA), to prepare a cell lysate. Then, the cell lysate was subjected to a reaction with effector beads (UPSTATE) at 4° C., for 1 hour. The effector beads used herein were glutathione agarose effector beads that were conjugated with a GST-fusion protein prepared by adding a GST-tag to a binding domain of PAK-1, or Rhotekin, to the active the Rho family protein. After the reaction, the effector beads were washed with the lysis buffer, and then subjected to extraction with extract solution (Tris/SDS/β-mercaptoethanol: Daiichi Pure Chemicals). The obtained extract was subjected to Western blotting using SDS-PAGE to carry out the detection of the FLAG-tagged protein using an anti-FLAG antibody. The lysis buffer was composed of 25 mM HEPES (pH 7.5), 150 mM NaCl, 10 mM $MgCl_2$, 1 mM EDTA, 2% glycerol, and 1% Triton X-100.

If the hj03796 DH/PH had a GEF activity for a Rho family protein, the hj03796 DH/PH would induce conversion of the Rho family protein from an inactive form (GDP-bound form) to an active form (GTP-bound form). PAK-1 that was used as effector beads is known to bind to both the active Cdc42 and the active Rac1. In addition, Rhotekin binds to the active RhoA. Therefore, if the hj03796 DH/PH had a GEF activity for a Rho family protein, the Rho family protein that binds to the effector beads would increase in amount. Then, it was decided that the hj03796 DH/PH had a GEF activity, when the band of the Rho family protein was detected by using an anti-FLAG antibody, more clearly in the sample prepared from the cells in which the hj03796 DH/PH was co-expressed with the Rho family proteins, than in the sample prepared from the cells in which only the Rho family proteins were expressed.

Figure 3A:
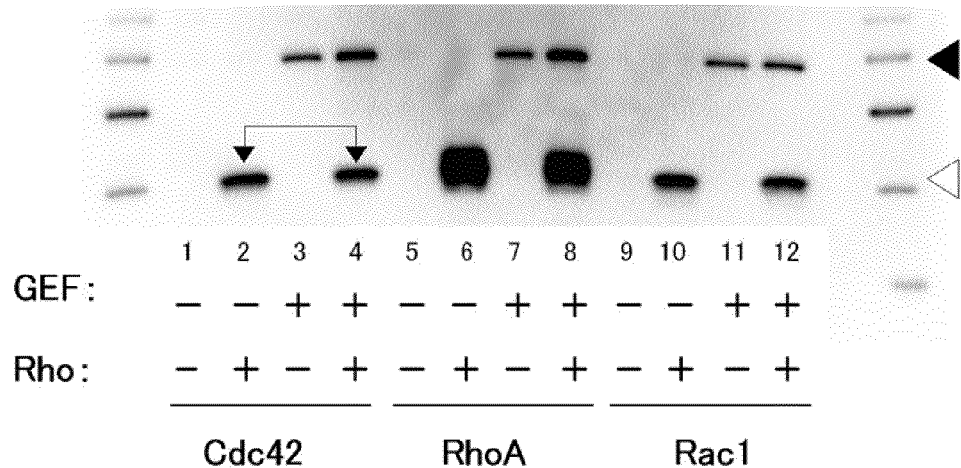
FIG. 3-A shows that the expression of hj03796DH/PH, or a Rho family protein was almost equivalent in cells in which hj03796DH/PH was co-expressed with a Rho family protein, and a cell in which hj03796DH/PH, or a Rho family protein, was expressed. In the figure, GEF means hj03796DH/PH, and Rho means a Rho family protein. The black arrow head indicates hj03796DH/PH, while the white arrow head indicates a Rho family protein. (Example 4)
Figure 3B:
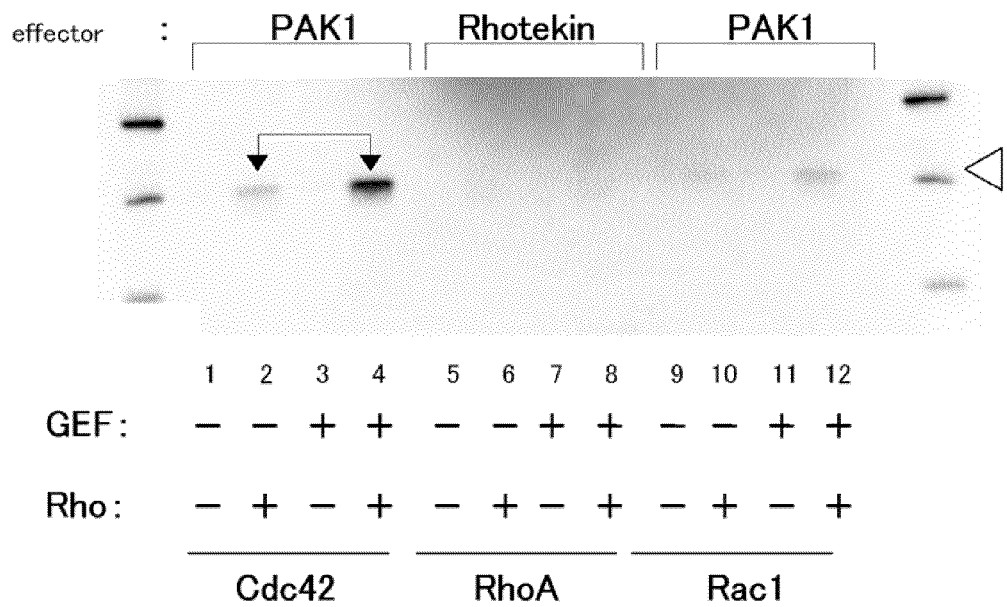

The results were shown in FIG. 3-A and FIG. 3-B. FIG. 3-A shows the results obtained by detecting the expression of the Rho family proteins, and/or the hj03796 DH/PH that were contained in each cell lysate, by using anti-FLAG antibodies. The expression of each Rho family protein (in the Figure, it is indicated as Rho) was almost the same in any of the cells in which the Rho family protein was co-expressed with the hj03796 DH/PH, and the cells in which only the Rho family protein was expressed (lanes 2, 4, 6, 7, 10, and 12 in FIG. 3-A: indicated with white arrow head). As for RhoA, multiple bands were observed (lanes 6 and 8 in FIG. 3-A). This was believed to be due to the effect of proteases. In addition, the expression of the hj03796 DH/PH (in the Figure, it is indicated as GEF) was almost the same in any of the cells in which only the hj03796 DH/PH was expressed, and the cells in which the hj03796 DH/PH was co-expressed with the Rho family protein (lanes 3, 4, 7, 8, 11 and 12 in FIG. 3-A: indicated with black arrow head).

FIG. 3-B shows the results obtained by an effector pull-down assay using the aforementioned cell lysates. In the sample (lane 4 in FIG. 3-B) prepared from the cells in which Cdc42 was co-expressed with the hj03796 DH/PH (in the Figure, it is indicated as GEF), the band was detected more clearly that in the sample (lane 2 in FIG. 3-B) prepared from the cells in which only Cdc42 was expressed. That is to say, the activated Cdc42, capable of binding to PAK-1, was increased in the cells in which Cdc42 was co-expressed with the hj03796 DH/PH. These results revealed that the hj03796 DH/PH has a GEF activity for Cdc42. Therefore, it is believed that the hj03796 full-length protein that contains the hj03796 DH/PH also has a GEF activity for Cdc42. Thus, it was found that the hj03796 has a function of accelerating the activation of Cdc42.

INDUSTRIAL APPLICABILITY

The protein, encoded by a polynucleotide according to the present invention, bound to a Rho family protein and accelerated the activation of the Rho family protein. Use of the present proteins and polynucleotides allows for the elucidation and regulation of the Rho family protein mediated signal transduction pathway and cellular function. Further, use of the present proteins and polynucleotides allow for diagnosis, prevention, and/or treatment of a disease, for example, a stomach tumor, due to an abnormal function of the present proteins and/or an abnormal expression of the present polynucleotides. Thus, the present invention is extremely useful in a wide range of fields including basic research and pharmaceutical development.

GENERAL DESCRIPTION OF THE SEQUENCES

SEQ ID NO: 1: a polynucleotide that encodes the protein (SEQ ID NO: 2) having a function as a guanine nucleotide exchange factor.

SEQ ID NO: 1: (602):(1126) a region encoding a Dbl homology domain.

SEQ ID NO: 1: (1202):(1495) a region encoding a pleckstrin homology domain.

SEQ ID NO: 3: a partial sequence of SEQ ID NO: 1 consisting of the nucleotides from the $581^{st}$ to the $1675^{th}$, which contains a region encoding a Dbl homology domain and a pleckstrin homology domain, where the polynucleotide encodes the amino acid sequence set forth in SEQ ID NO: 4.

SEQ ID NO: 5: A polynucleotide that has a kozak consensus sequence and a methionine codon in its 5'-terminal, followed by a partial sequence of SEQ ID NO: 1 consisting of the nucleotides from the 581$^{st}$ to the 1675$^{th}$, which contains a region encoding a Dbl homology domain and a pleckstrin homology domain, where the polynucleotide encodes the amino acid sequence set forth in SEQ ID NO: 6.

SEQ ID NO: 5: (1):(4) a kozak consensus sequence.

SEQ ID NO: 5: (5):(7) a methionine codon.

SEQ ID NO: 7: designed polynucleotide based on the sequence of SEQ ID NO:1 for use as a primer.

SEQ ID NO: 8: designed polynucleotide based on the sequence of SEQ ID NO:1 for use as a primer.

SEQ ID NO: 9: designed polynucleotide based on the sequence of SEQ ID NO:1 for use as a primer.

SEQ ID NO: 10: designed polynucleotide based on the sequence of SEQ ID NO:1 for use as a primer.

SEQ ID NO: 11: designed polynucleotide based on the sequence of proto-Dbl for use as a primer.

SEQ ID NO: 12: designed polynucleotide based on the sequence of proto-Dbl for use as a primer.

SEQ ID NO: 13: designed polynucleotide based on the sequence of Cdc42 for use as a primer.

SEQ ID NO: 14: designed polynucleotide based on the sequence of Cdc42 for use as a primer.

SEQ ID NO: 15: designed polynucleotide based on the sequence of RhoA for use as a primer.

SEQ ID NO: 16: designed polynucleotide based on the sequence of RhoA for use as a primer.

SEQ ID NO: 17: designed polynucleotide based on the sequence of Rac1 for use as a primer.

SEQ ID NO: 18: designed polynucleotide based on the sequence of Rac1 for use as a primer.

SEQ ID NO: 19: designed oligonucleotide having a kozak consensus sequence followed by a methionine codon.

SEQ ID NO: 20: Cdc42 gene.

SEQ ID NO: 21: Cdc42 SEQ ID NO: 22: RhoA gene.

SEQ ID NO: 23: RhoA

SEQ ID NO: 24: Rac1 gene.

SEQ ID NO: 25: Rac1

SEQ ID NO: 26: a gene encoding proto-Dbl (SEQ ID NO: 27).

What is claimed is:

1. An isolated antibody that specifically binds to a protein consisting of the amino acid sequence set forth in SEQ ID NO: 2.

2. A reagent kit comprising the isolated antibody according to claim 1.

* * * * *

UNITED STATES PATENT AND TRADEMARK OFFICE
CERTIFICATE OF CORRECTION

PATENT NO.         : 8,173,778 B2
APPLICATION NO.    : 12/651145
DATED              : May 8, 2012
INVENTOR(S)        : Ohara et al.

It is certified that error appears in the above-identified patent and that said Letters Patent is hereby corrected as shown below:

Title page item 73 ASSIGNEE:

Line 1, "Daiichi Sankyo Company, Limited,
Tokyo (JP)" should read
--Daiichi Sankyo Company, Limited,
Tokyo (JP)
Kazusa DNA Research Institute Foundation
Chiba (JP)--.

Signed and Sealed this
Tenth Day of July, 2012

David J. Kappos
*Director of the United States Patent and Trademark Office*